US008709296B2

(12) United States Patent
Kiyoshima et al.

(10) Patent No.: US 8,709,296 B2

(45) Date of Patent: Apr. 29, 2014

(54) METAL COLLOIDAL PARTICLES, METAL COLLOID AND USE OF METAL COLLOID

(75) Inventors: Reiko Kiyoshima, Mito (JP); Toshiharu Hayashi, Naka-gun (JP)

(73) Assignees: Mitsubishi Materials Corporation, Tokyo (JP); Mitsubishi Materials Electronic Chemicals Co., Ltd., Akita-Shi (JP)

( * ) Notice: Subject to any disclaimer, the term of this patent is extended or adjusted under 35 U.S.C. 154(b) by 870 days.

(21) Appl. No.: 11/570,953

(22) PCT Filed: Jun. 22, 2005

(86) PCT No.: PCT/JP2005/011459

§ 371 (c)(1), (2), (4) Date: Feb. 9, 2007

(87) PCT Pub. No.: WO2006/001310

PCT Pub. Date: Jan. 5, 2006

(65) Prior Publication Data

US 2008/0277630 A1 Nov. 13, 2008

(30) Foreign Application Priority Data

Jun. 25, 2004 (JP) ................................ P2004-187872
Aug. 12, 2004 (JP) ................................ P2004-235261
Sep. 29, 2004 (JP) ................................ P2004-284027

(51) Int. Cl.
*H01B 1/02* (2006.01)
*C08K 3/08* (2006.01)

(52) U.S. Cl.
USPC .......................................... 252/514; 524/440

(58) Field of Classification Search
USPC .................. 252/500, 514; 524/440; 148/582; 523/161, 164
See application file for complete search history.

(56) References Cited

U.S. PATENT DOCUMENTS 5,639,901 A 6/1997 Schulz et al.
5,925,463 A 7/1999 Reetz et al.
6,136,083 A 10/2000 Schmidt et al.

FOREIGN PATENT DOCUMENTS

| | | | |
|---|---|---|---|
| DE | 195 20 964 A1 | 12/1996 | |
| EP | 0668264 A2 | 8/1995 | |
| EP | 0 857 707 A2 | 8/1998 | |
| EP | 1 308 228 A1 | 5/2003 | |
| EP | 1308228 * | 7/2003 | |
| JP | 05-310488 | 11/1993 | |
| JP | 7-310107 A | 11/1995 | |
| JP | 8-176620 A | 7/1996 | |
| JP | A-08-196316 | 8/1996 | |
| JP | A-08-239703 | 9/1996 | |
| JP | 10-160737 | 6/1998 | |
| JP | 11-080647 | 3/1999 | |
| JP | 2000-160210 | 6/2000 | |
| JP | 2001-019872 | 1/2001 | |
| JP | 2001-172705 A | 6/2001 | |
| JP | 2001-325831 | 11/2001 | |
| JP | A-2003-301227 | 10/2003 | |
| JP | 2004-33901 A | 2/2004 | |
| JP | 2004-162169 * | 6/2004 | ................ B22F 9/00 |
| JP | 2004162169 | 6/2004 | |
| JP | 2004-263222 * | 9/2004 | |
| JP | A-2005-320615 | 11/2005 | |
| KR | 20030023746 | 3/2003 | |
| WO | WO-99/01766 A1 | 1/1999 | |
| WO | WO-01/68596 A1 | 9/2001 | |

OTHER PUBLICATIONS

Toge, N.O., et al., Extended Abstracts of the 66th Fall Meeting of the Chemical Society of Japan, p. 322—D115.

Mennig, Martin, et al., "Gold Colloids in Sol-Gel Derived SiO2 Coatings on Glass and their Linear and Nonlinear Optical Properties," SPIE Sol-Gel Optics III, vol. 2288, 1994, p. 130-139.

International Search Report for PCT/JP2005/011459 mailed Aug. 16, 2005.

"Influence of a Terminal Functionality on the Physical Properties of Surfactant-Stabilized Gold Nanoparticles" by Johnson et al., 1998 American Chemical Society, *Langmuir* 1998, vol. 14, No. 23, Nov. 23, 1998, pp. 6639-6647.

European Search Report mailed May 4, 2011 for the corresponding European patent application No. 11159706.8.

Office Action mailed Mar. 26, 2008 for the corresponding Japanese Patent Application No. 2005-108967.

Office Action mailed Sep. 24, 2008 for the corresponding Japanese Patent Application No. 2005-108965.

* cited by examiner

*Primary Examiner* — Monique Peets

(74) *Attorney, Agent, or Firm* — Leason Ellis LLP.

(57) ABSTRACT

With respect to the metal colloid of the present invention, metal colloidal particles capable of forming a metal colloid by dispersing in either or both of an aqueous dispersion medium and a nonaqueous dispersion medium in a predetermined proportion while mixing, comprise metal particles and a protective agent coordination-modified on the surface of the particles, the protective agent having a carbon skeleton containing either or both of sulfur and oxygen in the molecule, and having a structure of being coordination-modified on the surface of the metal particles using an atom or an atomic group of either or both of sulfur and oxygen as an anchor, wherein the protective agent has one, or two or more functional groups selected from the group consisting of alkoxysilyl group, silanol group and hydroxyalkyl group in a molecular structure.

4 Claims, 24 Drawing Sheets

X PROTECTIVE AGENT COORDINATION-MODIFIED SITE
R PROTECTIVE AGENT END SITE

1

6
5
4
3
2

METAL COLLOIDAL PARTICLES, METAL COLLOID AND USE OF METAL COLLOID

CROSS REFERENCE TO PRIOR APPLICATION

This is a U.S. national phase application under 35 U.S.C. §371 of International Patent Application No. PCT/JP2005/011459, filed Jun. 22, 2005, and claims the benefit of Japanese Application Nos. 2004-187872, filed Jun. 25, 2004, 2004-235261, filed Aug. 12, 2004 and 2004-284027, filed Sep. 29, 2004, all of which are incorporated by reference herein. The International Application was published in Japanese on Jan. 5, 2006 as International Publication No. WO2006/001310 A1 under PCT Article 21(2).

TECHNICAL FIELD

The present invention relates to a metal colloid which is excellent in long-term stability of a colloidal solution and is suited for thin-filming, and its use. Furthermore, the present invention relates to a metal colloid which can easily form a metal specular glossy area on various base materials, and its use. Particularly, the present invention relates to metal colloidal particles and a metal colloid, which can easily form a metal glossy area showing various gold-based color tones on various base materials, and the use of the metal colloid.

BACKGROUND ART

Since a metal colloid shows a color peculiar to the particle size and the kind of metal, a measuring tip for optical analysis which utilizes the metal colloid as an optical filter is known (see, for example, Japanese Unexamined Patent Application, First Publication No. Hei 10-160737). The metal colloid used in this measuring tip is obtained by previously preparing a metal colloidal dispersion and mixing the colloidal dispersion with a silane coupling agent, thereby to introduce an amino group as a functional group into the surface of the colloid. However, when the metal colloid is formed and then the surface protective agent is introduced into the surface of the colloid, the protective agent may not be sufficiently introduced because of the deposit which has already been present on the metal surface of the colloid. Since the metal colloid is synthesized in an aqueous system, the surface protective agent is influenced by hydrolysis and thus stability of the colloid deteriorates. Furthermore, the amino group to be introduced into the amino group is used as a functional group for a protein or enzyme, and therefore the amino group is located outside and the siloxane bond of the protective agent is located on the surface of the colloid. Therefore, according to surface properties of colloidal particles, adhesion between the protective agent and the colloidal particles may become insufficient and thus the metal colloidal film is unstable.

In addition, as a metal colloid used as a conductive ink or a material of a conductive coat, a highly conductive aqueous metal colloidal solution containing an organic component is known (see, for example, Japanese Unexamined Patent Application, First Publication No. 2001-325831). However, this metal colloid is also produced by the aqueous reaction and is obtained by mixing with the organic component after forming a metal colloid and therefore have the same problems described above.

Also it has hitherto been known to use a metal colloid as a colorant of a coating composition or glass. For example, it is known that a metal colloid is prepared by reducing a metal compound in the presence of a high-molecular weight pigment dispersant (see, for example, Japanese Unexamined Patent Application, First Publication No. Hei 11-80647). However, this method also includes a major specific example wherein a metal colloid is formed by the aqueous reaction and therefore have the same problems described above. Furthermore, a coexisting polymer protective colloid is a pigment dispersant and is not obtained by bonding a protective agent comprising a silane coupling agent with the surface of colloidal particles.

Furthermore, there is known a method of mixing chlorauric acid with a protective polymer to form a gold colloid, the method using a protective polymer having an amino group in the end or side chain portion opposite the surface of metal particles (see, for example, Japanese Unexamined Patent Application, First Publication No. 2000-160210). This method is intended to produce a gold colloid without using a reducing agent such as sodium borohydride which is commonly used, and the reductive action of a protective polymer is utilized. However, in this case, since the protective agent is a polymer, the resulting colloid contains a lot of organic chains and is insufficient in heat resistance.

A gold ink, which has hitherto been sold and used as a gold powder, has been obtained by treating the surface of a flat shaped brass powder (copper-zinc alloy powder) with a saturated fatty acid having 16 to 22 carbon atoms and used for lithographic printing. However, a lithographic printing ink has high viscosity and is not suited for use as an ink having low viscosity which is used for gravure printing. Therefore, there is disclosed a gold powder for gold ink which is prepared by coating 100 parts by weight of a flaky brass metal powder having an average particle size of 10 μm or less with 0.1 to 2 parts by weight of a saturated fatty acid having 14 to 22 carbon atoms and 0.1 to 2 parts by weight of a fatty acid amide having 14 to 22 carbon atoms while mixing (see, for example, Japanese Unexamined Patent Application, First Publication No. 2001-19872) as measure which can attain the same specular gloss as that in case of gravure printing in the lithographic printing and also can exert the same effect as that of a smooth paper in case of using a paper having no smooth surface. In Japanese Unexamined Patent Application, First Publication No. 2001-19872, when using, as a printing ink, a gold ink obtained by mixing a gold powder having an average particle size of 10 μm or less prepared by a mechanical crushing method with a predetermined amount of the saturated fatty acid and the fatty acid amide, a metal specular glossy film is obtained.

Also, a method of preparing a metal colloid with a silica film by a heat treatment using an amino group-containing alkoxysilane is known (see, for example, Extended Abstracts of 66th Fall Meeting of the Chemical Society of Japan, pp. 322 and Proc SPIE Sol-gel Optics III, Vol. 2288, pp. 130-139).

However, the amino group-containing silane used in this method is used so as to promote the production of a colloid from chlorauric acid as a raw material, and is not used as the protective agent. According to this method, since colloidalization is conducted by a heat treatment, properties of the colloid produced vary depending on the temperature and stable permeation and absorption performances. Moreover, hydrolysis of a sol-gel solution is promoted by an acid containing in a raw material in an alkoxide, and thus lifetime of the solution tends to be shortened and furthermore the solution is unstable.

SUMMARY OF THE INVENTION

Furthermore, it is known that a gold colloid obtained by protecting nano-sized gold particles with a protective agent having a low molecular weight shows gold metal gloss after drying at room temperature. Examples of the protective agent used in this case include fatty acids such as citric acid having 1 to 8 carbon atoms, adipic acid, malic acid, acetic acid, propionic acid, butyric acid, valeric acid and caproic acid; and amines such as monomethylamine, dimethylamine, trimethylamine, monoethylamine, diethylamine, triethylamine, monopropylamine, isopropylamine, monobutylamine, secondary butylamine, tertiary butylamine, monopentylamine and monohexylamine. However, in case of the gold colloid obtained by using the protective agent, the upper limit of the concentration of metal contained in the colloidal solution is about 5% by weight. When the concentration is more than the upper limit, there arise problems that aggregation or gelation occurs and the concentration can not be increased because of poor stability. For example, in order to exhibit golden gloss by coating and air-drying a metal colloid made of gold as metal, it is necessary that the gold content is at least 20% by weight based on a fibrous base material such as paper. When the concentration of the metal colloid protected with a low-molecular weight protective agent is increased in disregard of stability, the coated surface shows metal gloss but is far from golden gloss and also the coat is easily peeled off because of poor adhesion.

When a polymer binder is added to the metal colloid so as to solve this problem, nano-sized metal particles cause plasmon color development (SPR: Surface Plasma) due to surface plasma resonance and show are a red or reddish violet color, and thus no golden gloss is exhibited.

Heretofore, there has never been obtained a metal colloid which exhibit gold color tones such as pink gold and green gold, based on gold used in jewelries.

The present inventors have been investigated about stability with time so as to enhance additional value of the metal colloid. As a result of intensive study, they have found to provide a metal colloid having excellent stability with time by using a protective agent containing at least one of sulfur and oxygen, or using a protective agent containing nitrogen. Whereby, any influence is not exerted on metal gloss of a coat formed by coating a metal colloidal coating material.

First object of the present invention is to solve the above problems in a conventional metal colloid and the method of preparing the same and to provide a conventional colloid which is excellent in long-term stability of a colloidal solution and is suited for thin-filming, and its use.

Second object of the present invention is to provide metal colloid which can easily form a metal specular glossy area on various base materials, and its use.

Third object of the present invention is to provide a metal colloidal particles and a metal colloid, which can easily form a metal glossy area showing various color tones, and the use of the metal colloid.

Fourth object of the present invention is to provide a metal colloid-containing coat formed article, a transfer sheet and a base material with a conductive film, wherein a coat having a metal specular glossy area and excellent heat resistance is formed.

Five object of the present invention is to provide a metal colloid-containing coat formed article, a transfer sheet and a base material with a conductive film, wherein a coat showing various color tones is formed.

Sixth object of the present invention is to provide a base material with a conductive film, comprising a low-resistance conductive film Seventh object of the present invention is to provide a pen, a brush-pencil, a cartridge for pen, a disposable ampul, a stamp pad and a seal impression, which are excellent in quality-retaining property.

Eighth object of the present invention is to provide a drawn material having color tone and metal gloss peculiar to metal.

The first aspect of the present invention provides metal colloidal particles capable of forming a metal colloid by dispersing in either or both of an aqueous dispersion medium and a nonaqueous dispersion medium in a predetermined proportion while mixing, comprising metal particles and a protective agent coordination-modified on the surface of the particles, the protective agent having a carbon skeleton containing either or both of sulfur and oxygen in the molecule, and having a structure of being coordination-modified on the surface of the metal particles using an atom or an atomic group of either or both of sulfur and oxygen as an anchor, wherein the protective agent has one, or two or more functional groups selected from the group consisting of alkoxysilyl group, silanol group and hydroxyalkyl group in a molecular structure.

Since the protective agent is firmly bonded to the surface of metal particles using an atom or an atomic group of either or both of sulfur and oxygen as an anchor, high stability is attained. The alkoxysilyl group, the silanol group and the hydroxyalkyl group contained in the molecular structure of the protective agent have high reactivity and chemically bonded to all base materials. Metal particles are spontaneously self-organized and cause closest packing, and are condensed with a reactive functional group. Therefore, it is considered that a coat obtained by coating or spraying the metal colloid made of the metal colloidal particles according to the first aspect has high strength and is converted into an organic-inorganic hybrid bulk between particles.

The second aspect of the present invention provides the metal colloidal particles of the invention according to the first aspect, wherein the protective agent further contains nitrogen and has a structure of being coordination-modified on the surface of metal particles using nitrogen or an atomic group including nitrogen as an anchor.

The third aspect of the present invention provides the metal colloidal particles of the invention according to the first aspect, wherein oxygen contained in the protective agent is derived from at least one selected from the group consisting of carbonyl group, carboxyl group, aldehyde group, amide group and sulfonyl group.

The fourth aspect of the present invention provides the metal colloidal particles of the invention according to any one of the first to third aspects, wherein either or both of the alkoxysilyl group and the hydroxyalkyl group contained in the protective agent are chelete-coordinated by a chelating agent.

The fifth aspect of the present invention provides the metal colloidal particles of the invention according to the first aspect, wherein the metal particles constituting the metal colloidal particles are one or two or more metal particles made of metal selected from the group consisting of Au, Ag, Pt, Cu, Pd, Ni, Zn, Ru, Rh and Ir.

The sixth aspect of the present invention provides the metal colloidal particles of the invention according to the fifth aspect, wherein the metal particles constituting the metal colloidal particles are made of Au and have an average particle size within a range from 1 to 60 nm.

The seventh aspect of the present invention provides the metal colloidal particles of the invention according to any one of the first to sixth aspects, wherein a coat formed by coating, spraying, printing, ejecting or transferring a metal colloid, which is obtained by dispersing metal colloidal particles containing Au colloidal particles as a main component and also containing 0.1 to 10% metal particles having an average particle size of 1 to 10 nm, in addition to the Au colloidal particles, in a dispersion medium, and removing the dispersion medium from the metal colloid, shows a pink gold color tone.

The eighth aspect of the present invention provides the metal colloidal particles of the invention according to any one of the first to sixth aspects, which are either or both of metal colloidal particles containing Au colloidal particles as a main component and also containing Ag particles and Cu particles as impurities, in addition to Au particles, and metal colloidal particles containing metal particles made of an alloy containing Au as a main component and also containing Ag and Cu as impurities, wherein when the content of impurities in the metal colloidal particles is from 5 to 40% and the content of Ag in impurities is from 40 to 60% by weight based on 100% by weight of impurities, a coat formed by coating, spraying, printing, ejecting or transferring a metal colloid, which is obtained by dispersing the metal colloidal particles in a dispersion medium, and removing the dispersion medium from the metal colloid, shows a yellow gold color tone.

The ninth aspect of the present invention provides the metal colloidal particles of the invention according to any one of the first to sixth aspects, which are either or both of metal colloidal particles containing Au colloidal particles as a main component and also containing Ag particles and Cu particles as impurities, in addition to Au particles, and metal colloidal particles containing metal particles made of an alloy containing Au as a main component and also containing Ag and Cu as impurities, wherein when the content of impurities in the metal colloidal particles is from 5 to 40% and the content of Ag in impurities is 65% by weight or more based on 100% by weight of impurities, a coat formed by coating, spraying, printing, ejecting or transferring a metal colloid, which is obtained by dispersing the metal colloidal particles in a dispersion medium, and removing the dispersion medium from the metal colloid, shows a green gold color tone.

The tenth aspect of the present invention provides the metal colloidal particles of the invention according to any one of the first to sixth aspects, which are either or both of metal colloidal particles containing Au colloidal particles as a main component and also containing Ag particles and Cu particles as impurities, in addition to Au particles, and metal colloidal particles containing metal particles made of an alloy containing Au as a main component and also containing Ag and Cu as impurities, wherein when the content of impurities in the metal colloidal particles is from 5 to 40% and the content of Ag in impurities is 30% by weight or less based on 100% by weight of impurities, a coat formed by coating, spraying, printing, ejecting or transferring a metal colloid, which is obtained by dispersing the metal colloidal particles in a dispersion medium, and removing the dispersion medium from the metal colloid, shows a red gold color tone.

The eleventh aspect of the present invention provides the metal colloidal particles of the invention according to any one of the first to sixth aspects, which are either or both of metal colloidal particles containing Au colloidal particles as a main component and also containing Ag particles, Cu particles and Pd particles as impurities, in addition to Au particles, and metal colloidal particles containing metal particles made of an alloy containing Au as a main component and also containing Ag, Cu and Pd as impurities, wherein when the content of impurities in the metal colloidal particles is from 5 to 40% and the content of Ag in impurities is 30% by weight or less based on 100% by weight of impurities, a coat formed by coating, spraying, printing, ejecting or transferring a metal colloid, which is obtained by dispersing the metal colloidal particles in a dispersion medium, and removing the dispersion medium from the metal colloid, shows a pink gold color tone.

The twelfth aspect of the present invention provides the metal colloidal particles of the invention according to any one of the first to sixth aspects, which are either or both of metal colloidal particles containing Au colloidal particles as a main component and also containing Pd particles as impurities, in addition to Au particles, and metal colloidal particles containing metal particles made of an alloy containing Au as a main component and also containing Pd as impurities, wherein when the content of impurities in the metal colloidal particles is from 5 to 40%, a coat formed by coating, spraying, printing, ejecting or transferring a metal colloid, which is obtained by dispersing the metal colloidal particles in a dispersion medium, and removing the dispersion medium from the metal colloid, shows a white gold color tone.

The thirteenth aspect of the present invention provides a metal colloid which is characterized in that the metal colloidal particles of any one of any one of the first to twelfth embodiments are dispersed in either or both of an aqueous dispersion medium and a nonaqueous dispersion medium in a predetermined proportion while mixing.

The fourteenth aspect of the present invention provides a metal colloid which is characterized in that the metal colloidal particles of any one of the first to twelfth embodiments are mixed with a sol-gel solution in a predetermined proportion.

The fourteenth aspect of the present invention provides the metal colloid of the invention according to the fourteenth aspect, wherein the sol-gel solution is a solution capable of forming at least one compound selected from the group consisting of silica, titania, zirconia, alumina, tantalum oxide and niobium oxide.

The sixteenth aspect of the present invention provides a metal colloidal thin film which is characterized in that the metal colloidal particles of any one of the first to twelfth embodiments are dispersed in either or both of an aqueous dispersion medium and a nonaqueous dispersion medium in a predetermined proportion while mixing to form a metal colloid and a film is formed by using the metal colloid.

The seventeenth aspect of the present invention provides a metal colloid-containing coat formed article which is formed by coating, spraying, printing, ejecting or transferring the metal colloid of any one of the thirteenth to fifteenth embodiments on the surface of a base material, and removing the dispersion medium from the metal colloid.

The eighteenth aspect of the present invention provides a metal colloid-containing coat formed article, wherein the base material is jewelry and the jewelry is made of a noble metal clay.

The nineteenth aspect of the present invention provides the metal colloid-containing coat formed article of the invention according the seventeenth or eighteenth aspect, further comprising one, two or more kinds selected from the group consisting of metal powder, metal foil, fine metal particles, brightener, lame agent, cut pieces of colored paper, natural gems and artificial gems.

The twentieth aspect of the present invention provides the metal colloid-containing coat formed article of the according to the nineteenth aspect, wherein the metal used in the metal powder, metal foil or fine metal particles is Au.

The twenty-first aspect of the present invention provides a transfer sheet comprising a metal colloid-containing coat formed by coating, spraying, printing, ejecting or transferring the metal colloid of any one of the thirteenth to fifteenth aspects on a transfer substrate wherein either of both of the surface and the back surface are subjected to a release treatment, and removing the dispersion medium from the metal colloid.

The twenty-second aspect of the present invention provides the transfer sheet of the invention according to the twenty-first aspect, wherein the metal colloid-containing coat contains one, two or more kinds selected from the group consisting of metal powder, metal foil, fine metal particles, brightener, lame agent, cut pieces of colored paper, natural gems and artificial gems.

The twenty-third aspect of the present invention provides the transfer sheet of the invention according to the twenty-second aspect, wherein the metal used in the metal powder, metal foil or fine metal particles is Au.

The twenty-third aspect of the present invention provides a metal colloid-containing coat formed article comprising a transfer film transferred from the transfer sheet of any one of the twenty-first to twenty-third aspects.

The twenty-fifth aspect of the present invention provides the metal colloid-containing coat formed article of the invention according to the twenty-fourth aspect, further comprising one, or two or more kinds selected from the group consisting of metal powder, metal foil, fine metal particles, brightener, lame agent, cut pieces of colored paper, natural gems and artificial gems.

The twenty-sixth aspect of the present invention provides the metal colloid-containing coat formed article of the invention according to the twenty-fifth aspect, wherein the metal used in the metal powder, metal foil or fine metal particles is Au.

The twenty-seventh aspect of the present invention provides a base material with a conductive film, having resistivity of $1\times10^{-3}$ Ω·cm or less, which is obtained by coating, spraying, printing, ejecting or transferring the metal colloid of any one of the thirteenth to fifteenth aspects on a base material, and maintaining the base material with the metal colloid in a predetermined atmosphere at a temperature of 15 to 450° C. for 1 to 60 minutes.

The twenty-eighth aspect of the present invention provides a pen, a brush-pencil, a cartridge for pen and a disposable ampul, each being filled with the metal colloid of any one of the thirteenth to fifteenth aspects as an ink.

The twenty-ninth aspect of the present invention provides a drawn material which is drawn by an ink jet printer using the metal colloid of any one of the thirteenth to fifteenth aspects as an ink.

The thirteenth aspect of the present invention provides a metal colloidal particles capable of forming a metal colloid by dispersing in either or both of an aqueous dispersion medium and a nonaqueous dispersion medium in a predetermined proportion while mixing, comprising metal particles and a protective agent coordination-modified on the surface of the particles, the protective agent having a carbon skeleton containing nitrogen in the molecule, and having a structure of being coordination-modified on the surface of the metal particles using nitrogen or an atomic group including nitrogen as an anchor, wherein the protective agent has one, or two or more functional groups selected from the group consisting of alkoxysilyl group, silanol group and hydroxyalkyl group in a molecular structure, and the metal particles contain an Au component as a main component and also contain one, or two or more metal components other than the Au component as an accessory component.

Since the protective agent is firmly bonded to the surface of metal particles using an atom or an atomic group of either or both of sulfur and oxygen as an anchor, high stability is attained. The alkoxysilyl group, the silanol group and the hydroxyalkyl group contained in the molecular structure of the protective agent have high reactivity and chemically bonded to all base materials. Metal particles are spontaneously self-organized and cause closest packing, and are condensed with a reactive functional group. Therefore, it is considered that a coat obtained by coating or spraying the metal colloid made of the metal colloidal particles according the thirtieth aspect has high strength and is converted into an organic-inorganic hybrid bulk between particles.

When the metal particles constituting the metal colloidal particles are composed of an Au component as a main component and one, or two or more metal components other than the Au component as an accessory component, a coat formed by using a metal colloid obtained by dispersing metal colloidal particles in a dispersion medium shows metal color with color tone which is different from that peculiar to an Au simple substance. By changing the kind or content of metal constituting the accessory component, it is possible to exhibit various gold-based color tones.

The thirty-first aspect of the present invention provides the metal colloidal particles of the invention according to the thirtieth aspect, wherein the accessory component constituting the metal particles contains at least an Ag component and a Cu component, and the content of the accessory component in the metal particles is from 5 to 40% by weight and the content of the Ag component in the accessory component is from 40 to 60% by weight.

In the thirty-first aspect, a coat formed by using a metal colloid obtained by dispersing metal colloidal particles in a dispersion medium shows yellow gold color tone.

The thirty-second aspect of the present invention provides the metal colloidal particles of the invention according to the thirtieth aspect, wherein the accessory component constituting the metal particles contains at least Ag particles and Cu particles, and the content of the accessory component in the metal particles is from 5 to 40% by weight and the content of Ag component in the accessory component is 65% by weight or more.

In the thirty-second aspect, a coat formed by using a metal colloid obtained by dispersing metal colloidal particles in a dispersion medium shows green gold color tone.

The thirty-third aspect of the present invention provides the metal colloidal particles of the invention according to the thirtieth aspect, wherein the accessory component constituting the metal particles contains at least Ag particles and Cu particles, and the content of the accessory component in the metal particles is from 5 to 40% by weight and the content of Ag component in the accessory component is 30% by weight or less.

In the thirty-third aspect, a coat formed by using a metal colloid obtained by dispersing metal colloidal particles in a dispersion medium shows red gold color tone.

The thirty-fourth aspect of the present invention provides the metal colloidal particles of the invention according to the thirtieth aspect, wherein the accessory component constituting metal particles contains at least Ag particles, Cu particles and Pd particles, and the content of the accessory component in the metal particles is from 5 to 40% by weight and the content of the Ag component in the accessory component is 30% by weight or less.

In the thirty-fourth aspect, a coat formed by using a metal colloid obtained by dispersing metal colloidal particles in a dispersion medium shows pink gold color tone.

The thirty-fifth aspect of the present invention provides the metal colloidal particles of the invention according to the thirtieth aspect, wherein the accessory component constituting the metal particles contains at least Pd particles, and the content of the accessory component in the metal particles is from 5 to 40% by weight.

In the thirty-fifth aspect, a coat formed by using a metal colloid obtained by dispersing metal colloidal particles in a dispersion medium shows white gold color tone.

The thirty-sixth aspect of the present invention provides the metal colloidal particles of the according to any one of the thirtieth to thirty-fifth aspect, wherein, by mixing an alkoxysilane having an amino group with a metal compound in a nonaqueous medium and reducing the metal compound in the presence of a reducing agent, a protective agent made of the alkoxysilane is linked to the surface of metal particles using a nitrogen atomic group as an anchor.

The thirty-seventh aspect of the present invention provides the metal colloidal particles of the according to any one of the thirtieth to thirty-sixth aspect, wherein the atomic group including nitrogen is at least one selected from the group consisting of amino group, amide atomic group and imide atomic group.

The thirty-eighth aspect of the present invention provides the metal colloidal particles of the invention according to any one of the thirtieth to thirty-seventh aspects, wherein either of both of the alkoxysilyl group and the hydroxyalkyl group contained in a protective agent is chelete-coordinated by a chelating agent.

The thirty-ninth aspect of the present invention provides a metal colloid which is characterized in that the metal colloidal particles of any one of the thirtieth to thirty-eighth are dispersed in either or both of an aqueous dispersion medium and a nonaqueous dispersion medium in a predetermined proportion.

In the thirty-ninth aspect, metal colloidal particles, when the protective agent is firmly bonded to the surface of metal particles using a nitrogen atom or an atomic group as an anchor, a colloidal solution is extremely stable and a high concentration metal colloid can be obtained. Also less viscosity change and color tone change occur. Furthermore, a thin film having large film strength can be formed.

The fortieth aspect of the present invention provides a metal colloidal thin film which is formed by using the metal colloid of the thirty-ninth aspect.

In the fortieth aspect, the metal colloid-containing coat formed by using the metal colloid of the present invention shows various gold-based color tones.

The forty-first aspect of the present invention provides a metal colloid-containing coat formed article which is formed by coating, spraying, printing, ejecting or transferring the metal colloid of the thirty-ninth aspect on the surface of a base material, and removing the dispersion medium from the metal colloid.

In the forty-first aspect, the metal colloid-containing coat formed by coating the metal colloid of the present invention on the surface of the base material and removing the dispersion medium shows various gold-based color tones.

The forty-second aspect of the present invention provides the metal colloid-containing coat formed article of the invention according to the forty-first aspect, further comprising one, two or more kinds selected from the group consisting of metal powder, metal foil, fine metal particles, brightener, lame agent, cut pieces of colored paper, natural gems and artificial gems.

In the forty-second aspect, decorativeness is enhanced by containing the metal powder in or the surface of the coat.

The forty-third aspect of the present invention provides the metal colloid-containing coat formed article of the invention according to the forty-second aspect, wherein the metal used in the metal powder, metal foil or fine metal particles is Au.

In the forty-third aspect, when Au is used as metal used in the metal powder, metal foil or fine metal particles, high sensuousness is obtained.

The forty-fourth aspect of the present invention provides the metal colloid-containing coat formed article of the invention according to the forty-third aspect, wherein the jewelry is jewelry made of noble metal clay.

The forty-fifth aspect of the present invention provides a transfer sheet comprising a metal colloid-containing coat formed by coating, spraying, printing, ejecting or transferring the metal colloid of the thirty-ninth aspect on a transfer substrate wherein either of both of the surface and the back surface are subjected to a release treatment, and removing the dispersion medium from the metal colloid.

In the forty-fifth aspect, the transfer sheet with a metal colloid-containing coat, which is formed by using the metal colloid of the present invention, can form a transfer film which shows various gold-based color tones.

The forty-sixth aspect of the present invention provides the transfer sheet of the invention according to the forty-fifth aspect, wherein the metal colloid-containing coat contains one, two or more kinds selected from the group consisting of metal powder, metal foil, fine metal particles, brightener, lame agent, cut pieces of colored paper, natural gems and artificial gems.

In the forty-sixth aspect, decorativeness is enhanced by containing the metal powder in the coat.

The forty-seventh aspect of the present invention provides the transfer sheet of the invention according to the forty-sixth aspect, wherein the metal used in the metal powder, metal foil or fine metal particles is Au.

In the forty-seventh aspect, when Au is used as metal used in the metal powder, metal foil or fine metal particles, high sensuousness is obtained.

The forty-eighth aspect of the present invention provides a metal colloid-containing coat formed article comprising a transfer film transferred from the transfer sheet of the forty-sixth or forty-seventh aspect.

In the forty-eighth aspect, the metal colloid-containing coat formed article comprising the transfer film transferred from the transfer sheet on the surface shows various gold-based color tones.

The forty-ninth aspect of the present invention provides the metal colloid-containing coat formed article of the invention according to the forty-eighth aspect, wherein the base material to be transferred is jewelry and the jewelry is jewelry made of a noble metal clay.

The fifty aspect of the present invention provides a pen, a brush-pencil, a cartridge for pen and a disposable ampul, each being filled with the metal colloid of the thirty-ninth aspect as an ink.

The fifty-first aspect of the present invention provides a metal colloid-containing coat formed article wherein a metal colloid-containing coat with optional patterns is formed by drawing through an ink jet printer using the metal colloid of the thirty-ninth aspect as an ink.

The fifty-second aspect of the present invention provides the metal colloid-containing coat formed article of the invention according to the fifty-first aspect, further comprising one, or two or more kinds selected from the group consisting of metal powder, metal foil, fine metal particles, brightener, and lame agent, cut pieces of colored paper, natural gems and artificial gems.

The fifty-third aspect of the present invention provides the metal colloid-containing coat formed article of the invention according to the fifty-first aspect, wherein the metal used in the metal powder, metal foil or fine metal particles is Au.

The fifty-fourth aspect of the present invention provides a metal colloid-containing coat formed article wherein metal colloidal particles comprise metal particles and a protective agent coordination-modified on the surface of the particles, the protective agent having a carbon skeleton containing nitrogen in the molecule, and having a structure of being coordination-modified on the surface of metal particles using nitrogen or an atomic group including nitrogen as an anchor, and the protective agent contains one, or two or more functional groups selected from the group consisting of alkoxysilyl group, silanol group and hydroxyalkyl group in a molecular structure, the metal colloid-containing coat formed article being formed by coating, spraying, printing, ejecting or transferring a metal colloid which is obtained by dispersing in either or both of an aqueous dispersion medium and a nonaqueous dispersion medium in a predetermined proportion while mixing, on the surface of a base material, and removing the dispersion medium from the metal colloid.

The fifty-fifth aspect of the present invention provides the metal colloid-containing coat formed article of the invention according to the fifty-fourth aspect, wherein the base material is jewelry and the jewelry is made of a noble metal clay.

The fifty-sixth aspect of the present invention provides the metal colloid-containing coat formed article of the invention according to the fifty-fourth or fifty-fifth aspect, further comprising one, two or more kinds selected from the group consisting of metal powder, metal foil, fine metal particles, brightener, lame agent, cut pieces of colored paper, natural gems and artificial gems.

The fifty-seventh aspect of the present invention provides the metal colloid-containing coat formed article of the invention according to the fifty-sixth aspect, wherein the metal used in the metal powder, metal foil or fine metal particles is Au.

The fifty-eighth aspect of the present invention provides the metal colloid-containing coat formed article of the invention according to any one of fifty-fourth to fifty-seventh aspects, wherein the metal particles constituting the metal colloidal particles are made of Au and have an average particle size within a range from 1 to 60 nm.

The fifty-ninth aspect of the present invention provides the metal colloid-containing coat formed article of the invention according to any one of fifty-fourth to fifty-eighth aspects, wherein a coat formed by coating, spraying, printing, ejecting or transferring a metal colloid, which is obtained by dispersing metal colloidal particles containing Au colloidal particles as a main component and also containing 0.1 to 10% metal particles having an average particle size of 1 to 10 nm, in addition to the Au colloidal particles, in a dispersion medium, and removing the dispersion medium from the metal colloid, shows a pink gold color tone.

The sixtieth aspect of the present invention provides a transfer sheet wherein metal colloidal particles comprise metal particles and a protective agent coordination-modified on the surface of the particles, the protective agent having a carbon skeleton containing nitrogen in the molecule, and having a structure of being coordination-modified on the surface of metal particles using nitrogen or an atomic group including nitrogen as an anchor, and the protective agent contains one, or two or more functional groups selected from the group consisting of alkoxysilyl group, silanol group and hydroxyalkyl group in a molecular structure, the metal colloid-containing coat formed article having a metal colloid-containing coat formed by coating, spraying, printing, ejecting or transferring a metal colloid which is obtained by dispersing in either or both of an aqueous dispersion medium and a nonaqueous dispersion medium in a predetermined proportion while mixing, on a transfer substrate wherein either of both of the surface and the back surface are subjected to a release treatment, and removing the dispersion medium from the metal colloid.

The sixty-first aspect of the present invention provides the transfer sheet of the invention according to the sixtieth, wherein the metal colloid-containing coat contains one, or two or more kinds selected from the group consisting of metal powder, metal foil, fine metal particles, brightener, lame agent, cut pieces of colored paper, natural gems and artificial gems.

The sixty-second aspect of the present invention provides the transfer sheet of the invention according to the sixty-first aspect, wherein the metal used in the metal powder, metal foil or fine metal particles is Au.

The sixty-third aspect of the present invention provides the transfer sheet of the invention according to any one of the sixtieth to sixty-second aspects, wherein the metal particles constituting the metal colloidal particles are made of Au and have an average particle size within a range from 1 to 60 nm.

The sixty-fourth aspect of the present invention provides the transfer sheet of the invention according to any one of the sixtieth to sixty-third aspects, wherein a coat formed by coating, spraying, printing, ejecting or transferring a metal colloid, which is obtained by dispersing metal colloidal particles containing Au colloidal particles as a main component and also containing 0.1 to 10% metal particles having an average particle size of 1 to 10 nm, in addition to the Au colloidal particles, in a dispersion medium, and removing the dispersion medium from the metal colloid, shows a pink gold color tone.

The sixty-fifth aspect of the present invention provides a metal colloid-containing coat formed article comprising a transfer film transferred from the transfer sheet of any one of the sixtieth to six fourth aspects.

The sixty-sixth aspect of the present invention provides an invention according to the sixty-fifth aspect, wherein the base material is jewelry and the jewelry is made of a noble metal clay.

The sixty-seventh aspect of the present invention provides the metal colloid-containing coat formed article of the invention according to the sixty-fifth or sixty-sixth aspect, further comprising one, two or more kinds selected from the group consisting of metal powder, metal foil, fine metal particles, brightener, lame agent, cut pieces of colored paper, natural gems and artificial gems.

The sixty-eighth aspect of the present invention provides the metal colloid-containing coat formed article of the invention according to the sixty-seventh aspect, wherein the metal used in the metal powder, metal foil or fine metal particles is Au.

The sixty-ninth aspect of the present invention provides a base material with a conductive film, having resistivity of $1\times10^{-3}$ Ω·cm or less wherein metal colloidal particles comprise metal particles and a protective agent coordination-modified on the surface of the particles, the protective agent having a carbon skeleton containing nitrogen in the molecule, and having a structure of being coordination-modified on the surface of metal particles using nitrogen or an atomic group including nitrogen as an anchor, and the protective agent contains one, or two or more functional groups selected from the group consisting of alkoxysilyl group, silanol group and hydroxyalkyl group in a molecular structure, the base material with a conductive film being obtained by coating, spraying, printing, ejecting or transferring a metal colloid which is obtained by dispersing in either or both of an aqueous dispersion medium and a nonaqueous dispersion medium in a predetermined proportion while mixing, on a base material, and maintaining the base material with the metal colloid in a predetermined atmosphere at a temperature of 15 to 450° C. for 1 to 60 minutes.

The seventieth aspect of the present invention provides the base material with a conductive film of the invention according to the sixty-fifth to sixty-sixth aspect, wherein the metal particles constituting the metal colloidal particles are made of Au and have an average particle size within a range from 1 to 60 nm.

The seventy-first aspect of the present invention provides the base material with a conductive film of the invention according to the sixty-ninth or seventieth aspect, wherein a coat formed by coating, spraying, printing, ejecting or transferring a metal colloid, which is obtained by dispersing metal colloidal particles containing Au colloidal particles as a main component and also containing 0.1 to 10% metal particles having an average particle size of 1 to 10 nm, in addition to the Au colloidal particles, in a dispersion medium, and removing the dispersion medium from the metal colloid, shows a pink gold color tone.

The seventy-second aspect of the present invention provides a pen, a brush-pencil, a cartridge for pen and a disposable ampul wherein metal colloidal particles comprise metal particles and a protective agent coordination-modified on the surface of the particles, the protective agent having a carbon skeleton containing nitrogen in the molecule, and having a structure of being coordination-modified on the surface of metal particles using nitrogen or an atomic group including nitrogen as an anchor, and the protective agent contains one, or two or more functional groups selected from the group consisting of alkoxysilyl group, silanol group and hydroxyalkyl group in a molecular structure, the pen, the brush-pencil, the cartridge for pen and the disposable ampul being filled with a metal colloid as an ink obtained by dispersing in either or both of an aqueous dispersion medium and a nonaqueous dispersion medium in a predetermined proportion while mixing.

The seventy-third aspect of the present invention provides the pen, the brush-pencil, the cartridge for pen and the disposable ampul of the invention according to the seventy-second aspect, wherein the metal particles constituting the metal colloidal particles are made of Au and have an average particle size within a range from 1 to 60 nm.

The seventy-fourth aspect of the present invention provides the pen, the brush-pencil, the cartridge for pen and the disposable ampul of the invention according to the sixty-second or sixty-third aspect, wherein a coat formed by coating, spraying, printing, ejecting or transferring a metal colloid, which is obtained by dispersing metal colloidal particles containing Au colloidal particles as a main component and also containing 0.1 to 10% metal particles having an average particle size of 1 to 10 nm, in addition to the Au colloidal particles, in a dispersion medium, and removing the dispersion medium from the metal colloid, shows a pink gold color tone.

The seventy-fifth aspect of the present invention provides a stamp pad and a seal impression pad wherein metal colloidal particles comprise metal particles and a protective agent coordination-modified on the surface of the particles, the protective agent having a carbon skeleton containing nitrogen in the molecule, and having a structure of being coordination-modified on the surface of metal particles using nitrogen or an atomic group including nitrogen as an anchor, and the protective agent contains one, or two or more functional groups selected from the group consisting of alkoxysilyl group, silanol group and hydroxyalkyl group in a molecular structure, the stamp pad and the seal impression pad being impregnated with a metal colloid as an ink obtained by dispersing in either or both of an aqueous dispersion medium and a nonaqueous dispersion medium in a predetermined proportion while mixing.

The seventy-sixth aspect of the present invention provides a drawn material which is drawn by using an ink with which the stamp pad or seal impression pad of the seventy-fifth aspect is impregnated.

The seventy-seventh aspect of the present invention provides a drawn material wherein metal colloidal particles comprise metal particles and a protective agent coordination-modified on the surface of the particles, the protective agent having a carbon skeleton containing nitrogen in the molecule, and having a structure of being coordination-modified on the surface of metal particles using nitrogen or an atomic group including nitrogen as an anchor, and the protective agent contains one, or two or more functional groups selected from the group consisting of alkoxysilyl group, silanol group and hydroxyalkyl group in a molecular structure, the drawn material being drawn by an ink jet printer using, as an ink, a metal colloid obtained by dispersing in either or both of an aqueous dispersion medium and a nonaqueous dispersion medium in a predetermined proportion while mixing.

The seventy-eighth aspect of the present invention provides the drawn material of the invention according to the seventy-seventh aspect, wherein the metal particles constituting the metal colloidal particles are made of Au and have an average particle size within a range from 1 to 60 nm.

The seventy-ninth aspect of the present invention provides the drawn material of the invention according to the seventy-seventh or seventy-eighth aspect, wherein a coat formed by coating, spraying, printing, ejecting or transferring a metal colloid, which is obtained by dispersing metal colloidal particles containing Au colloidal particles as a main component and also containing 0.1 to 10% metal particles having an average particle size of 1 to 10 nm, in addition to the Au colloidal particles, in a dispersion medium, and removing the dispersion medium from the metal colloid, shows a pink gold color tone.

The metal colloidal particles of the present invention are characterized by metal colloidal particles capable of forming a metal colloid by dispersing in either or both of an aqueous dispersion medium and a nonaqueous dispersion medium in a predetermined proportion while mixing, comprising metal particles and a protective agent coordination-modified on the surface of the particles, the protective agent having a carbon skeleton containing either or both of sulfur and oxygen in the molecule, and having a structure of being coordination-modified on the surface of metal particles using an atom or an atomic group of either or both of sulfur and oxygen as an anchor, wherein the protective agent contains one, or two or more functional groups selected from the group consisting of alkoxysilyl group, silanol group and hydroxyalkyl group in a molecular structure. The metal colloid of the present invention is characterized in that the metal colloidal particles are dispersed in either or both of an aqueous dispersion medium and a nonaqueous dispersion medium in a predetermined proportion while mixing, or the metal colloidal particles of the present invention are mixed with a sol-gel solution in a predetermined proportion. Since the protective agent is firmly bonded to the surface of metal particles using an atom or an atomic group of either or both of sulfur and oxygen as an anchor, and is preferably firmly bonded to the surface of metal particles even in case of using a nitrogen atom or an atomic group as an anchor, a colloidal solution is extremely stable and a high concentration metal colloid can be obtained. Also less viscosity change and color tone change occur. Furthermore, a thin film having large film strength can be formed. Therefore, the thin film using the metal colloid of the present invention is suited for used as optical materials such as color filter and display panel. Also it is possible to obtain a transfer sheet and a low-resistance base material with a conductive film, each being made of the metal colloid of the present invention. Furthermore, the metal colloidal particles of the present invention is suited for use as a pen, a brush-pencil, a cartridge for pen and a disposable ampul, each containing the metal colloid of the present invention as an ink; a stamp pad and a seal impression pad, each being impregnated with the metal colloid of the present invention as an ink; and an ink jet printer using the metal colloid of the present invention as an ink.

In the metal colloidal particles of the present invention, since the protective agent constituting the metal colloidal particles is firmly bonded to the surface of metal particles using a nitrogen atom or an atomic group as an anchor, high stability is attained. The alkoxysilyl group, the silanol group and the hydroxyalkyl group contained in the molecular structure of the protective agent have high reactivity and chemically bonded to all base materials. Metal particles are spontaneously self-organized and cause closest packing, and are condensed with a reactive functional group. Therefore, it is considered that a coat obtained by coating or spraying the metal colloid made of the metal colloidal particles of the present invention has high strength and is converted into an organic-inorganic hybrid bulk between particles. When the metal particles constituting the metal colloidal particles are composed of an Au component as a main component and one, or two or more metal components other than the Au component as an accessory component, a coat, which is formed by coating, spraying, printing, ejecting or transferring a metal colloid obtained by dispersing the metal colloidal particles in a dispersion medium, and removing the dispersion medium from the metal colloid, shows metal color with color tone which is different from that peculiar to an Au simple substance. By changing the kind or content of metal constituting the accessory component, it is possible to exhibit various gold-based color tones.

The metal colloid of the present invention is characterized in that the metal colloidal particles of the present invention are dispersed in either or both of an aqueous dispersion medium and a nonaqueous dispersion medium in a predetermined proportion while mixing. Since the protective agent constituting the metal colloidal particles is firmly bonded to the surface of metal particles using a nitrogen atom or an atomic group as an anchor, a colloidal solution is extremely stable and a high concentration metal colloid can be obtained. Also less viscosity change and color tone change occur. Furthermore, a thin film having large film strength can be formed. Furthermore, the transfer sheet comprising a metal colloid-containing coat formed using the metal colloid of the present invention can form a transfer film which shows various gold-based color tones. Furthermore, it is suited for use as a pen, a brush-pencil, a cartridge for pen and a disposable ampul, each containing the metal colloid of the present invention as an ink; a stamp pad and a seal impression pad, each being impregnated with the metal colloid of the present invention as an ink; and an ink jet printer using the metal colloid of the present invention as an ink.

The metal colloid-containing coat formed article and the transfer sheet of the present invention have a metal specular glossy area with various color tones and also have a metal colloid-containing coat wherein a coat having excellent heat resistance is formed.

The base material with a conductive film of the present invention has a metal specular glossy area with various color tones and has excellent heat resistance, and also enable the formation of a low-resistance conductive film.

Furthermore, the pen, the brush-pencil, the cartridge for pen, the disposable ampul, the stamp pad and the seal impression pad of the present invention are excellent in quality-retaining property of the metal colloid filled or impregnated. The drawn material obtained by using them has color tone and metal gloss peculiar to metal.

BRIEF DESCRIPTION OF THE DRAWINGS

FIG. 10 B is a photograph showing a picture frame, the frame portion of which is coated with a metal colloid of Example 7.

FIG. 11 B is a photograph showing an earring, the surface of which is coated with a metal colloid of Example 8.

FIG. 11 C is a photograph showing a broach, the surface of which is coated with a metal colloid of Example 8.

FIG. 17 B is a photograph showing artificial nails of Example 17 wherein a metal colloid-containing coat showing a green gold color tone on the surface is formed.

FIG. 17 C is a photograph showing artificial nails of Example 18 wherein a metal colloid-containing coat showing a red gold color tone on the surface is formed.

FIG. 18 B is a photograph showing artificial nails of Example 23 wherein a metal colloid-containing coat, a gold foil powder and natural gems of diamond and pink sapphire are formed in combination on the surface.

FIG. 20 B is a sectional view showing a pen connected with a cartridge for pen of Example 38.

FIG. 26 B is a photograph of a doll, the surface of which is coated with a metal colloid.

FIG. 27 B is a photograph showing a pierced earring, the surface of which is coated with a metal colloid.

FIG. 27 C is a photograph showing a watch, the surface of which is coated with a metal colloid.

FIG. 32 B is a photograph showing a memorial card provided with patterns using seal impression pad of FIG. 32 A.

FIG. 33 B is a photograph showing a mortuary tablet wherein metal colloid-containing coat is formed by drawing a picture using an ink jet printer apparatus of Example 95.

DETAILED DESCRIPTION OF THE INVENTION

The metal colloidal particles of the present invention are characterized by metal colloidal particles capable of forming a metal colloid by dispersing in either or both of an aqueous dispersion medium and a nonaqueous dispersion medium in a predetermined proportion while mixing, comprising metal particles and a protective agent coordination-modified on the surface of the particles, the protective agent having a carbon skeleton containing either or both of sulfur and oxygen in the molecule, and having a structure of being coordination-modified on the surface of metal particles using an atom or an atomic group of either or both of sulfur and oxygen as an anchor, wherein the protective agent contains one, or two or more functional groups selected from the group consisting of alkoxysilyl group, silanol group and hydroxyalkyl group in a molecular structure. Since the protective agent is firmly bonded to the surface of metal particles using an atom or an atomic group of either or both of sulfur and oxygen as an anchor, high stability is attained. The alkoxysilyl group, the silanol group and the hydroxyalkyl group contained in the molecular structure of the protective agent have high reactivity and chemically bonded to all base materials. Metal particles are spontaneously self-organized and cause closest packing, and are condensed with a reactive functional group. Therefore, it is considered that a coat obtained by coating or spraying the metal colloid made of the metal colloidal particles of the present invention has high strength and is converted into an organic-inorganic hybrid bulk between particles.

Figure 1:
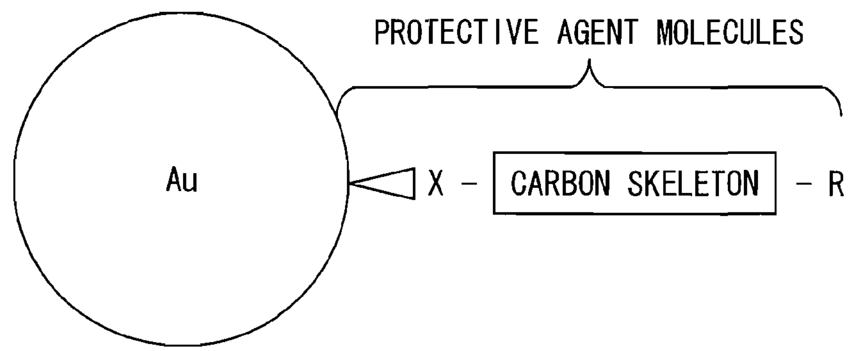
FIG. 1 is a schematic view showing metal colloidal particles of the present invention.

As shown in FIG. 1, since one end of the protective agent is bonded to the surface of metal particles (Au particles in FIG. 1) using a protective agent coordination-modified site represented by X as an anchor, the protective agent is firmly bonded to the surface of metal particles and thus a metal colloidal solution having good stability is obtained. Since the protective agent end site represented by R located at the other end of the protective agent constitutes the outermost surface of the colloid and this protective agent end site is provided with a functional group with high reactivity, adhesion with the base material is excellent. The fact that the protective agent is bonded to the surface of metal particles using the protective agent coordination-modified site represented by X can be confirmed by analytical means, for example, NMR, GPC, TG-DTA, FT-IR, XPS, TOF-SIMS, Small Angle X-ray Scattering (SAXS), visible ultraviolet spectroscopy, Surface Enhanced Raman Scattering (SERS) or X-ray Absorption Fine Structure (XAFS). Using the above analytical means, it is possible to confirm by what element or atomic group the protective agent is anchored.

In the metal colloidal particles of the present invention, it is preferred that the protective agent further contains nitrogen and has a structure of being coordination-modified on the surface of metal particles using nitrogen or an atomic group including nitrogen as an anchor. Consequently, a coordination-modifying force increases and the number of points at witch the protective agent is coordinated increases, and thus stability with time of the metal colloid is extremely improved.

Oxygen contained in the protective agent is derived from at least one selected from the group consisting of carbonyl group, carboxyl group, aldehyde group, amide group and sulfonyl group. The atomic group including nitrogen in the protective agent include at least one selected from the group consisting of amino group, amide atomic group and imide atomic group.

The method of producing metal colloidal particles of the present invention is not limited. The method may be a method by which the above bonded structure to metal colloidal particles is obtained. An example of a specific method is as follows. In a nonaqueous system, an alkoxysilane having a thiol group is mixed with a metal compound and the metal compound is reduced in the presence of a reducing agent to obtain metal colloidal particles wherein the protective agent comprising the alkoxysilane is bonded to the surface of metal particles using the alkoxysilane having a thiol group as an anchor.

Metal colloidal particles are produced by the reductive reaction of the nonaqueous system in the presence of the alkoxysilane having a thiol group. The nonaqueous system means that metal reduction of the metal compound is conducted in an organic solution of a thio group-containing alkoxysilane or an alcohol without conducting metal reduction in an aqueous solution of the metal compound. In the method of bonding the thio group-containing alkoxysilane after producing metal colloidal particles by the reductive reaction in the aqueous solution like a conventional method, since the alkoxysilane is exposed in water, the substitution reaction may not proceed by the influence of the hydrolysis. If the substitution reaction proceeds, stability is impaired by the following hydrolysis and thus it is difficult to obtain metal colloidal particles of the present invention.

Metal colloidal particles wherein either or both of an alkoxysilyl group and a hydroxyalkyl group are chelete-coordinated by using a chelating agent such as β diketon have the effect of delaying the hydrolysis reaction and stability is enhanced furthermore.

The alkoxysilane preferably has one or two amino groups and also has an organic chain (—$CH_2$—) n wherein n is 1 to 3. When the alkoxysilane has three or more amino groups, the organic chain is lengthened. As a result, not only color stability deteriorates after firing, but also it becomes difficult to synthesize and it is expensive. When n of the organic chain is 3 or more, the organic chain is lengthened and stability deteriorates.

Specific examples of the alkoxysilane having an amino group used in the present invention include γ-aminopropyltrimethoxysilane, γ-aminopropyltriethoxysilane, N-β(aminoethyl)γ-aminopropylmethyldimethoxysilane, N-β(aminoethyl)γ-aminopropyltrimethoxysilane and N-β(aminoethyl)γ-aminopropyltriethoxysilane. A molar ratio of amount of these protective agents (amino group-containing alkoxysilane) to the amount of metal may be from 2 to 40.

Examples of the metal of metal particles include one, or two or more kinds selected from the group consisting of Au, Ag, Pt, Cu, Pd, Ni, Zn, Ru, Rh and Ir. As the metal compound used to produce these metal particles, for example, there can be used metal salts such as chlorauric acid, gold potassium cyanide, silver chloride, silver nitride, silver sulfide, silver cyanide, chloroplatinic acid, tetrachlorohexaamine platinum, palladium nitrate, palladium chloride, chloroiridic acid, iridium chloride, ruthenium chloride, ruthenium nitrate, rhodium chloride, rhodium nitrate, nickel sulfate, nickel chloride, copper acetate and zinc chloride.

As the reducing agent, for example, there can be used sodium borohydride, trimethylamineborane, dimethylamineborane, tertiary butylamineborane, secondary amine, tertiary aminehypophosphite, glycerin, alcohol, hydrogen peroxide, hydrazine, hydrazine sulfate, aqueous formaldehyde solution, tartrate, glucose, sodium N—N-diethylglycine, sodium sulfite, sulfurous acid gas and ferrous sulfate.

The average particle size of metal particles constituting metal colloidal particles is within a range from 1 to 100 nm, and preferably from 1 to 80 nm. When the metal particles constituting metal colloidal particles contain Au as a main component, the average particle size of Au particles is preferably within a range from 1 to 60 nm. The metal colloidal particles are granular particles having a spherical, multiangular or ameboid shape.

In the metal colloidal particles of the present invention, since the protective agent is bonded to the surface of metal particles using an atom or an atomic group of either or both of sulfur and oxygen as an anchor, the metal colloidal solution is stable. For example, as shown in Examples described hereinafter, the viscosity within 80 days is from 25 to 30 cP and viscosity change (viscosity with time within 80 days/initial viscosity) is 1.5 or less (1.25 to 1.50 in Examples) relative to the initial viscosity of 20 cP.

Furthermore, according to the present invention, a high concentration metal colloid can be obtained. The concentration of the metal colloid obtained by a conventional method is approximately 1% by weight or less. In the present invention, a metal colloid having a concentration of 10% by weight or more can be obtained. Moreover, in such a high concentration metal colloid, the colloidal solution is stable and, as described above, viscosity change is small. For example, in case of a metal colloid of gold, the gold concentration is stable within a range from 0.1 to 95% by weight and an organic solvent or water can be used as a dispersion medium. The concentration of gold in the metal colloid is more preferably within a range from 10 to 60% by weight.

The metal colloid of the present invention and the thin film obtained from the metal colloid have excellent heat resistance. Specifically, change of color tone is 2% or less even when maintained at a heating base temperature, for example, from about 300 to 400° C. for 400 hours, and color tone scarcely changes. In Examples described hereinafter, the metal colloid as a binder was added to a silica sol and a film was formed on a glass substrate by spin coating, and then permeability was measured at 300° C. As a result, change was scarcely recognized.

The metal colloidal particles of the present invention having a particle size of 0.1 to 60 nm are excellent in stability. When the particle size is more than 60 nm, there arises a phenomenon wherein sedimentation naturally occurs due to dead weight. When the particle size is less than 0.1 nm, the color developing effect is lowered.

When the metal particles contain Au particles as a main component, the metal colloidal particles of the present invention show glossy color tone peculiar to Au particles. A coat formed by coating or spraying a metal colloid, which is obtained by dispersing metal colloidal particles containing Au colloidal particles as a main component and also containing 0.1 to 10% metal particles having an average particle size of 1 to 10 nm, in addition to the Au colloidal particles, in a dispersion medium, and removing the dispersion medium from the metal colloid, shows a pink gold color tone.

In the metal colloidal particles which are either or both of metal colloidal particles containing Au colloidal particles as a main component and also containing Ag particles and Cu particles as impurities, in addition to Au particles, and metal colloidal particles containing metal particles made of an alloy containing Au as a main component and also containing Ag and Cu as impurities, wherein when the content of impurities in the metal colloidal particles is from 5 to 40% and the content of Ag in impurities is from 40 to 60% by weight based on 100% by weight of impurities, a coat formed by coating or spraying a metal colloid, which is obtained by dispersing the metal colloidal particles in a dispersion medium, and removing the dispersion medium from the metal colloid, shows a yellow gold color tone.

Although the metal colloidal particles show yellow gold color tone, metal colloidal particles, which contain Au as a main component and also contain metal particles made of an alloy containing Ag and Cu as impurities, can also the same yellow gold color tone. By using metal colloidal particles obtained by mixing metal colloidal particles containing Au particles as a main component and also containing Ag particles and Cu particles as impurities, in addition to Au particles, with metal colloidal particles containing metal particles made of the above alloy, the same yellow gold color tone can be shown.

The above color tone can be identified by CIE 1976 L*a*b* color space (light source for measurement C: color temperature: 6774K). In case of yellow gold color tone of the present invention, psychometric lightness value L* in CIE 1976 L*a*b* color space is from 25 to 99, chromaticness indices value a* and value b* are from +0.1 to +10 and from +20 to +60, respectively. CIE 1976 L*a*b* color space refers to color space defined by Commission Internationale de l'Eclairage (CIE) on 1976 so that a fixed distance in the color system has the difference, which is perceptually equirate, within any color range by converting CIE XYZ color system. Sychometric lightness value L*, chromaticness indices value a* and value b* are determined by the rectangular coordinate system in the CIE 1976 L*a*b* color space and are represented by the following equations (1) to (3):

$$L^* = 116(Y/Y_0)^{1/3} - 16 \quad (1)$$

$$a^* = 500[(X/X_0)^{1/3} - (Y/Y_0)^{1/3}] \quad (2)$$

$$b^* = 200[(Y/Y_0)^{1/3} - (Z/Z_0)^{1/3}] \quad (3)$$

where $X/X_0$, $Y_0$, and $Z/Z_0 > 0.008856$, X, Y and Z each represents tristimulus value of the object color, and $X_0$, $Y_0$, and $Z_0$ each represents a tristimulus value of a light source for lighting the object color and $Y_0$ is standardized to 100.

In the metal colloidal particles which are either or both of metal colloidal particles containing Au colloidal particles as a main component and also containing Ag particles and Cu particles as impurities, in addition to Au particles, or metal colloidal particles containing metal particles made of an alloy containing Au as a main component and also containing Ag and Cu as impurities, wherein when the content of impurities in the metal colloidal particles is from 5 to 40% and the content of Ag in impurities is 65% by weight or more based on 100% by weight of impurities, a coat formed by coating or spraying a metal colloid, which is obtained by dispersing the metal colloidal particles in a dispersion medium, and removing the coated or sprayed dispersion medium from the metal colloid, shows a green gold color tone. In the green gold color tone of the present invention, the psychometric lightness value L* in the CIE 1976 L*a*b* color space is from 25 to 99, and chromaticness indices value a* and value b* are from −0.1 to −40 and from +0.1 to +60, respectively.

In the metal colloidal particles which are either or both of metal colloidal particles containing Au colloidal particles as a main component and also containing Ag particles and Cu particles as impurities, in addition to Au particles, or metal colloidal particles containing metal particles made of an alloy containing Au as a main component and also containing Ag or Cu as impurities, wherein when the content of impurities in the metal colloidal particles is from 5 to 40% and the content of Ag in impurities is 30% by weight or less based on 100% by weight of impurities, a coat formed by coating or spraying a metal colloid, which is obtained by dispersing the metal colloidal particles in a dispersion medium, and removing the coated or sprayed dispersion medium from the metal colloid, shows a red gold color tone. In the red gold color tone of the present invention, the psychometric lightness value L* in the CIE 1976 L*a*b* color space is from 25 to 99, and chromaticness indices value a* and value b* are from +25 to +50 and from +0.1 to +60, respectively.

In the metal colloidal particles which are either or both of metal colloidal particles containing Au colloidal particles as a main component and also containing Ag particles, Cu particles and Pd particles as impurities, in addition to Au particles, or metal colloidal particles containing metal particles made of an alloy containing Au as a main component and also containing Ag, Cu and Pd as impurities, wherein when the content of impurities in the metal colloidal particles is from 5 to 40% and the Ag content is 30% by weight or less based on 100% by weight of impurities, a coat formed by coating or spraying a metal colloid, which is obtained by dispersing the metal colloidal particles in a dispersion medium, and removing the coated or sprayed dispersion medium from the metal colloid, shows a pink gold color tone. In the pink gold color tone of the present invention, the psychometric lightness value L* in the CIE 1976 L*a*b* color space is from 25 to 99, and chromaticness indices value a* and value b* are from +10 to +25 and from +0.1 to +60, respectively.

In the metal colloidal particles which are either or both of metal colloidal particles containing Au colloidal particles as a main component and also containing Pd particles as impurities, in addition to Au particles, or metal colloidal particles containing metal particles made of an alloy containing Au as a main component and also containing Pd as impurities, wherein when the content of impurities in the metal colloidal particles is from 5 to 40%, a coat formed by coating or spraying a metal colloid, which is obtained by dispersing the metal colloidal particles in a dispersion medium, and removing the coated or sprayed dispersion medium from the metal colloid, shows a white gold color tone. In the white gold color tone of the present invention, the psychometric lightness value L* in the CIE 1976 L*a*b* color space is from 25 to 99, and chromaticness indices value a* and value b* are from +0.1 to +10 and from +0.1 to +20, respectively.

The metal colloid of the present invention is characterized in that the above metal colloidal particles of the present invention are dispersed in an aqueous or nonaqueous solvent in a predetermined proportion while mixing, or the metal colloidal particles of the present invention are mixed with a sol-gel solution in a predetermined proportion. The solvent may be aqueous or nonaqueous and the mixing proportion can also be optionally adjusted. As the sol-gel solution, for example, there can be used a solution for forming at least one compound selected from the group consisting of silica, titania, zirconia, alumina, tantalum oxide and niobium oxide. By using these binders, the metal can be uniformly dispersed in the binder and desired characteristics can be effectively utilized. For example, in the gold colloid, a red color filter utilizing absorption at approximately 510 nm can be realized by uniform dispersion. When the binder has heat resistance, the effect is further enhanced.

The metal colloid thin film of the present invention can be formed using the metal colloid, but the method of forming a film is not specifically limited. For example, the thin film may be formed by coating, spraying, printing, ejecting or transferring a solution, which is prepared by dispersing the metal colloidal particles in an organic solvent, or a solution prepared by mixing with a sol-gel solution, on the surface of a base material, followed by drying, or coating, spraying, printing, ejecting or transferring the solution, followed by drying and further firing. A metal colloid-containing coat formed article can be obtained by coating, spraying, printing, ejecting or transferring the metal colloid of the present invention on a base material and removing the dispersion medium from the metal colloid. Examples of the base material include materials selected from the group consisting of glass, plastic, metal, lumber, ceramic including tile, cement, concrete, stone, fiber, paper and leather. Specific examples of the base material include materials selected from the group consisting of artificial nail, natural hair, artificial hair, jewelries, plastic model, small bag for amulet case and skippet, card for business card, memorial card, invitation card and greeting card, colored paper, doll, deity and Buddhist image, mortuary tablet, clothes, woven fabric and picture frame. Deity and Buddhist image as used herein refers to an image relating to any religion existing in the world and is not limited to denomination of the religion. When the base material is jewelry, this jewelry may be made of a noble metal clay.

It is preferred that the metal colloid-containing coat formed article of the present invention further contains one, or two or more kinds selected from the group consisting of metal powder, metal foil, fine metal particles, brightener, lame agent, cut pieces of colored paper, natural gems and artificial gems. When the coat contains the above metal powder, decorativeness is enhanced. High sensuousness is obtained by using Au as metal used in the metal powder, metal foil or fine metal particles.

A transparent material comprising the metal colloid of the present inventional thin film on the surface of the base material may be used. For example, the metal colloid of the present invention can be used as a metal pigment which is used in applications such as calligraphy, ceramic art, glass blowing, religion and family's Buddhist altar. Also the metal colloid may be used after filling water based and oil based ball-point pens with the metal colloid as an ink. The metal colloid can also be used as a pen ink solution for penwriting brush, fountain pen or marker, and a brush-pencil and a cartridge for pen and disposable ampul. Particularly in a pen filled with the metal colloid as the ink, it is not necessary to transfer the ink to a container and it is very advantageous to easily draw characters or patterns of the metal colloid. The disposable ampul refers to a disposal container made of a synthetic resin wherein a metal colloid is sealed by filling a metal colloid and thermally bond-contacting the upper of the container, sealing of the metal colloid can be easily broken by rotating the lid portion in the lateral direction and can be used as an ink comprising the metal colloid after transferring to any container. When a small amount of the metal colloid is stored using the disposable ampul, since sealing of a required amount of the metal colloid may be broken in case of using, expensive metal colloid hardly deteriorates. Therefore, it is very effective. The type and form of the pen, the cartridge for pen and the disposable ampul are not limited. The metal colloid can also be used as an ink for printing on a paper or a film. The metal colloid can also be used as cosmetic decoration such as nail art. Furthermore, it can also be used as a coating material for forming a wiring material. Examples of the printing method, include, but are not limited to lithographic printing, gravure printing, offset printing, carton printing, metal printing, form printing, duplex printing, over printing, ink jet printing, screen printing, slit coating method, dispenser method, spin coating method, spraying method, dipping method and airbrushing method.

Since the thin film made of the metal colloid has color tone and high transparency according to colloidal particles, a transparent material with this thin film formed thereon can be used as a color filter and a plasma display panel (PDP).

It can also be used as a transfer sheet with a metal colloid-containing coat, which is formed by coating, spraying, printing, ejecting or transferring the metal colloid of the present invention on a transfer substrate wherein either or both of the surface and the back surface are subjected to a release treatment, and removing the dispersion medium from the metal colloid. The transfer sheet of the present invention preferably contains or two or more kinds selected from the group consisting of metal powder, metal foil, fine metal particles, brightener, lame agent, cut pieces of colored paper, natural gems and artificial gems in the metal colloid-containing coat. Decorativeness is enhanced by containing the metal powder in the coat. High sensuousness is obtained by using Au as metal used in the metal powder, metal foil or fine metal particles.

By transferring the metal colloid-containing coat of the transfer sheet of the present invention to the surface of the base material, a metal colloid-containing coat formed article with a transfer film formed on the surface can be obtained. Examples of the base material to which the coat is transferred include materials selected from the group consisting of glass, plastic, metal, lumber, ceramic including tile, cement, concrete, stone, fiber, paper and leather. Specific examples of the base material include materials selected from the group consisting of artificial nail, natural hair, artificial hair, jewelries, plastic model, small bag for amulet case and skippet, card for business card and memorial card, colored paper, doll, deity and Buddhist image, mortuary tablet, clothes, woven fabric and picture frame. Deity and Buddhist image as used herein refers to an image relating to any religion existing in the world and is not limited to denomination of the religion. When the base material is jewelry, this jewelry may be made of a noble metal clay. It is preferred that the base material to which the coat is transferred further contains one, or two or more kinds selected from the group consisting of metal powder, metal foil, fine metal particles, brightener, lame agent, cut pieces of colored paper, natural gems and artificial gems. When the base material contains the above metal powder, decorativeness is enhanced. High sensuousness is obtained by using Au as metal used in the metal powder, metal foil or fine metal particles.

Furthermore, a base material with a low-resistance conductive film having resistivity of $1\times10^{-3}$ Ω·cm or less can be obtained by coating, spraying, printing, ejecting or transferring the metal colloid of the present invention on a base material and maintaining the base material with the metal colloid in a predetermined atmosphere at a temperature of 15 to 450° C. for 1 to 60 minutes. Regarding the conditions for forming a conductive film, it is preferred to maintain at a temperature within a range from 15 to 350° C. for 30 to 60 minutes. When the retention time is less than 30 minutes at the temperature within the above range, desired conductivity may not be exhibited because of insufficient decomposition or elimination of the solvent or the protective agent. Even when the retention time exceeds 60 minutes, resistivity of the resulting conductive film does not change remarkably, excess retention time is not preferred in view of productivity and cost. When the temperature is within a range from 350 to 450° C., it is preferable to maintain for 1 to 60 minutes. When the retention time is less than one minute at the temperature within the above range, desired conductivity may not be exhibited because of insufficient decomposition or elimination of the solvent or the protective agent, or insufficient sintering. Even when the retention time exceeds 60 minutes, resistivity of the resulting conductive film does not change remarkably, excess retention time is not preferred in view of productivity and cost.

Also it is possible to produce a stamp pad and a seal impression pad, impregnated with the metal colloid of the present invention as an ink. Furthermore, it can also be used as a drawn material drawn by using an ink with which the stamp pad or seal impression pad is impregnated, or a drawn material drawn by an ink jet printer using the metal colloid of the present invention as an ink.

The second best mode for carrying out the present invention will now be described.

The metal colloidal particles of the present invention are characterized by metal colloidal particles capable of forming a metal colloid by dispersing in either or both of an aqueous dispersion medium and a nonaqueous dispersion medium in a predetermined proportion while mixing, comprising metal particles and a protective agent coordination-modified on the surface of the particles, the protective agent having a carbon skeleton containing nitrogen in the molecule, and having a structure of being coordination-modified on the surface of metal particles using nitrogen or an atomic group including nitrogen as an anchor, wherein the protective agent contains one, or two or more functional groups selected from the group consisting of alkoxysilyl group, silanol group and hydroxyalkyl group in a molecular structure, and the metal particles contain an Au component as a main component and also contain one, or two or more metal components other than the Au component as an accessory component.

Since the protective agent constituting metal colloidal particles in the metal colloid, which constitutes the coat, has a carbon skeleton containing nitrogen in the molecule, and having a structure of being firmly coordination-modified on the surface of metal particles using nitrogen or an atomic group including nitrogen as an anchor, the metal colloid obtained by the metal colloidal particles in a dispersion medium shows extremely high stability. As a result, a high concentration metal colloid can be obtained and also less viscosity change and color tone change occur. The alkoxysilyl group, the silanol group and the hydroxyalkyl group contained in the molecular structure of the protective agent have high reactivity and chemically bonded to all base materials. Metal particles are spontaneously self-organized and cause closest packing, and are condensed with a reactive functional group. Therefore, it is considered that a metal colloid-containing coat made of the metal colloid having these characteristics of the present invention is converted into an organic-inorganic hybrid bulk between particles, and therefore has comparatively high film strength as compared with a metal colloid-containing coat formed by using a metal colloid comprising a nonreactive protective agent or a metal colloid comprising a protective agent having low reactivity.

Since the protective agent is firmly bonded to the surface of metal particles by bonding one end of the protective agent is bonded to the surface of metal particles using a protective agent coordination-modified site as an anchor, metal colloid having good stability is obtained. Since the protective agent end site located at the other end of the protective agent constitutes the outermost surface of the colloid and this protective agent end site is provided with one, or two or more functional groups with high reactivity selected from the group consisting of alkoxysilyl group, silanol group and hydroxyalkyl group, adhesion with the base material is excellent. The fact that the protective agent is bonded to the surface of metal particles using the protective agent coordination-modified site can be confirmed by analytical means, for example, NMR, GPC, TG-DTA, FT-IR, XPS, TOF-SIMS, SAXS, visible ultraviolet spectroscopy, SERS or XAFS. Using the above analytical means, it is possible to confirm by what element or atomic group the protective agent is anchored.

In metal colloidal particles of the present invention, when metal particles contain an Au component as a main component and also contains one, or two or more metal components different from the Au component as an accessory component, a coat formed by using a metal colloid prepared by dispersing the metal colloidal particles in a dispersion medium shows metal color which is different from that peculiar to an Au simple substance. By changing the kind or proportion of the metal constituting the accessory component, various gold-based color tones can be exhibited. In the metal colloidal particles showing various gold-based color tones, (1) metal particles may be made of an alloy containing Au as a main component and also containing Ag and Cu as an accessory component, or metal particles may be made of (2) a mixture obtained by mixing Au particles as a main component with Ag particles and Cu particles as an accessory component, in addition to Au particles, or (3) metal particles may be made by appropriately using (1) and (2) in combination.

In the metal colloidal particles of the present invention, it is preferred that the accessory component constituting metal particles contains at least both Ag particles and Cu particles and the content of the accessory component in metal particles is from 5 to 40% by weight, and the content of Ag component in the accessory component is from 40 to 60% by weight. A coat formed by using a metal colloid obtained by dispersing the resulting metal colloidal particles in a dispersion medium shows a yellow gold color tone.

The above color tone can be identified by CIE 1976 L*a*b* color space (light source for measurement C: color temperature: 6774K). In case of the yellow gold color tone shown with the above constitution, psychometric lightness value L* in CIE 1976 L*a*b* color space is from 25 to 99, chromaticness indices value a* and value b* are from +0.1 to +10 and from +20 to +60, respectively.

In the metal colloidal particles of the present invention, it is preferred that the accessory component constituting metal particles contains at least both a Ag particles and Cu particles and the content of the accessory component in metal particles is from 5 to 40% by weight, and the content of Ag component in the accessory component is 65% by weight or more. A coat formed by using a metal colloid obtained by dispersing the resulting metal colloidal particles in a dispersion medium shows a green gold color tone. In case of the green gold color tone shown with the above constitution, psychometric lightness value L* in CIE 1976 L*a*b* color space is from 25 to 99, chromaticness indices value a* and value b* are from −0.1 to −40 and from +0.1 to +60, respectively.

In the metal colloidal particles of the present invention, it is preferred that the accessory component constituting metal particles contains at least both Ag particles and Cu particles and the content of the accessory component in metal particles is from 5 to 40% by weight, and the content of Ag component in the accessory component is 30% by weight or less. A coat formed by using a metal colloid obtained by dispersing the resulting metal colloidal particles in a dispersion medium shows a red gold color tone. In case of the green gold color tone shown with the above constitution, psychometric lightness value L* in CIE 1976 L*a*b* color space is from 25 to 99, chromaticness indices value a* and value b* are from +25 to +50 and from +0.1 to +60, respectively.

In the metal colloidal particles of the present invention, it is preferred that the accessory component constituting metal particles contains at least Ag particles, Cu particles and Pd particles and the content of the accessory component in metal particles is from 5 to 40% by weight, and the content of Ag component in the accessory component is 30% by weight or less. A coat formed by using a metal colloid obtained by dispersing the resulting metal colloidal particles in a dispersion medium shows a pink gold color tone. In case of the pink gold color tone shown with the above constitution, psychometric lightness value L* in CIE 1976 L*a*b* color space is from 25 to 99, chromaticness indices value a* and value b* are from +10 to +25 and from +0.1 to +60, respectively.

In the metal colloidal particles of the present invention, it is preferred that the accessory component constituting metal particles contains at least Pd particles and the content of the accessory component in metal particles is from 5 to 40% by weight. A coat formed by using a metal colloid obtained by dispersing the resulting metal colloidal particles in a dispersion medium shows a white gold color tone. In case of the pink gold color tone shown with the above constitution, psychometric lightness value L* in CIE 1976 L*a*b* color space is from 25 to 99, chromaticness indices value a* and value b* are from +0.1 to +10 and from +0.1 to +20, respectively.

The method of producing metal colloidal particles of the present invention is not limited. The method may be a method by which the above bonded structure to metal colloidal particles is obtained. An example of a specific method is as follows. In a nonaqueous system, an alkoxysilane having an amino group is mixed with a metal compound and the metal compound is reduced in the presence of a reducing agent to obtain metal colloidal particles wherein the protective agent comprising the alkoxysilane is bonded to the surface of metal particles using a nitrogen atomic group of the alkoxysilane as an anchor. The nonaqueous system means that metal reduction of the metal compound is conducted in an organic solution of an amino group-containing alkoxysilane or an alcohol without conducting metal reduction in an aqueous solution of the metal compound. In the method of bonding the amino group-containing alkoxysilane after producing metal colloidal particles by the reductive reaction in the aqueous solution like a conventional method, since the alkoxysilane is exposed in water, the substitution reaction may not proceed by the influence of the hydrolysis. If the substitution reaction proceeds, stability is impaired by the following hydrolysis and thus it is difficult to obtain metal colloidal particles of the present invention. The atomic group including nitrogen in the protective agent constituting the metal colloidal particles of the present invention includes at least one selected from the group consisting of amino group, amide atomic group and imide atomic group.

Metal colloidal particles wherein an alkoxysilyl group is chelete-coordinated by using a chelating agent such as β diketon have the effect of delaying the hydrolysis reaction and stability is enhanced furthermore. The alkoxysilane preferably has one or two amino groups and also has an organic chain (—$CH_2$—) n wherein n is 1 to 3. When the alkoxysilane has three or more amino groups, the organic chain is lengthened. As a result, not only color stability deteriorates after firing, but also it becomes difficult to synthesize and it is expensive. When n of the organic chain is 3 or more, the organic chain is lengthened and stability deteriorates. Specific examples of the alkoxysilane having an amino group used in the present invention include γ-aminopropyltrimethoxysilane, γ-aminopropyltriethoxysilane, N-β(aminoethyl)γ-aminopropylmethyldimethoxysilane, N-β(aminoethyl) γ-aminopropyltrimethoxysilane and N-β(aminoethyl)γ-aminopropyltriethoxysilane. A molar ratio of amount of these protective agents (amino group-containing alkoxysilane) to the amount of metal may be from 2 to 40.

Examples of the metal of metal particles include one, or two or more kinds selected from the group consisting of Au as a main component, and Ag, Pt, Cu, Pd, Ni, Zn, Ru, Rh and Ir as an accessory component. As the metal compound used to produce these metal particles, for example, there can be used metal salts such as chlorauric acid, gold potassium cyanide, silver chloride, silver nitride, silver sulfide, silver cyanide, chloroplatinic acid, tetrachlorohexaamine platinum, palladium nitrate, palladium chloride, chloroiridic acid, iridium chloride, ruthenium chloride, ruthenium nitrate, rhodium chloride, rhodium nitrate, nickel sulfate, nickel chloride, copper acetate and zinc chloride. As the reducing agent, for example, there can be used sodium borohydride, trimethylamineborane, dimethylamineborane, tertiary butylamineborane, secondary amine, 2-methylaminoethanol, diethamolamine, tertiary amine, diethylmethylamine, 2-dimethylaminoethanol, methyldiethanolamine, tertiary aminehypophosphite, glycerin, alcohol, hydrogen peroxide, hydrazine, hydrazine sulfate, aqueous formaldehyde solution, tartrate, glucose, sodium N—N-diethylglycine, sodium sulfite, sulfurous acid gas and ferrous sulfate.

The average particle size of metal particles is within a range from 1 to 100 nm, and preferably from 1 to 80 nm.

The average particle size of metal particles is particularly preferably within a range from 1 to 60 nm. The metal colloidal particles of the present invention are granular particles having a spherical, multiangular or ameboid shape. The metal particles having an average particle size of 0.1 to 60 nm are excellent in stability. When the particle size is more than 60 nm, there arises a phenomenon wherein sedimentation naturally occurs due to dead weight. When the particle size is less than 0.1 nm, the color developing effect is lowered.

The metal colloid of the present invention is characterized in that the above metal colloidal particles of the present invention are dispersed in either or both of an aqueous dispersion medium and a nonaqueous dispersion medium in a predetermined proportion while mixing. The solvent may be aqueous or nonaqueous and the mixing proportion can also be optionally adjusted. In the metal colloid of the present invention, since the protective agent constituting metal colloidal particles is firmly bonded to the surface of metal particles using a nitrogen atom or an atomic group as an anchor, a colloidal solution is extremely stable and a high concentration metal colloid can be obtained. The concentration of the metal colloid obtained by a conventional method is approximately 1% by weight or less. In the present invention, a metal colloid having a concentration of 10% by weight or more can be obtained. Moreover, in such a high concentration metal colloid, the colloidal solution is stable and less viscosity occurs, as described above. Furthermore, a thin film having larger film strength can be formed.

The metal colloid thin film of the present invention can be formed by using the above metal colloid, but the film forming method is not specifically limited. For example, a thin film may be formed by coating a metal colloidal solution prepared by dispersing the metal colloidal particles in an organic solvent on the surface of a base material, followed by drying, or coating the solution, followed by drying and further firing. A metal colloid-containing coat showing various gold-based color tones can be obtained by coating the metal colloid of the present invention on the surface of the base material.

It is preferred that the metal colloid-containing coat formed article formed by coating the metal colloid of the present invention on the surface of the base material and removing the dispersion medium from the metal colloid further contains one, or two or more kinds selected from the group consisting of metal powder, metal foil, fine metal particles, brightener, lame agent, cut pieces of colored paper, natural gems and artificial gems. Decorativeness is enhanced by containing the metal powder in or the surface of the coat. When Au is used as metal used in the metal powder, metal foil or fine metal particles, high sensuousness is obtained. Examples of the method of coating the metal colloid on the surface of the base material include, but are not limited to, lithographic printing, gravure printing, offset printing, carton printing, metal printing, form printing, duplex printing, over printing, ink jet printing, screen printing, slit coating method, dispenser method, spin coating method, spraying method, dipping method and airbrushing method, and all conventionally known methods can be used.

Examples of the base material used in the metal colloid-containing coat formed article of the present invention include materials such as glass, plastic, metal, lumber, ceramic including tile, cement, concrete, stone, fiber, paper and leather. Specific examples of the base material include materials such as artificial nail, natural hair, artificial hair, jewelries, plastic model, small bag for amulet case and skippet, card for business car, memorial card, invitation card and greeting card, colored paper, doll, deity and Buddhist image, mortuary tablet, clothes, woven fabric and picture frame. Deity and Buddhist image as used herein refers to an image relating to any religion existing in the world and is not limited to denomination of the religion. When the base material is jewelry, this jewelry may be made of a noble metal clay.

The transfer sheet of the present invention will now be described.

The transfer sheet of the present invention is characterized by comprising a metal colloid-containing coat formed by coating, spraying, printing, ejecting or transferring the metal colloid of the present invention on a transfer substrate wherein either of both of the surface and the back surface are subjected to a release treatment, and removing the dispersion medium from the metal colloid. Examples of the method of coating the metal colloid on the surface of the transfer substrate include, but are not limited to, lithographic printing, gravure printing, offset printing, carton printing, metal printing, form printing, duplex printing, over printing, ink jet printing, screen printing, slit coating method, dispenser method, spin coating method, spraying method, dipping method and airbrushing method, and all conventionally known methods can be used. By further comprising a surface protective layer made of an acrylic resin between the transfer substrate and the metal colloid-containing coat, the surface protective layer is formed on the surface of the transfer film in case of transferring. By further comprising an adhesive layer made of a hot melt type resin on the surface of the metal colloid-containing coat, adhesion between the transfer film and the surface of the base material is improved in case of transferring. In the transfer sheet of the present invention, one, or two or more kinds selected from the group consisting of metal powder, metal foil, fine metal particles, brightener, lame agent, cut pieces of colored paper, natural gems and artificial gems used in the metal colloid-containing coat formed article of the present invention are preferably contained in the metal colloid-containing coat. Decorativeness is enhanced by containing the metal powder in the coat. High sensuousness is obtained by using Au as metal used in the metal powder, metal foil or fine metal particles A metal colloid-containing coat formed article with a transfer film formed on the surface can be obtained by transferring the metal colloid-containing coat of the transfer sheet of the present invention on the surface of the base material. Examples of the base material on which the coated is transferred include materials selected from the group of materials consisting of glass, plastic, metal, lumber, ceramic including tile, cement, concrete, stone, fiber, paper and leather. Specific examples of the base material include materials selected from the group consisting of artificial nail, natural hair, artificial hair, jewelries, plastic model, small bag for amulet case and skippet, card for business card and memorial card, colored paper, doll, deity and Buddhist image, mortuary tablet, clothes, woven fabric and picture frame. Deity and Buddhist image as used herein refers to an image relating to any religion existing in the world and is not limited to denomination of the religion. When the base material is jewelry, this jewelry may be made of a noble metal clay. It is preferred that the base material on which the coat is transferred further contains one, or two or more kinds selected from the group consisting of metal powder, metal foil, fine metal particles, brightener, lame agent, cut pieces of colored paper, natural gems and artificial gems. Decorativeness is enhanced by containing the above metal powder in the base material. High sensuousness is obtained by using Au as metal used in the metal powder, metal foil or fine metal particles.

The pen, the brush-pencil, the cartridge for pen and the disposable ampul of the present invention will now be described.

The pen, the brush-pencil, the cartridge for pen and the disposable ampul of the present invention is a pen, a brush-pencil, a cartridge for pen and a disposable ampul, which are characterized by being filled with the above metal colloid of the present invention. In the metal colloidal particles in the metal colloid used in the present invention, since the protective agent is bonded to the surface of metal particles using nitrogen or an atomic group including nitrogen as an anchor, the metal colloidal solution is stable and viscosity change to the initial viscosity is low, a pen, a brush-pencil, a cartridge for pen and a disposable ampul, which are excellent in quality-retaining property can be obtained. With the constitution of the metal particles constituting the metal colloid filled in the pen, characters and patterns showing various gold-based color tones can be drawn. The pen filled with the metal colloid as an ink is very advantageous to easily draw characters and patterns made of the metal colloid because the ink is easily transferred to a container. It is possible to use as a water based ball-point pen, an oil based ball-point pen and a brush-pencil. The type and form of the pen are not limited.

An example of a cartridge for pen filled with the metal colloid of the present invention as an ink, and a pen connected with the cartridge for pen will now be described.

Figures 19, 20A:
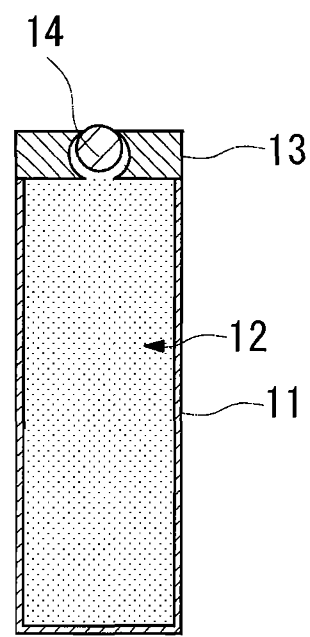
FIG. 19 is a sectional view showing a transfer sheet Example of 24.
Figure 20B:
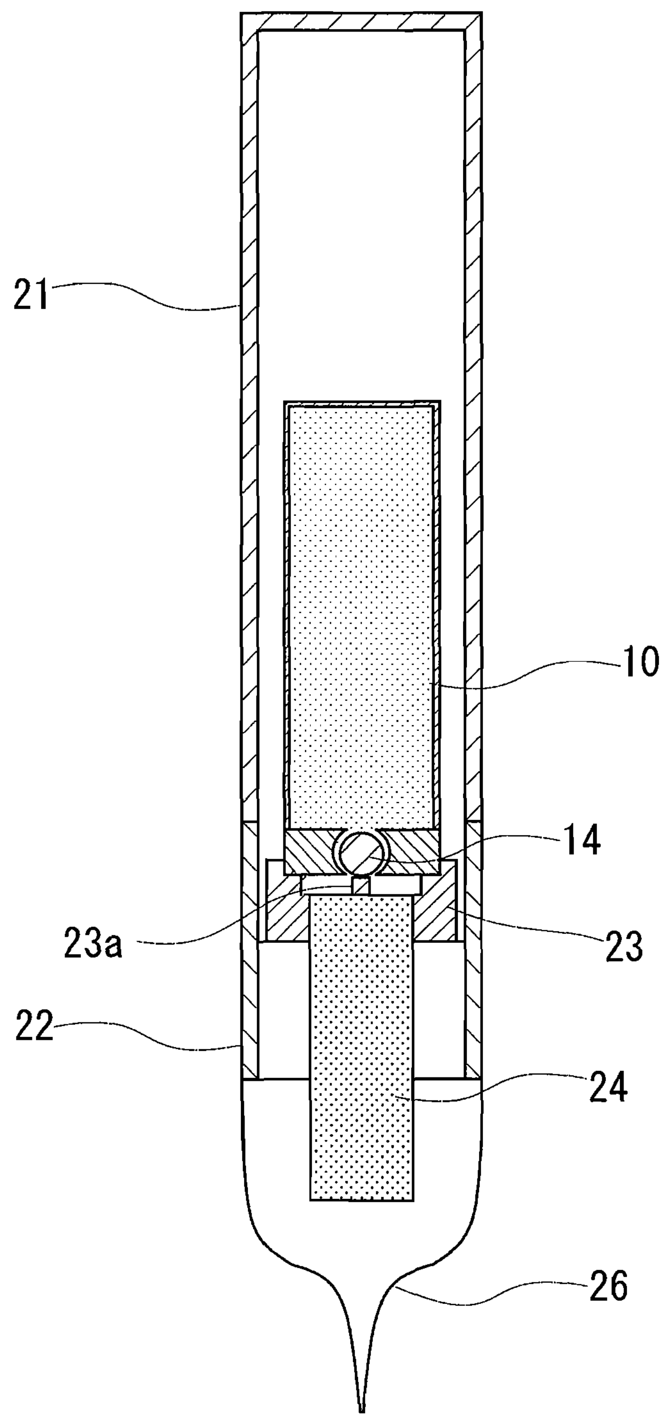
FIG. 20 A is a sectional view showing a cartridge for pen which is filled with a metal colloid of Example 38 as an ink.

As shown in FIG. 20 A, there was prepared a cartridge 10 for pen which is composed of a tubular body 11 having a closed lower portion, a lid portion 13 which is joined with the upper portion of the tubular body 11 and is provided with a spherical continuous hole at center, and a spherical plug 14 having a diameter, which is smaller than the shape of the continuous hole and is enough to prevent from falling off from the continuous hole, inserted into the continuous hole of the lid portion 13, the tubular body 11 being filled with the metal colloidal 12 of the present invention. The tubular body 11 and the lid portion 13 are preferably made of a synthetic resin, and the spherical plug 14 is preferably made of metal. In the cartridge 10 for pen, when the spherical plug 14 inserted loosely is pushed up into the cartridge in the state where the lid portion 13 faces downward or obliquely downward, a gap is formed between the lid portion 13 and the spherical plug 14 and the metal colloid is discharged from the gap due to gravity.

As shown in FIG. 20 B, a pen 20 comprising the cartridge 10 for pen incorporated thereinto is composed of a cylindrical upper shaft barrel 21, a cylindrical lower shaft barrel 22, the upper end of which can be connected to the lower end of the upper shaft barrel 21, and a tip 26 which is connected to the other end of the lower shaft barrel 22. The inner wall of the lower shaft barrel 22 is provided with a convex portion 23*a* which inserts the cartridge 10 for pen and contacts with the lid portion 13, thereby to push up the spherical plug 14 into the cartridge 10 for pen. In the connection portion 23, there is provided a core portion 24 capable of being impregnated with the dilute metal colloidal solution discharging from the cartridge 10 due to gravity while protruding the other end of the lower shaft barrel 22 when the cartridge 10 for pen is connected to the connection portion 23 and the spherical plug 14 is pushed up by the connection portion 23. The tip 26 connected to the other end of the lower shaft barrel 22 serves to eject the metal colloid, with which the core portion 24 is impregnated, from the tip. The upper shaft barrel 21, the cylindrical lower shaft barrel 22 and the connection portion 23 are preferably made of a synthetic resin. The core portion 24 is preferably made of a synthetic resin having a structure wherein pores capable of being impregnated with the metal colloid are formed.

The cartridge 10 for pen was connected to the pen 20 by contacting the lid portion 13 of the cartridge with the connection portion 23 and pushing the connection portion 23 and the plug 14 into the cartridge 10 for pen. In that case, the metal colloidal 12 filled into the cartridge 10 is discharged from the gap between the lid portion 13 and the spherical plug 14 and thus the core portion 24 is impregnated with the dilute metal colloidal solution, which is supplied to the tip 26 through the core portion 24. The pen comprising the cartridge 10 for pen connected thereto is easy to draw and was capable of drawing smoothly. This pen is very advantageous to write desired characters and to draw predetermined patterns on the desired base material, and the characters and patterns drawn by the pen showed metal color with various gold-based color tones and metal gloss and were excellent in brightness. The type and form of the cartridge for pen are not limited.

The disposable ampul refers to a disposal container made of a synthetic resin wherein a metal colloid is sealed by filling a metal colloid and thermally bond-contacting the upper of the container, sealing of the metal colloid can be easily broken by rotating the lid portion in the lateral direction and can be used as an ink comprising the metal colloid after transferring to any container. When a small amount of the metal colloid is stored using the disposable ampul, since sealing of a required amount of the metal colloid may be broken in case of using, expensive metal colloid hardly deteriorates.

An example of the disposable ampul will now be described.

Figure 21:
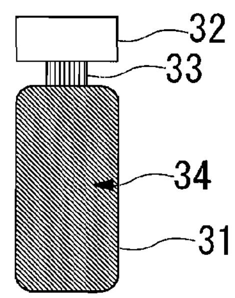
FIG. 21 is a sectional view showing a disposable ampul of Example 39.

As shown in FIG. 21, a disposable ampul 30 is composed of a tubular body 31 having a closed lower portion, a cut portion 33 joined with the upper portion of the tubular body 31, and a lid portion 32. The cut portion 33 is provided with a smaller width than that of the tubular body 31 and the lid portion 32 so that it can be cut by a hand operation. The tubular body 31, the lid portion 32 and the cut portion 33 are preferably made of a synthetic resin. The disposable ampul 30 has a structure that a metal colloid 34 is sealed by thermal contact bonding of the cut portion 33 and the lid portion 32 after filling the tubular body 31 with a metal colloid 34.

In the disposable ampul 30 thus obtained, the lid portion 32 can be easily cut from the cut portion 33 through the lever rule by laterally rotating the lid portion 32 and the cut surface is communicated with the inside of the tubular body 31. The metal colloid filled in the tubular body 31 can be used after taking out from the communicated portion. The type and form of the disposable ampul are not limited.

The stamp pad and the seal impression pad of the present invention will now be described.

The stamp pad and the seal impression pad of the present invention are a stamp pad and a seal impression pad, impregnated with the metal colloid of the present invention as an ink. It is possible to use as the stamp pad and the seal impression pad by sufficiently impregnating with the metal colloid adjusted to a predetermined concentration. The patterns made of the metal colloid formed by using the stamp pad and the seal impression pad of the present invention show gold-based color tone and metal gloss by the constitution of the metal particles constituting the metal colloid. Furthermore, it can also be used as a drawn material wherein optional patterns are drawn by using an ink with which the stamp pad or seal impression pad are impregnated.

Furthermore, the metal colloid-containing coat formed article using the ink jet printer of the present invention will be described.

The metal colloid-containing coat formed article using the ink jet printer of the present invention is a metal colloid-containing coat formed article which is characterized by drawing through an ink jet printer using the metal colloid of the present invention as an ink. The metal colloid-containing coat formed article drawn by an ink jet printer using the metal colloid of the present invention as an ink show gold-based color tone and metal gloss by the constitution of the metal particles constituting the metal colloid. Specifically, first, a paper wherein patterns are written on the surface by a commercially available black ink using a seal impression and a stamp, a colored paper wherein characters and patterns are drawn on the surface using a black pen, and a colored paper wherein a hand print and a foot print are formed using a black ink are prepared. Using an image scanner, the surface of the paper and that of the colored paper are scanned and the resulting image data are inputted into a computer. By an ink jet printer using the metal colloid of the present invention as an ink, image data are printed on the paper and the colored paper based on the inputted image data. Characters and patterns printed on the paper and the colored paper using the metal colloid of the present invention show the same shape as that of black colored characters and patterns drawn and also show metal gloss and color tone peculiar to metal and are excellent in brightness.

In this embodiment, using the image scanner, the surface of the paper and that of the colored paper were scanned and the resulting image data were inputted into a computer and then printed using the ink jet printer. Using the image scanner, not only base papers such as paper and colored paper, but also a photograph of these base papers, and a print and a publication in which these patterns and characters are described may be scanned and the resulting image data may be inputted into a computer and directly printed using an ink jet printer to obtain a metal colloid-containing coat formed article.

The third best mode for carrying out the present invention will now be described.

The metal colloid-containing coat formed article of the present invention is characterized in that it is formed by coating, spraying, printing, ejecting or transferring a metal colloid on the surface of a base material and removing the dispersion medium from the metal colloid. The metal colloid used in the present invention is formed by dispersing metal colloidal particles in either or both of an aqueous dispersion medium or a nonaqueous dispersion medium in a predetermined proportion. The metal colloidal particles of the present invention comprise metal particles and a protective agent coordination-modified on the surface of the particles. The protective agent has a carbon skeleton containing nitrogen in the molecule, and has a structure of being coordination-modified on the surface of metal particles using nitrogen or an atomic group including nitrogen as an anchor. Furthermore, the protective agent contains one, or two or more functional groups selected from the group consisting of alkoxysilyl group, silanol group and hydroxyalkyl group in a molecular structure.

Since the protective agent constituting metal colloidal particles in the metal colloid, which constitutes the coat, has a carbon skeleton containing nitrogen in the molecule, and having a structure of being firmly coordination-modified on the surface of metal particles using nitrogen or an atomic group including nitrogen as an anchor, the metal colloid obtained by the metal colloidal particles in a dispersion medium shows extremely high stability. As a result, a high concentration metal colloid can be obtained and also less viscosity change and color tone change occur. The alkoxysilyl group, the silanol group and the hydroxyalkyl group contained in the molecular structure of the protective agent have high reactivity and chemically bonded to all base materials. Metal particles are spontaneously self-organized and cause closest packing, and are condensed with a reactive functional group. Therefore, it is considered that a metal colloid-containing coat made of the metal colloid having these characteristics of the present invention is converted into an organic-inorganic hybrid bulk between particles, and therefore has comparatively high film strength as compared with a metal colloid-containing coat formed by using a metal colloid comprising a nonreactive protective agent or a metal colloid comprising a protective agent having low reactivity.

Since the protective agent is firmly bonded to the surface of metal particles by bonding one end of the protective agent is bonded to the surface of metal particles using a protective agent coordination-modified site as an anchor, metal colloid having good stability is obtained. Since the protective agent end site located at the other end of the protective agent constitutes the outermost surface of the colloid and this protective agent end site is provided with one, or two or more functional groups with high reactivity selected from the group consisting of alkoxysilyl group, silanol group and hydroxyalkyl group, adhesion with the base material is excellent. The fact that the protective agent is bonded to the surface of metal particles using the protective agent coordination-modified site can be confirmed by analytical means, for example, NMR, GPC, TG-DTA, FT-IR, XPS, TOF-SIMS, SAXS, visible ultraviolet spectroscopy, SERS or XAFS. Using the above analytical means, it is possible to confirm by what element or atomic group the protective agent is anchored.

Examples of base material used in the metal colloid-containing coat formed article of the present invention include metarials such as glass, plastic, metal, lumber, ceramic including tile, cement, concrete, stone, fiber, paper and leather. Specific examples of the base material include artificial nail, natural hair, artificial hair, jewelries, plastic model, small bag such as amulet case and skippet, card such as business card, memorial card, invitation card and greeting card, colored paper, doll, deity and Buddhist image, mortuary tablet, clothes, woven fabric and picture frame. Deity and Buddhist image as used herein refers to an image relating to any religion existing in the world and is not limited to denomination of the religion. When the base material is jewelry, this jewelry may be made of a noble metal clay.

It is preferred that the metal colloid-containing coat formed article of the present invention further contains one, or two or more kinds selected from the group consisting of metal powder, metal foil, fine metal particles, brightener, lame agent, cut pieces of colored paper, natural gems and artificial gems. Decorativeness is enhanced by containing the metal powder in or on the surface of the coat. High sensuousness is obtained by using Au as metal used in the metal powder, metal foil or fine metal particles. Examples of the method of coating the metal colloid on the surface of the base material include, but are not limited to, lithographic printing, gravure printing, carton printing, metal printing, form printing, duplex printing, over printing, ink jet printing, screen printing, slit coating method, dispenser method, spin coating method, spraying method, dipping method and airbrushing method, and all conventionally known methods can be used.

The atomic group including nitrogen in the protective agent constituting the metal colloidal particles of the present invention includes at least one selected from the group consisting of amino group, amide atomic group and imide atomic group. The method of producing metal colloidal particles of the present invention is not limited. The method may be a method by which the above bonded structure to metal colloidal particles is obtained. An example of a specific method is as follows. In a nonaqueous system, an alkoxysilane having an amino group is mixed with a metal compound and the metal compound is reduced in the presence of a reducing agent to obtain metal colloidal particles wherein the protective agent comprising the alkoxysilane is bonded to the surface of metal particles using a nitrogen atomic group of the alkoxysilane as an anchor. The nonaqueous system means that metal reduction of the metal compound is conducted in an organic solution of an amino group-containing alkoxysilane or an alcohol without conducting metal reduction in an aqueous solution of the metal compound. In the method of bonding the amino group-containing alkoxysilane after producing metal colloidal particles by the reductive reaction in the aqueous solution like a conventional method, since the alkoxysilane is exposed in water, the substitution reaction may not proceed by the influence of the hydrolysis. If the substitution reaction proceeds, stability is impaired by the following hydrolysis and thus it is difficult to obtain metal colloidal particles of the present invention.

Metal colloidal particles wherein an alkoxysilyl group is chelete-coordinated by using a chelating agent such as β diketon have the effect of delaying the hydrolysis reaction and stability is enhanced furthermore. The alkoxysilane preferably has one or two amino groups and also has an organic chain ($-CH_2-$) n wherein n is 1 to 3. When the alkoxysilane has three or more amino groups, the organic chain is lengthened. As a result, not only color stability deteriorates after firing, but also it becomes difficult to synthesize and it is expensive. When n of the organic chain is 3 or more, the organic chain is lengthened and stability deteriorates. Specific examples of the alkoxysilane having an amino group used in the present invention include γ-aminopropyltrimethoxysilane, γ-aminopropyltriethoxysilane, N-β(aminoethyl)γ-aminopropylmethyldimethoxysilane, N-β(aminoethyl) γ-aminopropyltrimethoxysilane and N-β(aminoethyl)γ-aminopropyltriethoxysilane. A molar ratio of amount of these protective agents (amino group-containing alkoxysilane) to the amount of metal may be from 2 to 40.

Examples of the metal of metal particles constituting metal colloidal particles include one, or two or more kinds selected from the group consisting of Au, Ag, Pt, Cu, Pd, Ni, Zn, Ru, Rh and Ir. As the metal compound used to produce these metal particles, there can be used metal salts such as chlorauric acid, gold potassium dicyanide, silver chloride, silver nitride, silver sulfide, silver cyanide, chloroplatinic acid, tetrachlorohexaamine platinum, palladium nitrate, palladium chloride, chloroiridic acid, iridium chloride, ruthenium chloride, ruthenium nitrate, rhodium chloride, rhodium nitrate, nickel sulfate, nickel chloride, copper acetate and zinc chloride. As the reducing agent, for example, there can be used sodium borohydride, trimethylamineborane, dimethylamineborane, tertiary butylamineborane, secondary amine, tertiary aminehypophosphite, glycerin, alcohol, hydrogen peroxide, hydrazine, hydrazine sulfate, aqueous formaldehyde solution, tartrate, glucose, sodium N—N-diethylglycine, sodium sulfite, sulfurous acid gas and ferrous sulfate.

The average particle size of the metal particles constituting metal colloidal particles is within a range from 1 to 100 nm, and preferably from 1 to 80 nm. When the metal particles constituting metal colloidal particles contain Au as a main component, the average particle size of Au particles is preferably within a range from 1 to 60 nm. The metal colloidal particles are granular particles having a spherical, multiangular or ameboid shape. The metal colloidal particles having an average particle size of 0.1 to 60 nm are excellent in stability. When the particle size is more than 60 nm, there arises a phenomenon wherein sedimentation naturally occurs due to dead weight. When the particle size is less than 0.1 nm, the color developing effect is lowered.

According to the present invention, a high concentration metal colloid can be obtained. The concentration of the metal colloid obtained by a conventional method is approximately 1% by weight or less. In the present invention, a metal colloid having a concentration of 10% by weight or more can be obtained. Moreover, in such a high concentration metal colloid, the colloidal solution is stable and, as described above, viscosity change is small. For example, in case of a metal colloid of gold wherein the metal colloidal particles contain Au, the Au concentration is stable within a range from 0.1 to 95% by weight and an organic solvent or water can be used as a dispersion medium. The concentration of Au in the metal colloid is more preferably within a range from 10 to 60% by weight. The metal colloid of the present invention and the thin film obtained from the metal colloid have excellent heat resistance. Specifically, change of color tone is 2% or less even when maintained at a heating base temperature, for example, from about 300 to 400° C. for 400 hours, and color tone scarcely changes.

When the metal particles as a component of the metal colloid constituting a film contain Au particles as a main component, the metal colloidal particles of the present invention show glossy color tone peculiar to Au particles. A coat formed by formed by coating, spraying, printing, ejecting or transferring a metal colloid, which is obtained by dispersing metal colloidal particles containing Au colloidal particles as a main component and also containing 0.1 to 10% metal particles having an average particle size of 1 to 10 nm, in addition to the Au colloidal particles, in a dispersion medium, and removing the dispersion medium from the metal colloid, shows a pink gold color tone.

The above color tone can be identified by CIE 1976 L*a*b* color space (light source for measurement C: color temperature: 6774K). In case of the pink gold color tone of the present invention, psychometric lightness value L* in CIE 1976 L*a*b* color space is from 25 to 99, chromaticness indices value a* and value b* are from +10 to +25 and from +0.1 to +60, respectively.

The transfer sheet of the present invention will now be described.

The transfer sheet of the present invention is characterized by having a metal colloid-containing coat formed by coating, spraying, printing, ejecting or transferring a metal colloid used in the above metal colloid-containing coat formed article on a transfer substrate wherein either of both of the surface and the back surface are subjected to a release treatment, and removing the dispersion medium from the metal colloid. Examples of the method of coating the metal colloid on the surface of the transfer substrate include, but are not limited to, lithographic printing, gravure printing, offset printing, carton printing, metal printing, form printing, duplex printing, over printing, ink jet printing, screen printing, slit coating method, dispenser method, spin coating method, spraying method, dipping method and airbrushing method, and all conventionally known methods can be used. By further comprising a surface protective layer made of an acrylic resin between the transfer substrate and the metal colloid-containing coat, the surface protective layer is formed on the surface of the transfer film in case of transferring. By further comprising an adhesive layer made of a hot melt type resin on the surface of the metal colloid-containing coat, adhesion between the transfer film and the surface of the base material is improved in case of transferring. In the transfer sheet of the present invention, one, or two or more kinds selected from the group consisting of metal powder, metal foil, fine metal particles, brightener, lame agent, cut pieces of colored paper, natural gems and artificial gems used in the metal colloid-containing coat formed article of the present invention are preferably contained in the metal colloid-containing coat. Decorativeness is enhanced by containing the metal powder in the coat. High sensuousness is obtained by using Au as metal used in the metal powder, metal foil or fine metal particles A metal colloid-containing coat formed article with a transfer film formed on the surface can be obtained by transferring the metal colloid-containing coat of the transfer sheet of the present invention on the surface of the base material. Examples of the base material on which the coated is transferred include materials selected from the group of materials consisting of glass, plastic, metal, lumber, ceramic including tile, cement, concrete, stone, fiber, paper and leather. Specific examples of the base material include materials selected from the group consisting of artificial nail, natural hair, artificial hair, jewelries, plastic model, small bag for amulet case and skippet, card for business card and memorial card, colored paper, doll, deity and Buddhist image, mortuary tablet, clothes, woven fabric and picture frame. Deity and Buddhist image as used herein refers to an image relating to any religion existing in the world and is not limited to denomination of the religion. When the base material is jewelry, this jewelry may be made of a noble metal clay. It is preferred that the base material on which the coat is transferred further contains one, or two or more kinds selected from the group consisting of metal powder, metal foil, fine metal particles, brightener, lame agent, cut pieces of colored paper, natural gems and artificial gems. Decorativeness is enhanced by containing the above metal powder in the base material. High sensuousness is obtained by using Au as metal used in the metal powder, metal foil or fine metal particles The base material with a conductive film of the present invention will now be described.

The base material with a conductive film of the present invention is obtained by coating, spraying, printing, ejecting or transferring a metal colloid used in the metal colloid-containing coat formed article of the present invention on a base material and maintaining the base material with the metal colloid in a predetermined atmosphere at a temperature of 15 to 450° C. for 1 to 60 minutes. The resulting conductive film is a low-resistance conductive film having resistivity of $1\times10^{-3}$ Ω·cm or less. The material of the base material used in the base material with a conductive film of the present invention is not specifically limited. According to the method of forming the base material with a conductive film, first, the metal colloid is coated on the base material by coating, spraying, printing, ejecting or transferring using a method such as lithographic printing, gravure printing, offset printing, carton printing, metal printing, form printing, duplex printing, over printing, ink jet printing, screen printing, slit coating method, dispenser method, spin coating method, spraying method, dipping method or airbrushing method. Then, the base material with the metal colloid is maintained in a predetermined atmosphere at a temperature within a range from 15 to 450° C. for 1 to 60 minutes. The solvent contained in the metal colloid is removed by subjecting to the heat treatment to obtain a conductive film having low resistance. The base material with a conductive film of the present invention can be used as a wiring material. Regarding the conditions for forming a conductive film, it is preferred to maintain at a temperature within a range from 15 to 350° C. for 30 to 60 minutes. When the retention time is less than 30 minutes at the temperature within the above range, desired conductivity may not be exhibited because of insufficient decomposition or elimination of the solvent or the protective agent. Even when the retention time exceeds 60 minutes, resistivity of the resulting conductive film does not change remarkably, excess retention time is not preferred in view of productivity and cost. When the temperature is within a range from 350 to 450° C., it is preferable to maintain for 1 to 60 minutes. When the retention time is less than one minute at the temperature within the above range, desired conductivity may not be exhibited because of insufficient decomposition or elimination of the solvent or the protective agent, or insufficient sintering. Even when the retention time exceeds 60 minutes, resistivity of the resulting conductive film does not change remarkably, excess retention time is not preferred in view of productivity and cost.

The pen, the brush-pencil, the cartridge for pen and the disposable ampul of the present invention will now be described.

The pen, the brush-pencil, the cartridge for pen and the disposable ampul of the present invention is a pen, a brush-pencil, a cartridge for pen and a disposable ampul, which are characterized by being filled with the above metal colloid of the present invention. In the metal colloidal particles in the metal colloid used in the present invention, since the protective agent is bonded to the surface of metal particles using nitrogen or an atomic group including nitrogen as an anchor, the metal colloidal solution is stable and viscosity change to the initial viscosity is low, a pen, a brush-pencil, a cartridge for pen and a disposable ampul, which are excellent in quality-retaining property can be obtained. The pen filled with the metal colloid as an ink is very advantageous to easily draw characters and patterns made of the metal colloid because the ink is easily transferred to a container. It is possible to use as a water based ball-point pen, an oil based ball-point pen and a brush-pencil. The type and form of the pen are not limited.

An example of a cartridge for pen filled with the metal colloid of the present invention as an ink, and a pen connected with the cartridge for pen will now be described.

As shown in FIG. 20 A, a cartridge 10 for pen is composed of a tubular body 11 having a closed lower portion, a lid portion 13 which is joined with the upper portion of the tubular body 11 and is provided with a spherical continuous hole at center, and a spherical plug 14 inserted loosely into the continuous hole of the lid portion 13, the tubular body 11 being filled with the metal colloidal 12 of the present invention. The tubular body 11 and the lid portion 13 are preferably made of a synthetic resin, and the spherical plug 14 is preferably made of metal. In the cartridge 10 for pen, when the spherical plug 14 inserted loosely is pushed up into the cartridge in the state where the lid portion 13 faces downward or obliquely downward, a gap is formed between the lid portion 13 and the spherical plug 14 and the metal colloid is discharged from the gap due to gravity.

As shown in FIG. 20 B, a pen 20 comprising the cartridge 10 for pen incorporated thereinto is composed of a cylindrical upper shaft barrel 21, a cylindrical lower shaft barrel 22, the upper end of which can be connected to the lower end of the upper shaft barrel 21, and a tip 26 which is connected to the other end of the lower shaft barrel 22. The inner wall of the lower shaft barrel 22 is provided with a connecting portion 23 which inserts the cartridge 10 for pen and contacts with the lid portion 13, thereby to push up the spherical plug 14 into the cartridge 10 for pen. In the connection portion 23, there is provided a core portion 24 capable of being impregnated with the dilute metal colloidal solution discharging from the cartridge 10 due to gravity while protruding the other end of the lower shaft barrel 22 when the cartridge 10 for pen is connected to the connection portion 23 and the spherical plug 14 is pushed up by the connection portion 23. The tip 26 connected to the other end of the lower shaft barrel 22 serves to eject the metal colloid, with which the core portion 24 is impregnated, from the tip. The upper shaft barrel 21, the cylindrical lower shaft barrel 22 and the connection portion 23 are preferably made of a synthetic resin. The core portion 24 is preferably made of a synthetic resin having a structure wherein pores capable of being impregnated with the metal colloid are formed.

The cartridge 10 for pen was connected to the pen 20 by contacting the lid portion 13 of the cartridge with the connection portion 23 and pushing the connection portion 23 and the plug 14 into the cartridge 10 for pen. In that case, the metal colloidal 12 filled into the cartridge 10 is discharged from the gap between the lid portion 13 and the spherical plug 14 and thus the core portion 24 is impregnated with the dilute metal colloidal solution, which is supplied to the tip 26 through the core portion 24. The pen comprising the cartridge 10 for pen connected thereto is easy to draw and was capable of drawing smoothly. This pen thus obtained is very advantageous to write desired characters and to draw predetermined patterns on the desired base material, and the characters and patterns drawn by the pen showed metal color with various gold-based color tones and metal gloss and were excellent in brightness. The type and form of the cartridge for pen are not limited.

The disposable ampul refers to a disposal container made of a synthetic resin wherein a metal colloid is sealed by filling a metal colloid and thermally bond-contacting the upper of the container, sealing of the metal colloid can be easily broken by rotating the lid portion in the lateral direction and can be used as an ink comprising the metal colloid after transferring to any container. When a small amount of the metal colloid is stored using the disposable ampul, since sealing of a required amount of the metal colloid may be broken in case of using, expensive metal colloid hardly deteriorates.

An example of the disposable ampul will now be described.

As shown in FIG. 21, a disposable ampul 30 is composed of a tubular body 31 having a closed lower portion, a cut portion 33 joined with the upper portion of the tubular body 31, and a lid portion 32. The cut portion 33 is provided with a smaller width than that of the tubular body 31 and the lid portion 32 so that it can be cut by a hand operation. The tubular body 31, the lid portion 32 and the cut portion 33 are preferably made of a synthetic resin. The disposable ampul 30 has a structure that a metal colloid 34 is sealed by thermal contact bonding of the cut portion 33 and the lid portion 32 after filling the tubular body 31 with a metal colloid 34.

In the disposable ampul 30 thus obtained, the lid portion 32 can be easily cut from the cut portion 33 through the lever rule by laterally rotating the lid portion 32 and the cut surface is communicated with the inside of the tubular body 31. The metal colloid filled in the tubular body 31 can be used after taking out from the communicated portion. The type and form of the disposable ampul are not limited.

The stamp pad and the seal impression pad of the present invention will now be described.

The stamp pad and the seal impression pad of the present invention are a stamp pad and a seal impression pad, impregnated with the metal colloid of the present invention as an ink. It is possible to use as the stamp pad and the seal impression pad by sufficiently impregnating with the metal colloid adjusted to a predetermined concentration. The patterns made of the metal colloid formed by using the stamp pad and the seal impression pad of the present invention show color tone and metal gloss peculiar to metal. Furthermore, it can also be used as a drawn material wherein optional patterns are drawn by using an ink with which the stamp pad or seal impression pad are impregnated.

Furthermore, the drawn material using the ink jet printer of the present invention will be described.

The drawn material using the ink jet printer of the present invention is a drawn material which is characterized by drawing through an ink jet printer using the metal colloid of the present invention as an ink. The drawn material drawn by an ink jet printer using the metal colloid of the present invention as an ink show color tone and metal gloss peculiar to gold. Specifically, first, a paper wherein patterns are written on the surface by a commercially available black ink using a seal impression and a stamp, a colored paper wherein characters and patterns are drawn on the surface using a black pen, and a colored paper wherein a hand print and a foot print are formed using a black ink are prepared. Using an image scanner, the surface of the paper and that of the colored paper are scanned and the resulting image data are inputted into a computer. By an ink jet printer using the metal colloid of the present invention as an ink, image data are printed on the paper and the colored paper based on the inputted image data. Characters and patterns printed on the paper and the colored paper using the metal colloid of the present invention show the same shape as that of black colored characters and patterns drawn and also show metal gloss and color tone peculiar to metal and are excellent in brightness.

In this embodiment, using the image scanner, the surface of the paper and that of the colored paper were scanned and the resulting image data were inputted into a computer and then printed using the ink jet printer. Using the image scanner, not only base papers such as paper and colored paper, but also a photograph of these base papers, and a print and a publication in which these patterns and characters are described may be scanned and the resulting image data may be inputted into a computer and directly printed using an ink jet printer to obtain a drawn material.

EXAMPLES

Examples and Comparative Examples of the present invention will now be described in detail.

Synthesis Example 1

Chlorauric acid was prepared as a metal salt, γ-mercaptopropyltrimethoxysilane was prepared as a protective agent precursor, and dimethylamineborane was prepared as a reducing agent, respectively. First, an appropriate amount of dimethylamineborane was added to 9.00 g of γ-mercaptopropyltrimethoxysilane. A methanol solution prepared by dissolving chlorauric acid so as to adjust the metal concentration to 4.0% by weight was gradually added to prepare a mixed solution. This mixed solution was prepared by maintaining at 60° C. while stirring the mixed solution using a magnetic stirrer, and the reductive reaction was conducted until metal colloidal particles are produced and show a red color. After the completion of the reductive reaction, the mixed solution was cooled to room temperature. After cooling, the mixed solution was desalted by an ultrafiltration method to obtain a metal colloid containing water as a dispersion medium. The concentration of this metal colloid was adjusted by adding an appropriate amount of water to obtain a metal colloid having a concentration of 50% by weight wherein metal colloidal particles are dispersed in water.

Figure 2:
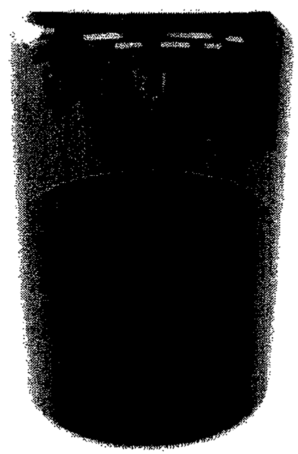
FIG. 2 is a photograph wherein metal colloidal particles of the present invention obtained in Synthesis Example 1 are placed in a storage container.
Figure 3:
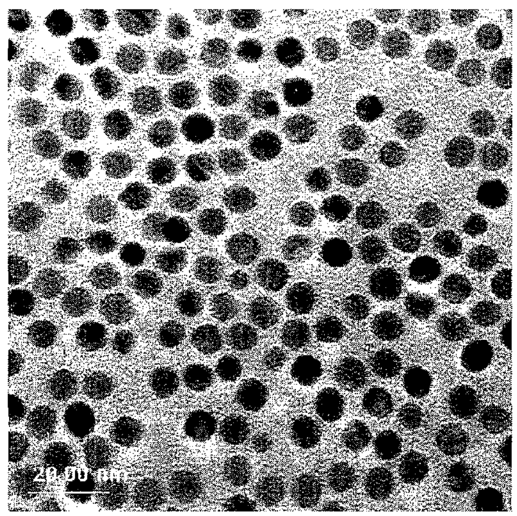
FIG. 3 is a transmission electron micrograph of metal colloidal particles of the present invention obtained in Synthesis Example 1.

A photograph wherein a metal colloid is placed in a storage container is shown in FIG. 2, and a photograph of metal colloidal particles is taken by a transmission electron microscope (TEM) and the resulting photograph is shown in FIG. 3, respectively. Protective agent molecules constituting metal colloidal particles in the resulting metal colloid were subjected to TOF-SIMS analysis. By TOF-SIMS analysis, cluster ions comprising Au and CS were predominantly detected. As is apparent from the results of TOF-SIMS analysis and NMR (C, H) analysis, the protective agent particles are coordination-modified on the surface of Au particles by sulfur.

Synthesis Example 2

Chlorauric acid was prepared as a metal salt, γ-mercaptopropyltrimethoxysilane, 2-aminoethanol and Acetylacetone were prepared as a protective agent precursor, and dimethylamineborane was prepared as a reducing agent, respectively. First, 3.00 g of γ-mercaptopropyltrimethoxysilane, 5.00 g of 2-aminoethanol and 12.00 g of acetylacetone were mixed and an appropriate amount of dimethylamineborane was added to the mixed solution. A methanol solution prepared by dissolving chlorauric acid so as to adjust the metal concentration to 4.0% by weight was gradually added to prepare a mixed solution. This mixed solution was prepared by maintaining at 60° C. while stirring the mixed solution using a magnetic stirrer, and the reductive reaction was conducted until metal colloidal particles are produced and show a red color. After the completion of the reductive reaction, the mixed solution was cooled to room temperature. After cooling, the mixed solution was desalted by an ultrafiltration method to obtain a metal colloid containing water as a dispersion medium. The concentration of this metal colloid was adjusted by adding an appropriate amount of water to obtain a metal colloid having a concentration of 50% by weight wherein metal colloidal particles are dispersed in water.

Protective agent molecules constituting metal colloidal particles in the resulting metal colloid were subjected to TOF-SIMS analysis. By TOF-SIMS analysis, cluster ions comprising Au and CS, Au and CN or Au and CO were predominantly detected. As is apparent from the results of TOF-SIMS analysis and NMR (C, H) analysis, the protective agent particles are coordination-modified on the surface of Au particles by sulfur, nitrogen and oxygen.

Synthesis Examples 3 to 27

In the same manner as in Synthesis Example 1, except that the metal salt, the protective agent precursor, the reducing agent and the dispersion medium were replaced by the compounds shown in the following Table 1 and Table 2, various metal colloids were obtained. The compounds represented by symbols (A1) to (H1) in the column of the kind of the pro tective agent precursor in Table 1 and Table 2 are shown in Table 3.

Also the protective agent molecular structure of metal colloidal particles obtained in Synthesis Examples 3 to 27 was confirmed by analyzing using NMR, TOF-SIMS, FT-IR, SAXS, visible ultraviolet spectroscopy, SERS and XAFS in combination.

TABLE 1

| Synthesis Example No. | Metal salt | Protective agent precursor Kind | Amount [g] | Reducing agent | Dispersion medium | Coordination-modifying element | Protective agent end structure |
|---|---|---|---|---|---|---|---|
| 1 | Chlorauric acid | (A1) | 9.00 | Dimethylamineborane | Methanol | Sulfur | Silanol group |
| 2 | Chlorauric acid | (A1)<br>(C1)<br>Acetylacetone | 3.00<br>5.00<br>12.00 | Dimethylamineborane | Water | Sulfur<br>Oxygen<br>Nitrogen | Hydroxyalkyl group |
| 3 | Chlorauric acid | (A1)<br>Acetylacetone | 8.00<br>12.00 | Dimethylamineborane | Water | Sulfur<br>Oxygen | Silanol group |
| 4 | Chlorauric acid | (B1)<br>(D1) | 10.00<br>8.00 | Dimethylamineborane | Ethanol | Oxygen<br>Nitrogen | Alkoxysilyl group |
| 5 | Chlorauric acid | (C1)<br>(E1) | 10.00<br>10.00 | Dimethylamineborane | Cyclohexane | Sulfur<br>Oxygen<br>Nitrogen | Hydroxyalkyl group |
| 6 | Chlorauric acid | (D1)<br>(H1)<br>Acetylacetone | 6.00<br>2.00<br>10.00 | Sodium borohydride | Cyclohexane | Oxygen<br>Nitrogen | Silanol group<br>Hydroxyalkyl group |
| 7 | Chlorauric acid | (F1)<br>Acetylacetone | 8.00<br>12.00 | Sodium borohydride | Water | Oxygen<br>Nitrogen | Silanol group |
| 8 | Chlorauric acid | (G1)<br>Acetylacetone | 8.00<br>12.00 | Dimethylamineborane | Methanol | Oxygen<br>Nitrogen | Silanol group |
| 9 | Chlorauric acid | (G1)<br>Acetylacetone | 8.00<br>12.00 | Dimethylamineborane | Water | Oxygen<br>Nitrogen | Silanol group |
| 10 | Chlorauric acid | (H1)<br>Acetylacetone | 8.00<br>12.00 | Dimethylamineborane | Water | Oxygen<br>Nitrogen | Alkoxysilyl group<br>Silanol group |
| 11 | Chlorauric acid | (H1)<br>Acetylacetone | 8.00<br>12.00 | Dimethylamineborane | Methanol | Oxygen<br>Nitrogen | Alkoxysilyl group<br>Silanol group |
| 12 | Silver nitride | (A1)<br>Acetylacetone | 8.00<br>12.00 | Sodium borohydride | Methanol | Sulfur<br>Oxygen | Silanol group |
| 13 | Silver nitride | (B1)<br>(D1) | 10.00<br>10.00 | Dimethylamineborane | Ethanol | Oxygen<br>Nitrogen | Hydroxyalkyl group |
| 14 | Silver nitride | (F1)<br>Acetylacetone | 8.00<br>12.00 | Trimethylamineborane | Water | Oxygen<br>Nitrogen | Silanol group |
| 15 | Chlorauric acid, silver nitride (weight ratio of metal = 2:1) | (G1)<br>Acetylacetone | 8.00<br>12.00 | Dimethylamineborane | Methanol | Oxygen<br>Nitrogen | Silanol group |
| 16 | Ruthenium trichloride | (D1)<br>(F1)<br>Acetylacetone | 2.00<br>6.00<br>12.00 | Sodium borohydride | Water | Oxygen<br>Nitrogen | Silanol group<br>Hydroxyalkyl group |

TABLE 2

| Synthesis Example No. | Metal salt | Protective agent precursor Kind | Amount [g] | Reducing agent | Dispersion medium | Coordination-modifying element | Protective agent end structure |
|---|---|---|---|---|---|---|---|
| 17 | Chloroplatinic acid | (G1)<br>Acetylacetone | 8.00<br>12.00 | Dimethylamineborane | Methanol | Oxygen<br>Nitrogen | Silanol group |
| 18 | Copper acetate | (H1)<br>Acetylacetone | 8.00<br>12.00 | Dimethylamineborane | Methanol | Oxygen<br>Nitrogen | Alkoxysilyl group<br>Silanol group |
| 19 | Chlorauric acid, silver nitride, copper acetate (weight ratio of metal = 6:2:1) | (G1)<br>Acetylacetone | 8.00<br>12.00 | Dimethylamineborane | Water | Oxygen<br>Nitrogen | Silanol group |
| 20 | Chlorauric acid, silver nitride, copper acetate (weight ratio of metal = 8:2:1) | (G1)<br>Acetylacetone | 8.00<br>12.00 | Dimethylamineborane | Water | Oxygen<br>Nitrogen | Silanol group |

TABLE 2-continued

| Synthesis Example No. | Metal salt | Protective agent precursor Kind | Amount [g] | Reducing agent | Dispersion medium | Coordination-modifying element | Protective agent end structure |
|---|---|---|---|---|---|---|---|
| 21 | Chlorauric acid, silver nitride, copper acetate (weight ratio of metal = 8:2:1) | (G1)<br>Acetylacetone | 8.00<br>12.00 | Dimethylamineborane | Water | Oxygen<br>Nitrogen | Silanol group |
| 22 | Chlorauric acid, silver nitride, copper acetate, palladium nitrate (weight ratio of metal = 8:1:2:1) | (G1)<br>Acetylacetone | 8.00<br>12.00 | Dimethylamineborane | Water | Oxygen<br>Nitrogen | Silanol group |
| 23 | Chlorauric acid, palladium nitrate (weight ratio of metal = 3:1) | (G1)<br>Acetylacetone | 8.00<br>12.00 | Dimethylamineborane | Water | Oxygen<br>Nitrogen | Silanol group |
| 24 | Nickel oxalate | (G1)<br>Acetylacetone | 8.00<br>12.00 | Sodium borohydride | Water, ethanol (weight ratio = 4:1) | Oxygen<br>Nitrogen | Silanol group<br>Methyldimethoxysilyl group |
| 25 | Nickel oxalate, zinc chloride (weight ratio of metal = 4:1) | (G1)<br>Acetylacetone | 8.00<br>12.00 | Sodium borohydride | Water | Oxygen<br>Nitrogen | Silanol group<br>Methyldimethoxysilyl group |
| 26 | Rhodium chloride | (B1)<br>(C1) | 10.00<br>10.00 | Dimethylamineborane | Water, N,N-dimethylformamide, ethanol (weight ratio = 3:1:1) | Oxygen<br>Nitrogen | Hydroxyalkyl group |
| 27 | Iridium chloride | (B1)<br>(C1) | 10.00<br>10.00 | Dimethylamineborane | Water, N-methyl pyrrolidinone, ethylene glycol (weight ratio = 5:1:1) | Oxygen<br>Nitrogen | Hydroxyalkyl group |

TABLE 3

| Symbol | Name |
|---|---|
| (A1) | γ-mercaptopropyltrimethoxysilane |
| (B1) | Caprylic acid |
| (C1) | 2-aminoethanol |
| (D1) | 1-amino-2-propanol |
| (E1) | Dodecylbenzenesulfonic acid |
| (F1) | N-β(aminoethyl)γ-aminopropyltrimethoxysilane |
| (G1) | N-β(aminoethyl)γ-aminopropylmethyldimethoxysilane |
| (H1) | N-β(aminoethyl)γ-aminopropyltriethoxysilane |

Example 1

A metal colloid comprising a water medium having a concentration of 50% by weight of Example 1 was produced from the metal colloid produced in Synthesis Example 1.

Comparative Example 1

First, chlorauric acid was prepared as a metal salt, γ-aminopropyltriethoxysilane was prepared as a protective agent precursor, and dimethylamineborane was prepared as a reducing agent.

A methanol solution prepared by prepared by dissolving 9.00 g of γ-aminopropyltriethoxysilane so as to adjust the gold metal concentration to 4.0% by weight was added. Subsequently, dimethylamineborane as a reducing agent was added until metal colloidal particles and show a red color. The reaction was conducted by maintaining at 60° C. while stirring the mixed solution using a magnetic stirrer. After cooling, the mixed solution was desalted by an ultrafiltration method to obtain a metal colloidal solution comprising a water medium having a concentration of 50% by weight.

Characters written on a Japanese paper using this metal colloidal solution showed color tone and metal gloss peculiar to gold, and metal was not peeled off even when the surface of characters are rubbed with a cloth.

Comparative Evaluation 1

The metal colloids obtained in Example 1 and Comparative Example 1 were divided into two samples, and then one sample was stored at 25° C. and the other sample was stored at 40° C., respectively. Then, the change of viscosity of the metal colloidal solution with time (storage days) was examined. The results are shown in FIG. 4.

Figure 4:
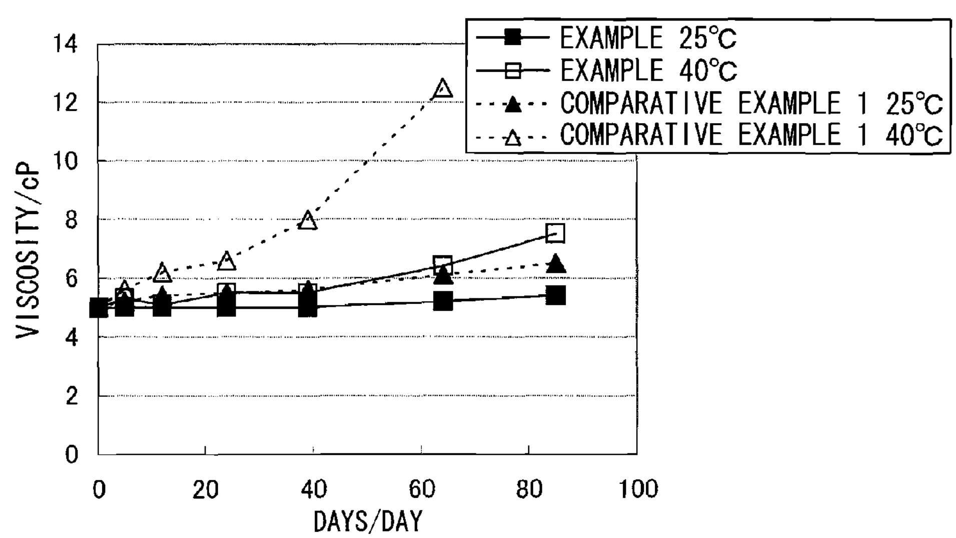
FIG. 4 is a graph showing viscosity change of metal colloids of Example 1 and Comparative Example 1 in Comparative Evaluation 1.

As is apparent from the results shown in FIG. 4, the initial viscosity of the metal colloid of Comparative Example 1 was 5 cP when stored at 25° C., and the viscosity was 6 to 6.5 cP after storing for 60 days and thus the viscosity changed by about 60%. When stored at 40° C., the viscosity rapidly increased after about 12 days. After storing 60 days, the viscosity increased to 12 cP and thus the viscosity changed by 140%. As is apparent from these results, the metal colloid of Comparative Example 1 is inferior in stability with time at high temperature. On the other hand, the initial viscosity of the metal colloid of Example 1 was 5 cP, and the viscosity within 60 days was 6 to 6.5 cP when stored at 25 and 40° C. and thus the viscosity changed by about 30% at most. As is apparent from these results, the metal colloid of the present invention is excellent in stability with time even when stored at high temperature.

Example 2

Each of the metal colloids obtained in Synthesis Example 1 and Synthesis Example 7 was mixed with a silica sol to prepare a solution having a colloid concentration of 8% by weight and the solution was coated to form a film, and then the film was fired at 300° C. to form a metal colloidal thin film. Using a metal colloid of a comparative sample prepared by using a protective agent shown in Table 4 below, the same film was formed. Pencil hardness of these metal colloidal thin films thus formed was measured. The results are shown in Table 4.

As is apparent from the results shown in Table 4, all metal colloid thin film of the present invention showed the pencil hardness of 7H or more (no scratching occurs when the pencil hardness is 6H), whereas, the metal colloidal thin film as the comparative sample showed the pencil hardness of 1H or less (scratching occurs when the pencil hardness is 1H). The hardness of the thin film of the present invention did not change even when used under heating.

TABLE 4

| Sample No. | Kind of protective agent | Pencil strength of metal colloidal film |
| --- | --- | --- |
| 1 | γ-mercaptopropyltrimethoxysilane | 7H to 8H |
| 7 | N-β-(aminoethyl)γ-aminopropyltrimethoxysilane | 8H to 9H |
| Comparative sample | Sodium citrate | <1H |

Example 3

With respect to the metal colloidal solution of Example 2, permeability immediately after preparation and permeability after 400 hours were measured. The results are show in FIG. 5 (permeability immediately after preparation) and FIG. 6 (permeability after 400 hours), respectively.

Figure 5:
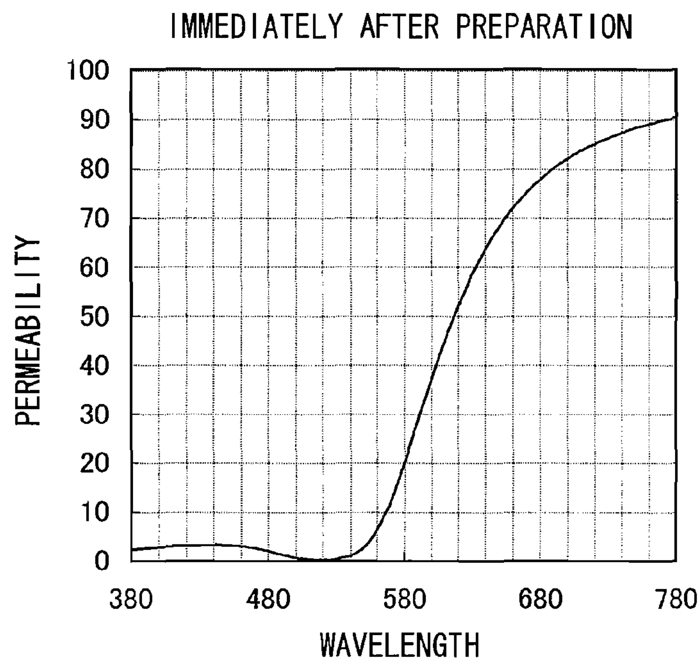
FIG. 5 is a graph showing permeability immediately after the preparation of a metal colloid of Example 3.
Figure 6:
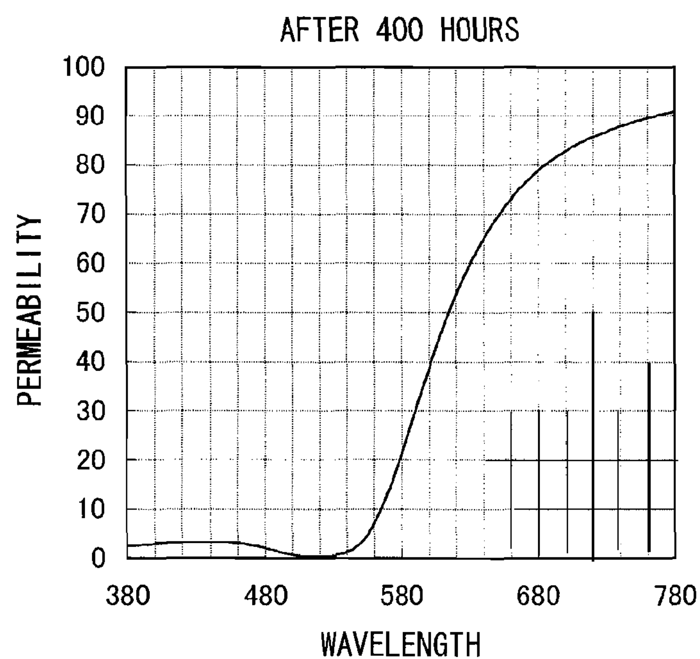
FIG. 6 is a graph showing permeability after use under thermal loading for 400 hours after the preparation of a metal colloid of Example 3.

As is apparent from the results shown in FIG. 5 and FIG. 6, permeability immediately after preparation and permeability after 400 hours hardly changed at a wavelength within a range from 380 to 780 nm and the metal colloidal solution of the present inventional is excellent in stability with time.

With respect to these samples, chromaticity change was also measured. The resulting measuring results are as follows. In a chromaticity coordinate system, the value of the x ordinate was 0.6420 at the initiation of the measurement and the value of the x ordinate was 0.6408 after 400 hours, and thus the x coordinate changed by 0.19%. Also the value of the y ordinate was 0.3428 at the initiation of the measurement and the value of the y ordinate was 0.3443 after 400 hours, and thus the y coordinate changed by 0.44%. As is apparent from these results, the change rate is very small and thus these samples are excellent in stability with time. With respect to other metal colloids, the same test was conducted. As a result, the color tone of all metal colloids changed by 2% or less.

Example 4

Figures 7, 8:
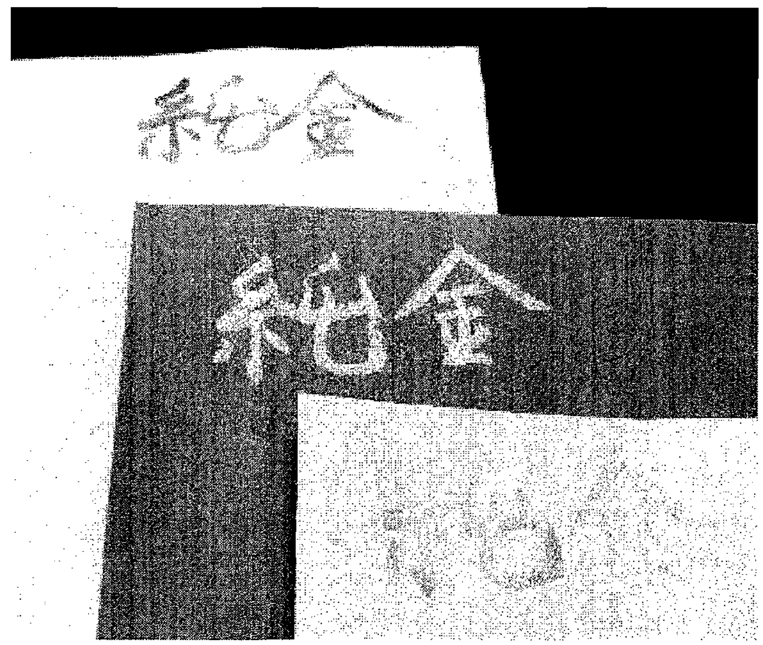
FIG. 7 is a photograph showing a Japanese paper wherein characters are written on the surface using a metal colloid of Example 4.
FIG. 8 is a photograph showing a glass cup wherein patterns are drawn on the surface using a metal colloid of Example 6.

The metal colloids having a concentration of 50% by weight obtained in Synthesis Examples 1 to 27 were prepared and each of the metal colloids having a concentration of 50% by weight was diluted to prepare metal colloids each having a concentration of 5% by weight, 10% by weight, 15% by weight, 20% by weight, 25% by weight, 30% by weight and 40% by weight, respectively. Using each of metal colloids each having a concentration of 5 to 50% by weight, predetermined characters were written on a Japanese paper using a writing brush of India ink, and then air-dried. A photograph of a Japanese paper wherein characters are written on the surface using a metal colloid having a concentration of 30% by weight is shown in FIG. 7. In FIG. 7, a photograph of a paper made of the material other than that of the Japanese paper wherein characters are written on the surface is also shown.

In case of using the metal colloid having a concentration of 30% by weight or more, the written characters showed color tone and metal specular gloss peculiar to metal, and metal was not peeled off even when the surface of the characters are rubbed with a cloth. Also in case of using the metal colloid having a concentration of 25% by weight or less, the characters showed metal specular gloss, but showed color tone which is seemed to be different from the color tone peculiar to metal. After storing the metal colloid at room temperature for 3 weeks, characters were written again on the Japanese paper using the stored metal colloid. Similar to the case before the storage, the written characters showed color tone and metal specular gloss peculiar to metal.

Example 5

A solution was prepared by mixing each of the metal colloids each having a concentration of 5 to 50% by weight used in Example 4 with polyvinyl pyrrolidone, polyvinyl butyral and polyvinyl alcohol in the proportion of 5 to 15% based on the weight of metal. Using each of the metal colloids thus prepared, predetermined characters were written on a Japanese paper using a writing brush of India ink, and then air-dried.

In case of using the metal colloid having a concentration of 25% by weight or more, the written characters showed color tone and metal specular gloss peculiar to metal, and metal was not peeled off even when the surface of the characters are rubbed with a cloth. Also in case of using the metal colloid having a concentration of 20% by weight or less, the characters showed metal specular gloss, but showed color tone which is seemed to be different from the color tone peculiar to metal. After storing the metal colloid at room temperature for 3 weeks, characters were written again on the Japanese paper using the stored metal colloid. Similar to the case before the storage, the written characters showed color tone and metal specular gloss peculiar to metal.

Example 6

Figures 9, 10A:
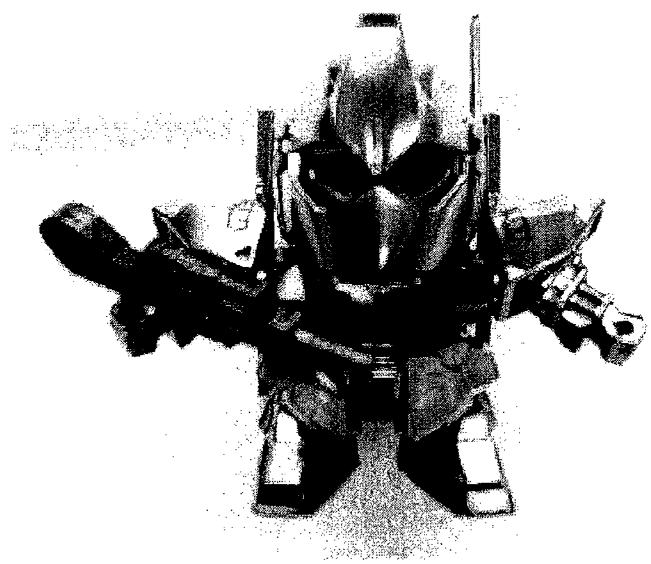
FIG. 9 is a photograph of a coffee cup made of porcelain wherein characters are written on the surface using a metal colloid of Example 6.

First, a glass cup, a ceramic ware, a coffee cup made of porcelain and a plastic plate made of polycarbonate were prepared, respectively. Using the metal colloid prepared in Example 4, predetermined patterns were drawn on the glass cup and the ceramic, respectively. On the side of the coffee cup made of a metporcelain and the surface of the plastic plate made of polycarbonate, predetermined patterns were drawn, respectively. A photograph of a glass cup wherein patterns are drawn on the surface is shown in FIG. 8, and a photograph of a coffee cup made of porcelain wherein characters are written on the surface is shown in FIG. 9.

In case of using the metal colloid having a concentration of 15% by weight or more, the patterns showed color tone and metal specular gloss peculiar to metal, and metal was not peeled off even when the surface of the patterns is rubbed with a cloth. Also in case of using the metal colloid having a concentration of 10% by weight or less, the patterns showed metal specular gloss, but showed color tone which is seemed to be different from the color tone peculiar to metal. After storing the metal colloid at 40° C. for 3 weeks, characters were written again on the ceramic ware, the coffee cup made of porcelain and the plastic plate made of polycarbonate using the stored metal colloid. Similar to the case before the storage, the pattern showed color tone and metal specular gloss peculiar to metal Example 7

First, the metal colloid prepared in Example 4 was coated on the surface of an artificial hair, an artificial eyelash, a plastic model, an amulet case, a skippet, a memorial card, an invitation card, a greeting card, a doll, a Buddhist image, a mortuary tablet, a picture frame, clothes and a woven fabric, respectively. The metal colloid was coated on the artificial nail by a method of spraying using an airbrush, while the metal colloid was coated on the entire surface of the artificial eyelash, the plastic model, the doll and the Buddhist image using a writing brush. Also writing desired characters were written on the mortuary tablet using a wiring brush and the metal colloid was coated only on the frame portion of the picture frame using a writing brush, and desired characters or patterns were drawn on the memorial card, the invitation card, the greeting card, the amulet case, the skippet, clothes and the woven fabric using a writing brush. After coating, the dispersion medium in the metal colloid was sufficiently removed by drying with an air of a dryer to form a metal colloid-containing coat.

Figures 10B, 11A:
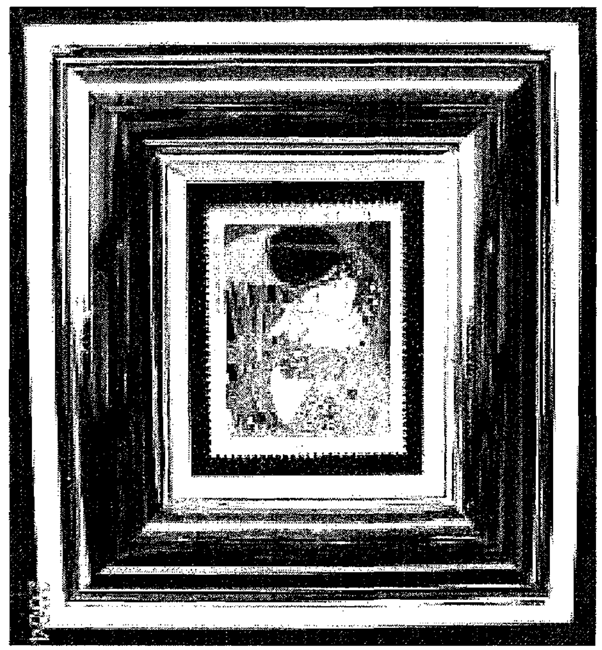
FIG. 10 A is a photograph showing a plastic model, the surface of which is coated with a metal colloid of Example 7.
FIG. 11 A is a photograph showing a ring made of a silver clay, the surface of which is coated with a metal colloid of Example 8

A photograph of a plastic model on which a metal colloid-containing coat is formed is shown in FIG. 10 A and the frame portion is shown in FIG. 10 B, respectively. As is apparent from FIG. 10 A and FIG. 10 B, the metal colloid-containing coat showed metal gloss and color tone peculiar to metal and is excellent in brightness and design properties.

Example 8

First, the metal colloid prepared in Example 4 was coated on the following jewelries. A gold colloid was coated on a ring, a ring made of a silver clay, a pierced earring, an earring, a bracelet, a necklace, a key holder and an ornamental hairpin using a writing brush, and the gold colloid was coated on a watch, a hairpin, a broach and a tiepin by a method of spraying using an airbrush. A ring made of a silver clay, an earring and a broach on which a metal colloid-containing coat is formed are shown in FIG. 11 A, FIG. 11 B and FIG. 11 C, respectively.

Figure 11B:
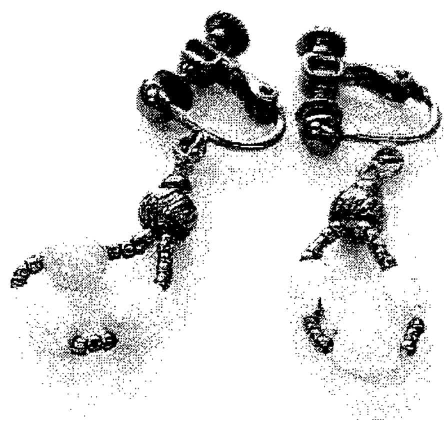
Figure 11C:
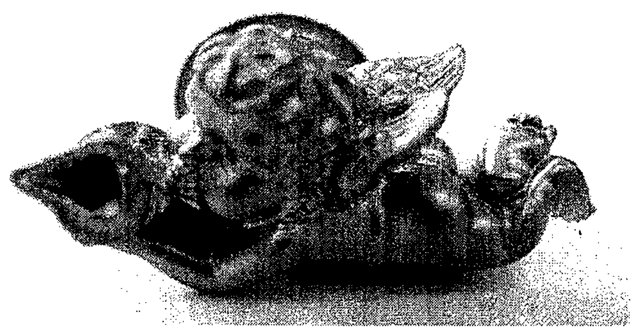

As is apparent from FIG. 11 A, FIG. 11 B and FIG. 11 C, the metal colloid-containing coat of jewelries showed metal gloss and color tone peculiar to metal and is excellent in brightness and design properties.

Example 9

The metal colloid prepared in Example 4, a natural nail and an artificial nail were prepared, respectively. By a method of coating the metal colloid using a writing brush for manicure shown in FIG. 12, the metal colloid was coated on the surface of the natural nail and the artificial nail. After coating, the dispersion medium in the metal colloid was sufficiently removed by drying with an air of a dryer to form a metal colloid-containing coat. A natural nail on which a metal colloid-containing coat is formed by a coating method is shown in FIG. 13.

Figures 12, 13:
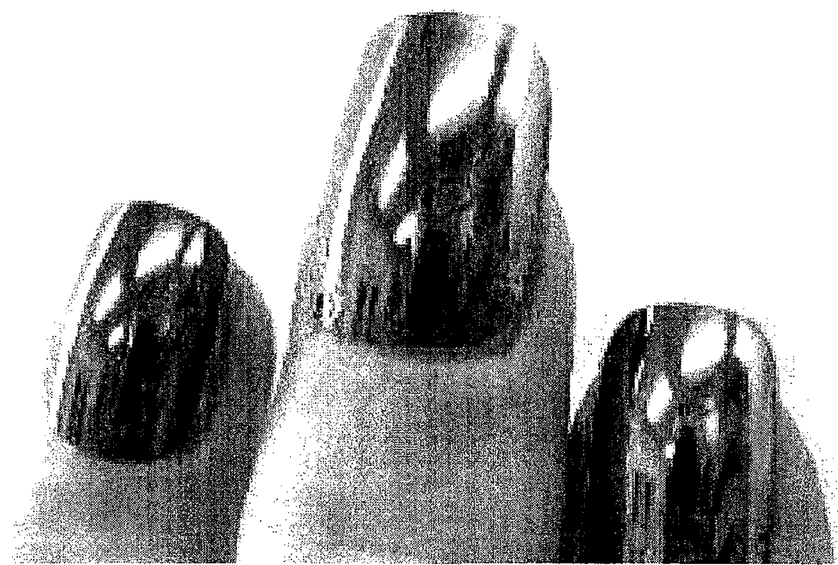
FIG. 12 is a photograph showing a method of coating a metal colloid using a writing brush for manicure of Example 9.
FIG. 13 is a photograph showing finger nails wherein a metal colloid-containing coat is formed on the surface using the coating method of FIG. 12.

As is apparent from FIG. 13, the metal colloid-containing coat formed on the surface of the natural nail and the artificial nail showed golden gloss and color tone peculiar to gold and had a metal specular surface which is excellent in smoothness.

Example 10

Figure 14:
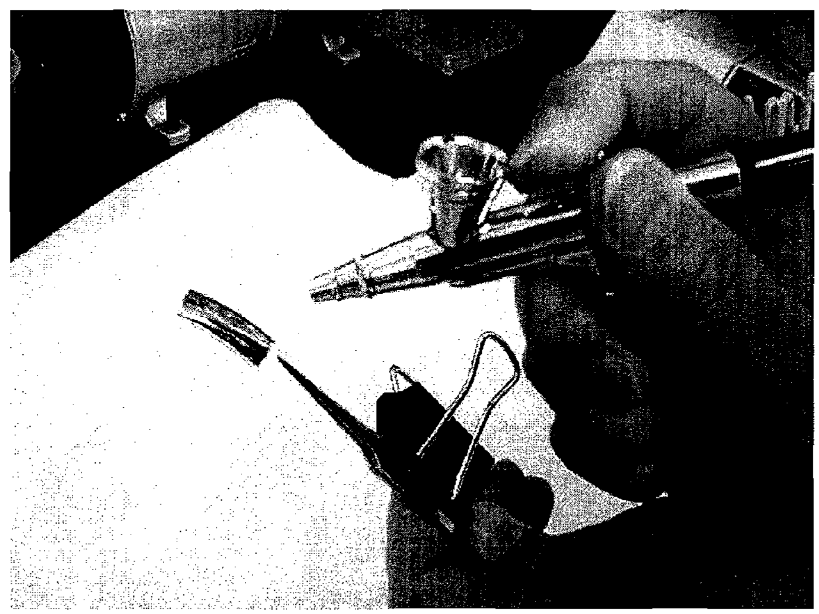
FIG. 14 is a photograph showing a method of spraying a metal colloid using an airbrush for manicure of Example 10.

Using a method of spraying a metal colloid using an airbrush for manicure shown in FIG. 14, the metal colloid prepared in Example 4 was sprayed over the surface of a natural nail and the surface of an artificial nail. After spraying, the dispersion medium in the metal colloid was sufficiently removed by drying with an air of a dryer to form a metal colloid-containing coat. A natural nail on which a metal colloid-containing coat is formed by a spraying method is shown in FIG. 15.

Figure 15:
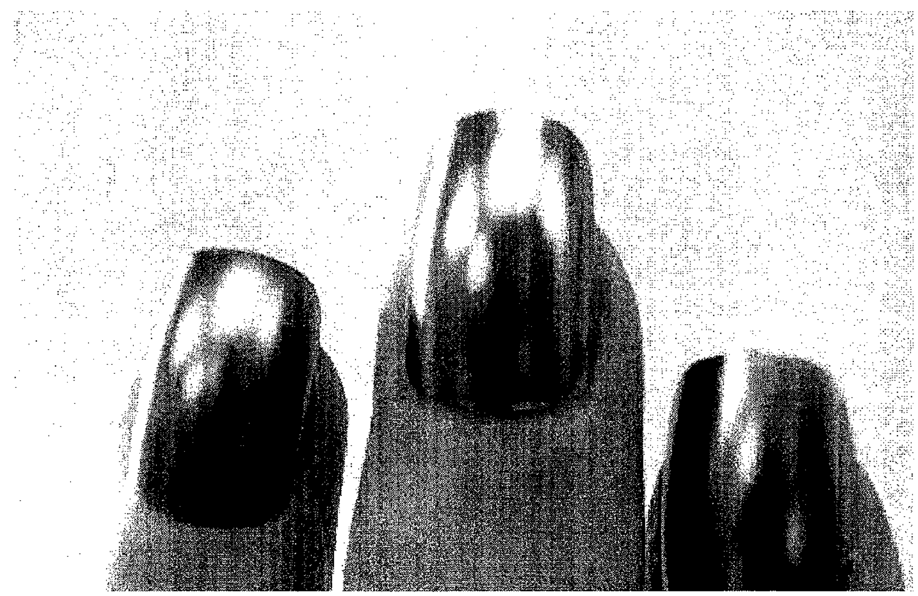
FIG. 15 is a photograph showing finger nails wherein a metal colloid-containing coat is formed on the surface using the spraying method of FIG. 14.

As is apparent from FIG. 15, the metal colloid-containing coat formed on the surface of the natural nail and the artificial nail showed golden gloss and color tone peculiar to gold and had a metal specular surface which has matted gloss and is excellent in smoothness, unlike the coat of Example 9 formed by coating using the writing brush.

Example 11

First, in the same manner as in Example 9, the metal colloid prepared in Example 4 was coated on the surface of a natural nail and the surface of an artificial nail using a writing brush for manicure. After coating, the dispersion medium in the metal colloid was sufficiently removed by drying with an air of a dryer to form a metal colloid-containing coat. Then, a top coating agent was coated on the metal colloid-containing coat thus formed by a wet-on-wet coating method and this top coating prevented the metal colloid-containing coat from being peeled off with ease. The metal colloid-containing coat formed on the surface of the artificial nail showed golden gloss and color tone peculiar to gold and had a metal specular surface which is excellent in smoothness, similar to the case of the coat obtained in Example 9.

Example 12

First, an under coat layer was formed on the surface of an artificial nail. In the same manner as in Example 9, the metal colloid prepared in Example 4 was coated on the surface of the under coat layer using a writing brush for manicure. The metal colloid-containing coat formed on the surface of the artificial nail showed golden gloss and color tone peculiar to gold and had a metal specular surface which is excellent in smoothness, similar to the case of the coats obtained in Example 9 and Example 11.

Example 13

First, an under coat layer was formed on the surface of an artificial nail. In the same manner as in Example 9, the metal colloid prepared in Example 4 was coated on the surface of the under coat layer using a writing brush for manicure. After coating, the dispersion medium in the metal colloid was sufficiently removed by drying with an air of a dryer to form a metal colloid-containing coat. Then, a top coating agent was coated on the metal colloid-containing coat thus formed by a wet-on-wet coating method and this top coating prevented the metal colloid-containing coat from being peeled off with ease. The metal colloid-containing coat formed on the surface of the artificial nail showed golden gloss and color tone peculiar to gold and had a metal specular surface which is excellent in smoothness, similar to the case of the coats obtained in Example 9, Example 11 and Example 12.

Example 14

In the same manner as in Example 13, except that the metal colloid was coated only at the tip portion of the nail using an airbrush, a metal colloid-containing coat was formed on the surface of an artificial nail. In the same manner as in Example 13, except that desired patterns were drawn on the surface of the nail using a writing brush for manicure in case of coating the metal colloid, a metal colloid-containing coat was formed on the surface of an artificial nail. The artificial nail coated with the metal colloid only at the tip portion using an airbrush and the artificial nail wherein desired patterns are drawn on the surface of the nail using a writing brush for manicure showed color tone peculiar to metal and were excellent in design properties, similar to Example 9 and Examples 11 to 13.

Example 15

In the same manner as in Example 13, except that the metal colloid prepared in Example 4 contains 0.5 to 3% of fine metal particles having an average particle size of 1 to 10 nm, a metal colloid-containing coat was formed on the surface of an artificial nail. The resulting artificial nail on which the metal colloid-containing coat is formed is shown in FIG. 16.

Figures 16, 17A:
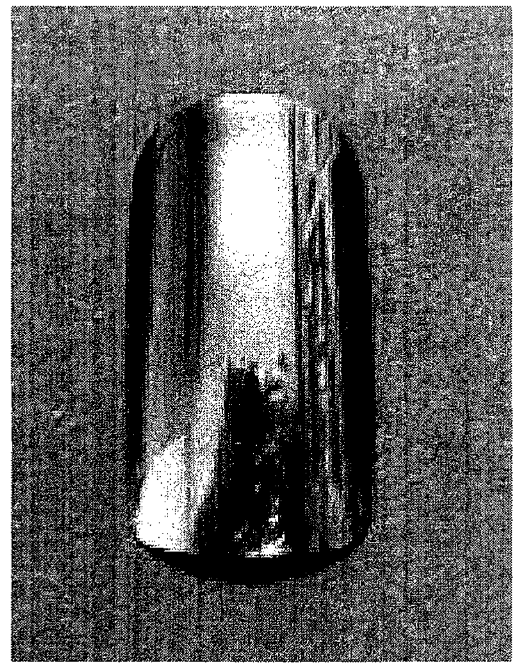
FIG. 16 is a photograph showing artificial nails of Example 15 wherein a metal colloid-containing coat showing a pink gold color tone on the surface is formed.

As is apparent from FIG. 16, the metal colloid-containing coat formed on the surface of the artificial nail shows a pink gold color tone and is excellent in design properties.

Example 16

In the same manner as in Example 13, except that the metal colloid obtained in Synthesis Example 19 was used, a metal colloid-containing coat was formed on the surface of an artificial nail. The resulting artificial nail on which the metal colloid-containing coat is formed is shown in FIG. 17 A.

As is apparent from FIG. 17 A, the coat formed on the surface of the artificial nail has a metal specular surface and is excellent in smoothness, and also shows a yellow gold color tone and is excellent in design properties.

Example 17

In the same manner as in Example 13, except that the metal colloid obtained in Synthesis Example 20 was used, a metal colloid-containing coat was formed on the surface of an artificial nail. The resulting artificial nail on which the metal colloid-containing coat is formed is shown in FIG. 17 B.

As is apparent from FIG. 17 B, the coat formed on the surface of the artificial nail has a metal specular surface and is excellent in smoothness, and also shows a green gold color tone and is excellent in design properties.

Example 18

In the same manner as in Example 13, except that the metal colloid obtained in Synthesis Example 21 was used, a metal colloid-containing coat was formed on the surface of an artificial nail. The resulting artificial nail on which the metal colloid-containing coat is formed is shown in FIG. 17 C.

As is apparent from FIG. 17 C, the coat formed on the surface of the artificial nail has a metal specular surface and is excellent in smoothness, and also shows a red gold color tone and is excellent in design properties.

Example 19

In the same manner as in Example 13, except that the metal colloid obtained in Synthesis Example 22 was used, a metal colloid-containing coat was formed on the surface of an artificial nail. The resulting artificial nail on which the metal colloid-containing coat is formed is shown in FIG. 17D.

Figure 17B:
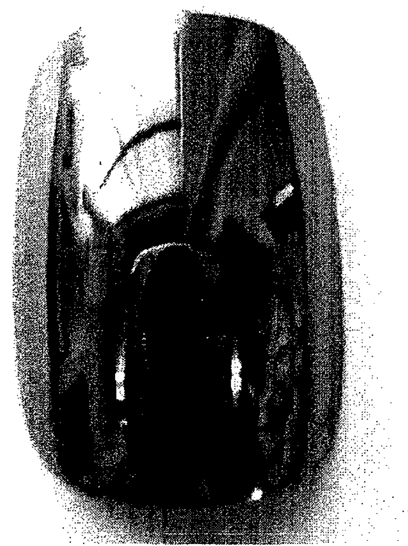
FIG. 17 A is a photograph showing artificial nails of Example 16 wherein a metal colloid-containing coat showing a yellow gold color tone on the surface is formed.
FIG. 17D is a photograph showing artificial nails of Example 19 wherein a metal colloid-containing coat showing a pink gold color tone on the surface is formed.
FIG. 17E is a photograph showing artificial nails of Example 20 wherein a metal colloid-containing coat showing a white gold color tone on the surface is formed.
Figure 17C:
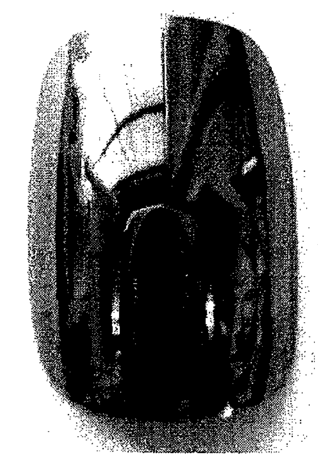
Figures 17D, 17E:
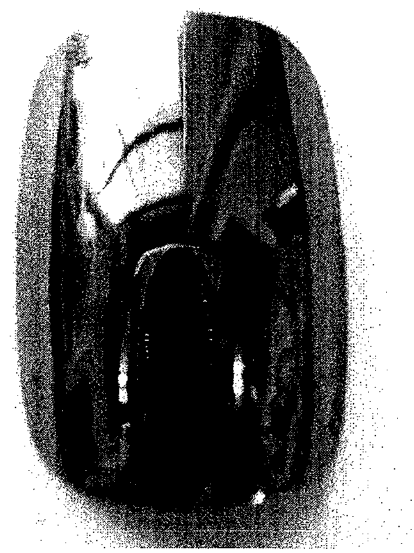

As is apparent from FIG. 17D, the coat formed on the surface of the artificial nail has a metal specular surface and is excellent in smoothness, and also shows a pink gold color tone and is excellent in design properties.

Example 20

In the same manner as in Example 13, except that the metal colloid obtained in Synthesis Example 23 was used, a metal colloid-containing coat was formed on the surface of an artificial nail. The resulting artificial nail on which the metal colloid-containing coat is formed is shown in FIG. 17E.

As is apparent from FIG. 17E, the coat formed on the surface of the artificial nail has a metal specular surface and is excellent in smoothness, and also shows a white gold color tone and is excellent in design properties.

Example 21

First, an under coating agent was coated on the surface of an artificial nail and then dried to form an under coat layer. In the same manner as in Example 9, the metal colloid prepared in Example 4 was coated on the surface of the under coat layer using a writing brush for manicure. The dispersion medium in the metal colloid was removed by drying with an air of a dryer to form a metal colloid-containing coat. Then, a top coating agent was coated on the metal colloid-containing coat thus formed and, before completely drying the top coating agent, a lame agent as a material was scattered at desired points and diamond natural stones and pink sapphire natural stones were set thereon, and then these materials were fixed by pressing and immobilized by drying the top coating agent with an air of a dryer. Immobilization of these materials was enhanced by further coating the top coating agent. Brightness and design properties were improved by using the metal colloid-containing coat in combination of the lame agent and natural gems of diamond and pink sapphire.

Example 22

First, the metal colloid prepared in Example 4 was coated only at the tip portion of an artificial nail using a writing brush for manicure. After coating, the dispersion medium in the metal colloid was removed by drying with an air of a dryer to form a metal colloid-containing coat. Then, a top coating agent was coated on the metal colloid-containing coat thus formed and, before completely drying the top coating agent, pearl and diamond natural stones as materials were arranged at the desired points, and then these materials were fixed by pressing and immobilized by drying the top coating agent with an air of a dryer. Immobilization of these materials was enhanced by further coating the top coating agent. The resulting artificial nail on which the metal colloid-containing coat is formed is shown in FIG. 18 A.

Figure 18A:
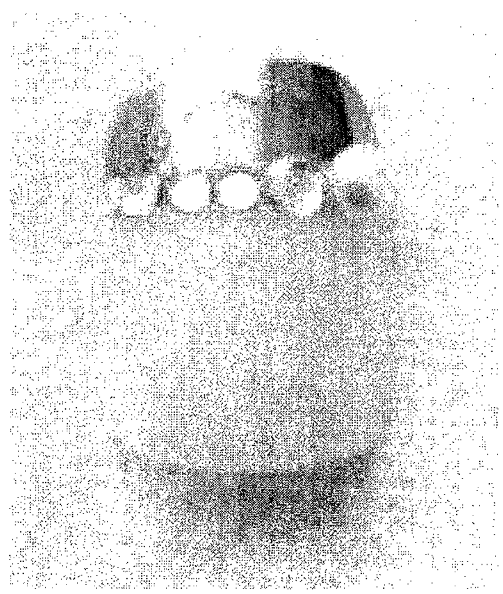
FIG. 18 A is a photograph showing artificial nails of Example 22 wherein a metal colloid-containing coat and natural gems of pearl and diamond are formed in combination on the surface.
Figure 18B:
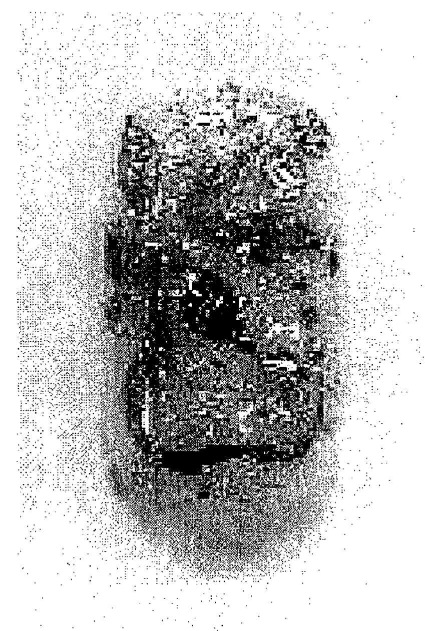

As is apparent from FIG. 18 A, brightness and design properties were improved by using the metal colloid-containing coat formed only at the tip portion of the nail in combination with pearl and natural gems of diamond.

Example 23

First, desired patterns were drawn on the surface of an artificial nail with the metal colloid prepared in Example 4 using a writing brush for manicure. After drawing, the dispersion medium in the metal colloid was removed by drying with an air of a dryer to form a metal colloid-containing coat. Then, a top coating agent was coated on the entire surface of a nail and, before completely drying the top coating agent, a gold foil powder and diamond and pink sapphire natural stones as materials were set at the desired points, and then these materials were fixed by pressing and immobilized by drying the top coating agent with an air of a dryer. Immobilization of these materials was enhanced by further coating the top coating agent. The resulting artificial nail on which the metal colloid-containing coat is formed is shown in FIG. 18 B.

As is apparent from FIG. 18 B, brightness and design properties were improved by using the metal colloid-containing coat in combination with the gold foil powder and natural gems of diamond and pink sapphire.

Example 24

First, a coating solution of an acrylic resin was coated on one surface of a base material 2 made of a releasable synthetic paper to form a surface protective layer 4. Then, the gold colloid prepared in Example 4 was coated on the surface protective layer 4 to form a metal colloid-containing coat layer 5. Furthermore, a coating solution of a hot melt type resin was coated on the metal colloid-containing coat layer 5 to form an adhesive layer 6, thus obtaining a transfer sheet 1 wherein a transfer layer 3 comprising the surface protective layer 4, the metal colloid-containing coat layer 5 and an adhesive layer 6 is formed on the base material 2 shown in FIG. 19.

Example 25

In the same manner as in Example 24, except that characters or patterns were drawn by an ink jet printer to form a metal colloid-containing coat layer 5, a transfer sheet was produced.

Example 26

Each of the transfer sheets of Example 24 and Example 25 was thermally transferred under pressure to a paper, clothes, a leather and a glass to form a metal colloid-containing coat on the surface. The metal colloid-containing coat showed metal gloss and color tone peculiar to metal and was excellent in brightness. The coat was not peeled off even when rubbed with fingers. The method for thermal transfer under pressure can be conducted by a conventionally known method.

Example 27

A plasma-treated glass sheet measuring 150 mm×150 mm×1 mm was prepared and an ink tank of an ink jet printer was filled with the Au colloid having a concentration of 50% by weight obtained in Synthesis Example 13 of Example 4, and then 5 golden gloss colored lines having a line width of about 2 mm and a length of 100 mm were drawn on the glass sheet. The drawn glass sheet was dried at room temperature and the electrical resistance value of the golden gloss colored line was measured. As a result, it was $9.6\times10^{-6}$ Ω·cm.

Example 28

A plasma-treated glass sheet measuring 150 mm×150 mm×1 mm was prepared and an ink tank of an ink jet printer was filled with the Au colloid having a concentration of 50% by weight obtained in Synthesis Example 5 of Example 4, and then 5 golden gloss colored lines having a line width of about 2 mm and a length of 100 mm were drawn on the glass sheet. The drawn glass sheet was fired in an atmospheric air at 300° C. for 10 minutes and the electrical resistance value of the golden gloss colored line was measured. As a result, it was $2.5\times10^{-6}$ Ω·cm.

Example 29

An alumina sheet measuring 50 mm×50 mm×1.0 mm was prepared and spin-coated with the Ru colloid having a concentration of 40% by weight obtained in Synthesis Example 16 of Example 4 under the conditions of a rotating speed of 200 rpm and 3 minutes to form a coat on the surface of the alumina sheet. The alumina sheet with the coat formed thereon was fired in an atmospheric air at 350° C. for one minute and then air-cooled. After cooling to room temperature, the electrical resistance value of the resulting coat was measured. As a result, the resistance value was $7.1\times10^{-4}$ Ω·cm.

Example 30

An alumina sheet measuring 50 mm×50 mm×1.0 mm was prepared and screen printing was conducted using the Pt colloid having a concentration of 50% by weight obtained in Synthesis Example 17 of Example 4 to form a coat measuring 10 mm×25 mm on the surface of the alumina sheet. The alumina sheet with the coat formed thereon was fired in an atmospheric air at 400° C. for 10 minutes and then air-cooled. After cooling to room temperature, the electrical resistance value of the resulting coat was measured. As a result, the resistance value was $4.9\times10^{-4}$ Ω·cm.

Example 31

An alumina sheet measuring 50 mm×50 mm×1.0 mm was prepared and spin-coated with the Cu colloid having a concentration of 30% by weight obtained in Synthesis Example 18 of Example 4 under the conditions of a rotating speed of 200 rpm and 3 minutes using to form a coat on the surface of the alumina sheet. The alumina sheet with the coat formed thereon was fired in a 2% hydrogen-containing argon gas atmosphere at 300° C. for 10 minutes and then air-cooled. After cooling to room temperature, the electrical resistance value of the resulting coat was measured. As a result, the resistance value was $2.5\times10^{-5}$ Ω·cm.

Example 32

An alumina sheet measuring 50 mm×50 mm×1.0 mm was prepared and offset printing was conducted using the Ni colloid having a concentration of 30% by weight obtained in Synthesis Example 24 of Example 4 to form a coat measuring 10 mm×25 mm on the surface of the alumina sheet. The alumina sheet with the coat formed thereon was fired in a 2% hydrogen-containing argon gas atmosphere at 450° C. for one minute and then air-cooled. After cooling to room temperature, the electrical resistance value of the resulting coat was measured. As a result, the resistance value was $5.5\times10^{-5}$ Ω·cm.

Example 33

An alumina sheet measuring 50 mm×50 mm×1.0 mm was prepared and spin-coated with the Ni/Zn colloid having a concentration of 30% by weight obtained in Synthesis Example 25 of Example 4 under the conditions of a rotating speed of 200 rpm and 3 minutes using to form a coat on the surface of the alumina sheet. The alumina sheet with the coat formed thereon was fired in a 2% hydrogen-containing argon gas atmosphere at 450° C. for 10 minutes and then air-cooled. After cooling to room temperature, the electrical resistance value of the resulting coat was measured. As a result, the resistance value was $9.3\times10^{-5}$ Ω·cm.

Example 34

An alumina sheet measuring 50 mm×50 mm×1.0 mm was prepared and spray-coated with the Rh colloid having a concentration of 30% by weight obtained in Synthesis Example 26 of Example 4 to form a coat on the surface of the alumina sheet. The alumina sheet with the coat formed thereon was fired in an argon gas atmosphere at 400° C. for 10 minutes and then air-cooled. After cooling to room temperature, the electrical resistance value of the resulting coat was measured. As a result, the resistance value was $2.5\times10^{-5}$ Ω·cm.

Example 35

An alumina sheet measuring 50 mm×50 mm×1.0 mm was prepared and spin-coated with the Ir colloid having a concentration of 30% by weight obtained in Synthesis Example 27 of Example 4 under the conditions of a rotating speed of 200 rpm and 3 minutes to form a coat on the surface of the alumina sheet. The alumina sheet with the coat formed thereon was fired in an argon gas atmosphere at 400° C. for 10 minutes and then air-cooled. After cooling to room temperature, the electrical resistance value of the resulting coat was measured. As a result, the resistance value was $4.5\times10^{-5}$ Ω·cm.

Example 36

An alumina sheet measuring 50 mm×50 mm×1 mm was prepared and screen printing was conducted using the Au colloid having a concentration of 50% by weight obtained in Synthesis Example 5 of Example 4 to form a coat measuring 10 mm×25 mm on the surface of the alumina sheet. The alumina sheet with the coat formed thereon was fired in an atmospheric air at 15° C. for one hour and then air-cooled. After cooling to room temperature, the electrical resistance value of the resulting coat was measured. As a result, the resistance value was $1.3\times10^{-4}$ Ω·cm.

Example 37

An alumina sheet measuring 50 mm×50 mm×1 mm was prepared and screen printing was conducted using the Au colloid having a concentration of 50% by weight obtained in Synthesis Example 5 of Example 4 to form a coat measuring 10 mm×25 mm on the surface of the alumina sheet. The alumina sheet with the coat formed thereon was fired in an atmospheric air at 350° C. for one minute and then air-cooled. After cooling to room temperature, the electrical resistance value of the resulting coat was measured. As a result, the resistance value was $2.7\times10^{-6}$ Ω·cm.

Comparative Example 2

First, sodium citrate was prepared as a protective agent and a reducing agent and 45 g of sodium citrate and 15 g of chlorauric acid were dissolved in 240 g of deionized water, followed by stirring under reflux at 100° C. for one hour. The resulting reddish violet metal colloid was cooled and then desalted by an ultrafiltration method to obtain metal colloidal particles of gold. The resulting metal colloidal particles were added to a water solvent to prepare a metal colloid having a concentration of 10% by weight of a water medium. The above synthesis process was repeated three times to obtain a metal colloid in a total amount of 150 g. A trial of synthesizing a metal colloid having a concentration of more than 10% by weight was made. However, the resulting synthesized product could not be colloidized because it is unstable and is aggregated. When using a medium other than water, the metal colloid was aggregated.

Predetermined characters were written on a Japanese paper by a writing brush for India ink using a metal colloid having a concentration of 10% by weight of a water medium, and then air-dried. However, the characters written on the Japanese paper showed no gloss because of reddish violet blur occurred. Then, a solution was prepared by mixing the metal colloid with polyvinyl alcohol in the proportion of 5 to 15% based on the weight of metal. Predetermined characters were written on the Japanese paper by this mixed solution using a writing brush for India ink, and then air-dried. However, the characters written on the Japanese paper showed no gloss because of reddish violet blur occurred.

In the same manner as in Example 6, predetermined patterns were written on a glass cup and a ceramic ware using the mixed solution. Also predetermined characteristics were written on the side of a coffee cup made of porcelain and the surface of a plastic plate made of polycarbonate. In all base materials, the coat formed by coating once with the mixed solution showed metallic reflection gloss, but showed a purplish gold color which is different from the color tone of god. When wet-on-wet coating is conducted three times, the resulting coat showed gold-like metal gloss, but showed color tone which is different from that peculiar to gold. When the coated surface was rubbed, the coat was peeled off with ease. The same coating operation was conducted using a mixed solution prepared by mixing the metal colloid with a predetermined amount of a solution containing polyvinyl alcohol and a predetermined amount of solutions each containing silane compounds A to C. However, the resulting coat showed color tone which is different from that of gold and gloss disappeared. When the coat was rubbed, it was peeled off with ease. These metal colloids were completely aggregated within 2 days.

Example 38

An example of a cartridge for pen filled with the metal colloid of the present invention as an ink, and a pen connected with the cartridge for pen will now be described.

As shown in FIG. 20 A, a cartridge 10 for pen is composed of a tubular body 11 having a closed lower portion, a lid portion 13 which is joined with the upper portion of the tubular body 11 and is provided with a continuous hole at center, and a spherical plug 14 inserted loosely into the continuous hole of the lid portion 13, and the tubular body 11 is filled with the metal colloid 12 prepared in Example 4 of the present invention. The tubular body 11 and the lid portion 13 are preferably made of a synthetic resin, and the spherical plug 14 is preferably made of metal. In the cartridge 10 for pen, when the spherical plug 14 inserted loosely is pushed up into the cartridge in the state where the lid portion 13 faces downward or obliquely downward, a gap is formed between the lid portion 13 and the spherical plug 14 and the metal colloid is discharged from the gap due to gravity.

As shown in FIG. 20 B, a pen 20 comprising the cartridge 10 for pen incorporated thereinto is composed of a cylindrical upper shaft barrel 21, a cylindrical lower shaft barrel 22, the upper end of which can be connected to the lower end of the upper shaft barrel 21, and a tip 26 which is connected to the other end of the lower shaft barrel 22. The inner wall of the lower shaft barrel 22 is provided with a connection portion 23 which loosely inserts the cartridge 10 for pen and contacts with the lid portion 13, thereby to push up the spherical plug 14 into the cartridge 10 for pen. In the connection portion 23, there is provided a core portion 24 capable of being impregnated with the metal colloid discharging from the cartridge 10 for pen due to gravity while protruding the other end of the lower shaft barrel 22 when the cartridge 10 for pen is connected to the connection portion 23 and the spherical plug 14 is pushed up by the connection portion 23. The tip 26 connected to the other end of the lower shaft barrel 22 serves to eject the metal colloid, with which the core portion 24 is impregnated, from the tip. The upper shaft barrel 21, the lower shaft barrel 22 and the connection portion 23 are preferably made of a synthetic resin. The core portion 24 is preferably made of a synthetic resin having a structure that pores capable of being impregnated with the metal colloid are formed.

The cartridge 10 for pen is connected to the pen 20 by contacting the lid portion 13 of the cartridge with the connection portion 23 and pushing the connection portion 23 and the plug 14 into the cartridge 10 for pen. In that case, the metal colloid 12 filled into the cartridge 10 is discharged from the gap between the lid portion 13 and the spherical plug 14 and thus the core portion 24 is impregnated with the metal colloid, which is supplied to the tip 26 through the core portion 24. The pen comprising the cartridge 10 for pen connected thereto is easy to draw and was capable of drawing smoothly. This pen is very advantageous to write desired characters and to draw predetermined patterns on the desired base material, and the characters and patterns drawn by the pen showed metal gloss and color tone peculiar to metal and were excellent in brightness.

Example 39

An example of a disposable ampul filled with the metal colloid of the present invention will now be described.

As shown in FIG. 21, a disposable ampul 30 is composed of a tubular body 31 having a closed lower portion, a cut portion 33 joined with the upper portion of the tubular body 31, and a lid portion 32. The cut portion 33 is provided with a smaller width than that of the tubular body 31 and the lid portion 32 so that it can be cut by a hand operation. The tubular body 31, the lid portion 32 and the cut portion 33 are preferably made of a synthetic resin. The disposable ampul 30 has a structure that a metal colloid 34 is sealed by thermal contact bonding of the cut portion 33 and the lid portion 32 after filling the tubular body 31 with a metal colloid 34 prepared in Example 4 of the present invention.

In the disposable ampul 30 thus obtained, the lid portion 32 can be easily cut from the cut portion 33 through the lever rule by laterally rotating the lid portion 32 and the cut surface is communicated with the inside of the tubular body 31. The metal colloid filled in the tubular body 31 can be used after taking out from the communicated portion.

Example 40

Figure 22:
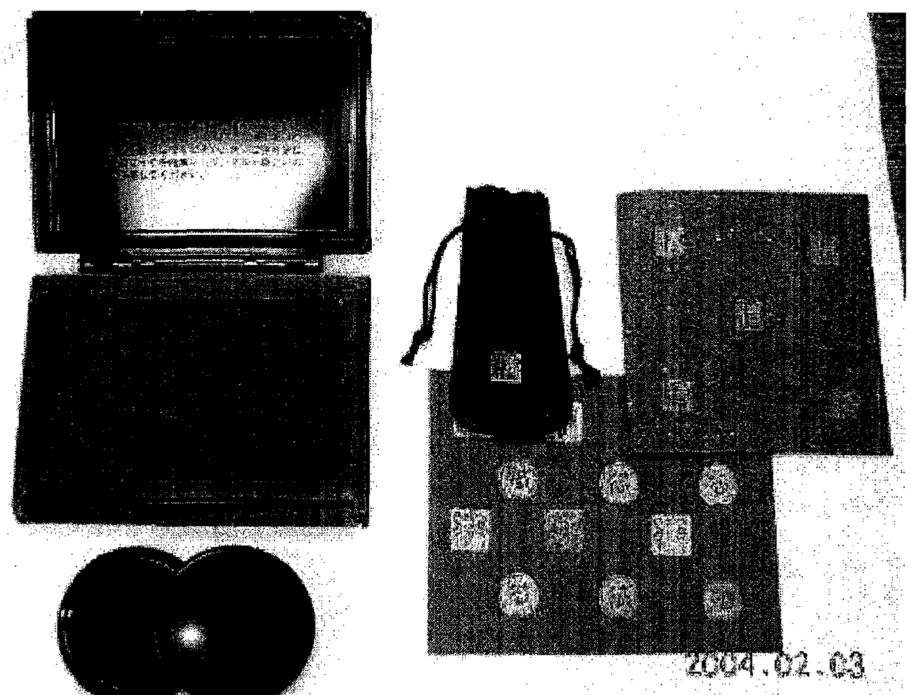
FIG. 22 is a photograph showing a stamp pad and a seal impression pad which are made by impregnating with a metal colloid of Example 40.
Figures 23, 24:
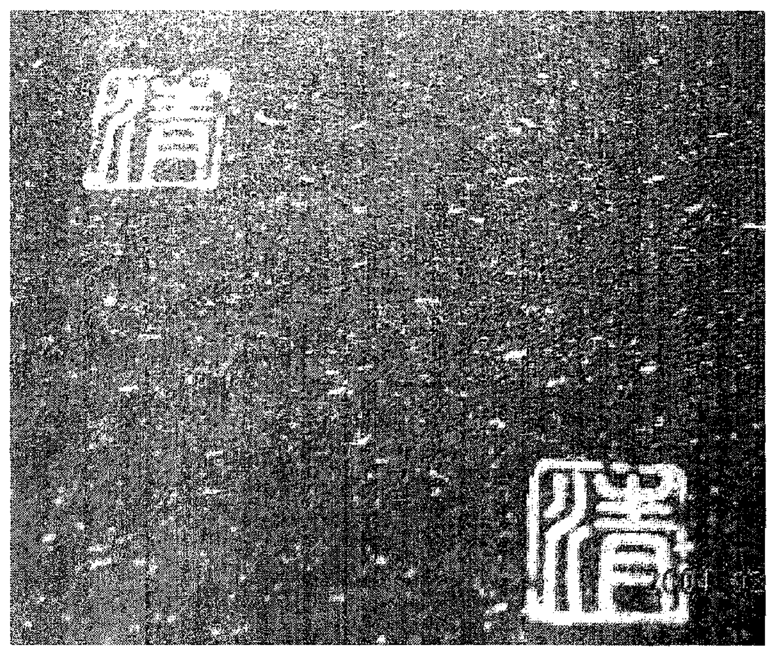
FIG. 23 is a photograph showing a skippet provided with patterns using the stamp pad of FIG. 22.
FIG. 24 is a graph showing a paper provided with patterns using the seal impression pad of FIG. 22.

A stamp pad and a seal impression pad were produced by sufficiently impregnating with the metal colloid prepared in Example 4 having a concentration of 30% by weight. Photographs of the resulting stamp pad and seal impression pad are shown in FIG. 22. A skippet and a card wherein patterns are formed using the stamp pad and the seal impression pad are also shown in FIG. 23 and FIG. 24. As is apparent from FIG. 23 and FIG. 24, the patterns made of the metal colloid formed by using the stamp pad or seal impression pad showed color tone and metal gloss peculiar to gold.

Example 41

Figures 25, 26A:
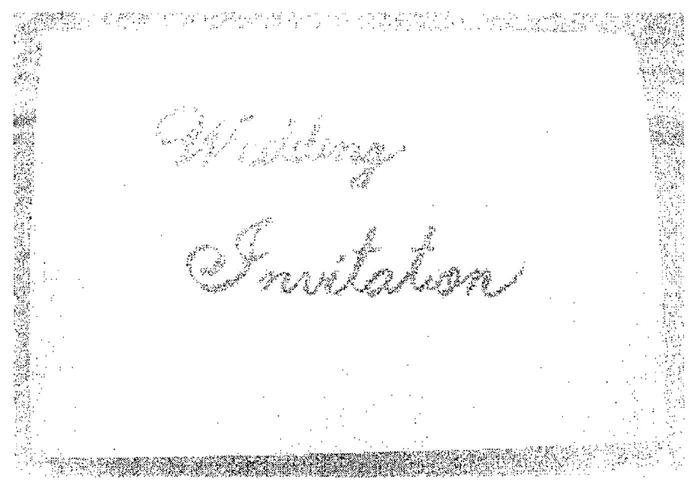
FIG. 25 is a photograph showing leather wallet, a business card and a greeting card wherein a picture is drawn by an ink jet printer apparatus using a metal colloid of Example 41 as an ink.

Using the metal colloid prepared in Example 4 having a concentration of 30% by weight, a spiral scoring test was conducted by an ink jet printer apparatus. As the base material, a paper, a leather and a lumber were used. Using the paper, a business card, a greeting card, a memorial card and an invitation card were produced. In case of using the leather, a leather wallet was drawn. In case of using the lumber, desired characters were written on a mortuary tablet. A photograph of a business card, a greeting card and a leather wallet wherein a metal colloid-containing coat is formed is shown in FIG. 25. As is apparent from FIG. 25, the patterns written by an ink jet printer apparatus using the metal colloid showed color tone and metal gloss peculiar to gold.

Example 42

Using the metal colloid prepared in Example 4 as an ink, characters and patterns were drawn on a colored paper by a writing brush. The characters and patterns showed metal gloss and color tone peculiar to metal and were excellent in brightness. In case of drawing characters or patterns, a pen filled with the metal colloid described in Example 28 as an ink may be used.

Example 43

Using the metal colloid prepared in Example 4 as an ink, a hand print and a foot print were formed on a colored paper. The hand print and the foot print showed metal gloss and color tone metal peculiar to metal and were excellent in brightness.

Example 44

First, a paper wherein patterns are written on the surface by a commercially available black ink using a seal impression and a stamp, a colored paper wherein characters and patterns are drawn on the surface using a black pen, and a colored paper wherein a hand print and a foot print are formed using a black ink were prepared. Using an image scanner, the surface of the paper and that of the colored paper were scanned and the resulting image data were inputted into a computer. By an ink jet printer using the metal colloid of the present invention as an ink, image data were printed on the paper and the colored paper based on the inputted image data. Characters and patterns printed on the paper and the colored paper using the metal colloid of the present invention showed the same shape as that of black colored characters and patterns drawn and also showed metal gloss and color tone peculiar to metal and were excellent in brightness.

In Example 44, using the image scanner, the surface of the paper and that of the colored paper were scanned and the resulting image data were inputted into a computer and then printed using the ink jet printer. Using the image scanner, not only base papers such as paper and colored paper, but also a photograph of these base papers, and a print and a publication in which these patterns and characters are described may be scanned and the resulting image data may be inputted into a computer and directly printed using an ink jet printer.

Synthesis Example 28

Chlorauric acid was prepared as a metal salt used as a main component of metal particles, silver nitride and copper acetate were prepared as a metal salt used as an accessory component, γ-aminopropyltriethoxysilane was prepared as a protective agent precursor, and dimethylamineborane was prepared as a reducing agent, respectively. First, chlorauric acid, silver nitride and copper acetate were dissolved in methanol so as to adjust the metal concentration to 4.0% by weight and to adjust the metal weight ratio Au:Ag:Cu in the metal concentration to 6:2:1. Then, the metal solution prepared previously by dissolving the metal salt was gradually added to 8.00 g of γ-aminopropyltriethoxysilane and 12.00 g of acetylacetone to prepare a mixed solution. To the mixed solution, an appropriate amount of dimethylamineborane as the reducing agent was added. The reduction reaction was conducted while maintaining the temperature of the mixed solution at 60° C. and stirring the mixed solution using a magnetic stirrer. After the completion of the reductive reaction, the mixed solution was cooled to room temperature. After cooling, the mixed solution was desalted by an ultrafiltration method and the concentration was adjusted by appropriately adding water to obtain a metal colloidal solution having a concentration of 50% by weight, containing water as a dispersion medium.

Protective agent molecules constituting metal colloidal particles in the resulting metal colloid were subjected to TOF-SIMS analysis. By TOF-SIMS analysis, cluster ions comprising Au and CN were predominantly detected. As is apparent from the results of TOF-SIMS analysis and NMR (C, H) analysis, the protective agent particles are coordination-modified on the surface of metal particles by nitrogen. The content of the accessory component in the metal particles was examined and was found to be 30% by weight. The silver content in the accessory component was examined and was found to be 60% by weight.

Synthesis Examples 29

Chlorauric acid was prepared as a metal salt used as a main component of metal particles, silver nitride, copper acetate and palladium nitrate were prepared as a metal salt used as an accessory component, 3-aminopropanol was prepared as a protective agent precursor, and sodium borohydride was prepared as a reducing agent, respectively. First, chlorauric acid, chlorauric acid, silver nitride, copper acetate and palladium nitrate were dissolved in methanol so as to adjust the metal concentration to 4.0% by weight and to adjust the metal weight ratio Au:Ag:Cu:Pd in the metal concentration to 8:1:2:1. Then, the metal solution prepared previously by dissolving the metal salt was gradually added to 9.00 g of 3-aminopropanol to prepare a mixed solution. To the mixed solution, an appropriate amount of sodium borohydride as the reducing agent was added. The reduction reaction was conducted while maintaining the temperature of the mixed solution at 50° C. and stirring the mixed solution using a magnetic stirrer. After the completion of the reductive reaction, the mixed solution was cooled to room temperature. After cooling, the mixed solution was desalted by an ultrafiltration method and the concentration was adjusted by appropriately adding water to obtain a metal colloidal solution having a concentration of 50% by weight, comprising water as a dispersion medium.

Protective agent molecules constituting metal colloidal particles in the resulting metal colloid were subjected to TOF-SIMS analysis. By TOF-SIMS analysis, cluster ions comprising Au and CN were predominantly detected. As is apparent from the results of TOF-SIMS analysis and NMR (C, H) analysis, the protective agent particles are coordination-modified on the surface of metal particles by nitrogen. The content of the accessory component in the metal particles was examined and was found to be 35% by weight. The silver content in the accessory component was examined and was found to be 30% by weight.

Synthesis Examples 30 to 44

In the same manner as in the reaction of Synthesis Example 28 or Synthesis Example 29, except that the metal salt, the protective agent precursor, the reducing agent and the dispersion medium were replaced by the compounds shown in Table 5 and Table 6, various metal colloids were obtained. In the column of the kind of the protective agent precursor in Table 5 and Table 6, compound represented by symbols (A2) to (12) are shown in Table 7. Also the protective agent molecular structure constituting metal colloidal particles in the metal colloids obtained in Synthesis Examples 30 to 44 was confirmed by analyzing using NMR, TOF-SIMS, FT-IR, SAXS, visible ultraviolet spectroscopy, SERS and XAFS in combination.

TABLE 5

| Synthesis Example No. | Metal salt | Protective agent precursor Kind | Protective agent precursor Amount [g] | Coordination-modifying element | Protective agent end structure | Reducing agent | Content of accessory component in metal particles [% by weight] | Content of Ag in accessory component [% by weight] | Dispersion medium | Color tone |
|---|---|---|---|---|---|---|---|---|---|---|
| 28 | Chlorauric acid, silver nitride, copper acetate (weight ratio of metal = 6:2:1) | (A2)<br>(I2) | 9.00<br>12.00 | Nitrogen | Alkoxysilyl group | Dimethylamineborane | 30 | 60 | Water | Yellow gold |

TABLE 5-continued

| Synthesis Example No. | Metal salt | Protective agent precursor Kind | Protective agent precursor Amount [g] | Coordi-nation-modifying element | Protective agent end structure | Reducing agent | Content of accessory component in metal particles [% by weight] | Content of Ag in accessory com-ponent [% by weight] | Dispersion medium | Color tone |
|---|---|---|---|---|---|---|---|---|---|---|
| 29 | Chlorauric acid, silver nitride, copper acetate, palladium nitrate (weight ratio of metal = 8:1:2:1) | (F2) | 9.00 | Nitrogen | Hydroxyalkyl group | Sodium borohydride | 35 | 30 | Water | Pink gold |
| 30 | Chlorauric acid, silver nitride, copper acetate (weight ratio of metal = 6:2:1) | (C2) (I2) | 8.00 12.00 | Nitrogen | Silanol group | Dimethylamineborane | 30 | 60 | Methanol | Yellow gold |
| 31 | Chlorauric acid, silver nitride, copper acetate (weight ratio of metal = 6:2:1) | (E2) | 9.00 | Nitrogen | Hydroxyalkyl group | Dimethylamineborane | 30 | 60 | Water | Yellow gold |
| 32 | Chlorauric acid, silver nitride, copper acetate (weight ratio of metal = 6:2:1) | (H2) | 9.00 | Nitrogen | Hydroxyalkyl group | Diethylmethylamine | 30 | 60 | Cyclohexane | Yellow gold |
| 33 | Chlorauric acid, silver nitride, copper acetate (weight ratio of metal = 8:2:1) | (D2) (I2) | 8.00 12.00 | Nitrogen | Alkoxysilyl group | Dimethylamineborane | 25 | 60 | Water | Green gold |
| 34 | Chlorauric acid, silver nitride, copper acetate (weight ratio of metal = 8:2:1) | (D2) (I2) | 8.00 12.00 | Nitrogen | Alkoxysilyl group | Dimethylamineborane | 25 | 60 | Methanol Water | Green gold |
| 35 | Chlorauric acid, silver nitride, copper acetate (weight ratio of metal = 8:2:1) | (G2) | 8.00 | Nitrogen | Hydroxyalkyl group | Sodium borohydride | 25 | 60 | Water | Green gold |
| 36 | Chlorauric acid, silver nitride, copper acetate (weight ratio of metal = 8:1:2) | (B2) (I2) | 8.00 12.00 | Nitrogen | Silanol group | Sodium borohydride | 25 | 40 | Methanol | Red gold |
| 37 | Chlorauric acid, silver nitride, copper acetate (weight ratio of metal = 8:1:2) | (C2) (I2) | 8.00 12.00 | Nitrogen | Silanol group | Sodium borohydride | 25 | 40 | Water | Red gold |
| 38 | Chlorauric acid, silver nitride, copper acetate (weight ratio of metal = 8:1:2) | (G2) | 7.00 | Nitrogen | Hydroxyalkyl group | Dimethylamineborane | 25 | 40 | Water | Red gold |

TABLE 6

| Synthesis Example No. | Metal salt | Protective agent precursor Kind | Protective agent precursor Amount [g] | Coordi-nation-modifying element | Protective agent end structure | Reducing agent | Content of accessory component in metal particles [% by weight] | Content of Ag in accessory com-ponent [% by weight] | Dispersion medium | Color tone |
|---|---|---|---|---|---|---|---|---|---|---|
| 39 | Chlorauric acid, silver nitride, copper acetate, palladium nitrate (weight ratio of metal = 8:1:2:1) | (C2) (I2) | 8.00 12.00 | Nitrogen | Silanol group | Dimethylamineborane | 35 | 30 | Water | Pink gold |

TABLE 6-continued

| Synthesis Example No. | Metal salt | Protective agent precursor Kind | Protective agent precursor Amount [g] | Coordination-modifying element | Protective agent end structure | Reducing agent | Content of accessory component in metal particles [% by weight] | Content of Ag in accessory component [% by weight] | Dispersion medium | Color tone |
|---|---|---|---|---|---|---|---|---|---|---|
| 40 | Chlorauric acid, silver nitride, copper acetate, palladium nitrate (weight ratio of metal = 8:1:2:1) | (C2)<br>(I2) | 8.00<br>12.00 | Nitrogen | Silanol group | Diethylmethylamine | 35 | 30 | Ethylene glycol | Pink gold |
| 41 | Chlorauric acid, silver nitride, copper acetate, Palladium nitrate (weight ratio of metal = 8:1:2:1) | (E2) | 6.00 | Nitrogen | Hydroxyalkyl group | Sodium borohydride | 35 | 30 | Water | Pink gold |
| 42 | Chlorauric acid, palladium nitrate (weight ratio of metal = 3:1) | (B2)<br>(I2) | 8.00<br>12.00 | Nitrogen | Silanol group | Diethylmethylamine | 25 | — | Water | White gold |
| 43 | Chlorauric acid, palladium nitrate (weight ratio of metal = 3:1) | (G2) | 8.00 | Nitrogen | Hydroxyalkyl group | Trimethylamineborane | 25 | — | Ethanol | White gold |
| 44 | Chlorauric acid, palladium nitrate (weight ratio of metal = 3:1) | (H2) | 8.00 | Nitrogen | Hydroxyalkyl group | Dimethylamineborane | 25 | — | Cyclohexane | White gold |

TABLE 7

| Symbol | Name |
|---|---|
| (A2) | γ-aminopropyltriethoxysilane |
| (B2) | N-β(aminoethyl)γ-aminopropyltrimethoxysilane |
| (C2) | N-β(aminoethyl)γ-aminopropylmethyldimethoxysilane |
| (D2) | N-β(aminoethyl)γ-aminopropyltriethoxysilane |
| (E2) | 2-aminoethanol |
| (F2) | 3-aminopropanol |
| (G2) | 1-amino-2-propanol |
| (H2) | 2-amino-1-butanol |
| (I2) | Acetylacetone |

Example 45

The metal colloids having a concentration of 50% by weight obtained in Synthesis Examples 28 to 44 were prepared and each of the metal colloids having a concentration of 50% by weight was diluted to prepare dilute metal colloidal solutions each having a concentration of 5% by weight, 10% by weight, 15% by weight, 20% by weight, 25% by weight, 30% by weight and 40% by weight, respectively. Using each of dilute metal colloidal solutions each having a concentration of 5 to 50% by weight, predetermined characters were written on a Japanese paper using a writing brush of India ink, and then air-dried. In case of using a dilute solution of the metal colloid having a concentration of 30% by weight or less obtained in Synthesis Example 28, the written characters showed a yellow gold color tone and metal gloss and were excellent in brightness and design properties, and the characters were not peeled off even when the surface of the characters are rubbed with a cloth. Also in case of using each of dilute solutions of the metal colloids having a concentration of 30% by weight or less obtained in Synthesis Example 33, Synthesis Example 37, Synthesis Example 39 and Synthesis Example 42, characters were written and then air-dried on a Japanese paper. The written characters respectively showed a green gold color tone (Synthesis Example 33), a red gold color tone (Synthesis Example 37), a pink gold color tone (Synthesis Example 39) and a white gold color tone (Synthesis Example 42) and metal gloss and were excellent in brightness and design properties, and the characters were not peeled off even when the surface of the characters are rubbed with a cloth, similarly.

In case of using a dilute metal colloidal solution having a concentration of 20% by weight or less, the characters written on the Japanese paper showed metal gloss, but showed color tone which is seemed to be different from the color tone peculiar to metal. When characters are written on a Japanese paper subjected to a surface treatment for preventing penetration of the metal colloid, or a base material into which the metal colloid does not penetrate, the resulting characters written using the metal colloid having a concentration of 20% by weight or less showed the same metal gloss and color tone as those obtained in case of using the metal colloid having a concentration of more than 20% by weight. After storing the dilute metal colloidal solution at room temperature for 3 weeks, characters were written again on the Japanese paper using the stored metal colloid. Similar to the case before the storage, the written characters showed color tone and metal specular gloss peculiar to metal and were excellent in brightness and design properties.

Comparative Example 3

Chlorauric acid was prepared as a metal salt used as a main component of metal particles, silver nitride and copper acetate were prepared as a metal salt used as an accessory component, γ-mercaptopropyltrimethoxysilane and acetylacetone were prepared as a protective agent precursor, and dimethylamineborane was prepared as a reducing agent, respectively. First, chlorauric acid, silver nitride and copper acetate were dissolved in methanol so as to adjust the metal concentration to 4.0% by weight and to adjust the metal weight ratio Au:Ag:Cu in the metal concentration to 6:2:1. Then, 3.00 g of γ-mercaptotrimethoxysilane was mixed with 12.00 g of acetylacetone and an appropriate amount of dimethylamineborane was added to the mixed solution. Then, the metal solution prepared previously by dissolving the metal salt was gradually added to prepare a mixed solution. This mixed solution was prepared by maintaining at 60° C. while stirring the mixed solution using a magnetic stirrer, and the reductive reaction was conducted until metal colloidal particles are produced and show a red color. After the completion of the reductive reaction, the mixed solution was cooled to room temperature. After cooling, the mixed solution was desalted by an ultrafiltration method to obtain a metal colloid containing water as a dispersion medium. The concentration of this metal colloid was adjusted by adding an appropriate amount of water to obtain a metal colloid having a concentration of 50% by weight, comprising water as a dispersion medium.

Protective agent molecules constituting metal colloidal particles in the resulting metal colloid were subjected to TOF-SIMS analysis. As is apparent from the results of TOF-SIMS analysis and NMR analysis, the protective agent molecules are coordination-modified on the surface of the metal particles by sulfur and oxygen.

Comparative Evaluation

Using the metal colloid of Comparative Example 3, desired characters were written on a Japanese paper using a writing brush for India ink and then air-dried. The written characters showed metal color with a yellow gold color tone and metal gloss. With respect to the characters obtained by using the metal colloid of Comparative Example 3, and the characters obtained by using the metal colloids of Synthesis Example 28, Synthesis Example 33, Synthesis Example 37, Synthesis Example 39 and Synthesis Example 42 in Example 45, color tone, ease of peeling and brightness were visually evaluated. The ease of peeling was confirmed by the method of rubbing the surface of characters with a cloth conducted in Example 45. The results are shown in Table 8.

TABLE 8

| | | Color tone | Ease of peeling | Brightness |
|---|---|---|---|---|
| Example 45 | Synthesis Example 28 | Yellow gold | not peeled | Excellent |
| | Synthesis Example 33 | Green gold | not peeled | Excellent |
| | Synthesis Example 37 | Red gold | not peeled | Excellent |
| | Synthesis Example 39 | Pink gold | not peeled | Excellent |
| | Synthesis Example 42 | White gold | not peeled | Excellent |
| Comparative Example 3 | | Yellow gold | not peeled | Slightly poor |

As is apparent from the results shown in Table 8, the written characters obtained using the metal colloids of Example 45 and Comparative Example 3 showed various gold-based color tones. Regarding the ease of peeling, all written characters obtained by using any metal colloids were not peeled off. However, the written characters obtained by using the metal colloid of Example 45 was excellent in brightness as compared with the written characters obtained by using the metal colloid of Comparative Example 3.

Example 46

First, a glass cup, a ceramic ware, a coffee cup made of porcelain and a plastic plate made of polycarbonate were prepared, respectively. Using the dilute metal colloidal solution prepared in Example 45, desired patterns were drawn on the glass cup and the ceramic ware. Also, desired characteristics were written on the side of the coffee cup made of porcelain and the surface of the plastic plate made of polycarbonate. The written characters showed metal color with various gold-based color tones such as yellow gold, green gold, red gold, pink gold and white gold, and metal gloss and were excellent in brightness and design properties, similar to Example 45. The characters and patterns were not peeled off even when the surface of the characters and patterns are rubbed with a cloth.

Example 47

The dilute metal colloidal solution prepared in Example 45 was coated on the surface of an artificial hair, an artificial eyelash, a plastic model, an amulet case, a skippet, a memorial card, an invitation card, a greeting card, a doll, a Buddhist image, a mortuary tablet, a picture frame, clothes and a woven fabric, respectively. Specifically, the metal colloid was coated on the artificial hair by a method of spraying using an airbrush, while the metal colloid was coated on the entire surface of the artificial eyelash, the plastic model, the doll and the Buddhist image using a writing brush. Also writing desired characters were written on the mortuary tablet using a wiring brush and the metal colloid was coated only on the frame portion of the picture frame using a writing brush, and desired characters or patterns were drawn on the memorial card, the invitation card, the greeting card, the amulet case, the skippet, clothes and the woven fabric using a writing brush. After coating, the dispersion medium in the dilute metal colloidal solution was sufficiently removed by drying with an air of a dryer to form a metal colloid-containing coat. Each metal colloid-containing coat showed metal color with various gold-based color tones and metal gloss and was excellent in brightness and design properties, similar to the characters written in Example 45.

Example 48

First, the dilute metal colloidal solution prepared in Example 45 was coated on the following jewelries. A dilute metal colloidal solution was coated on a ring, a ring made of a silver clay, a pierced earring, an earring, a bracelet, a necklace, a key holder and an ornamental hairpin using a writing brush, and the colloid was coated on a watch, a hairpin, a broach and a tiepin by a method of spraying using an airbrush. After coating, the dispersion medium in the dilute metal colloidal solution was sufficiently removed by drying with an air of a dryer to form a metal colloid-containing coat. Each metal colloid-containing coat formed on the surface of jewelries showed various gold-based color tones and metal gloss and was excellent in brightness and design properties, similar to the characters written in Example 45.

Example 49

The dilute metal colloidal solution prepared in Example 45, a natural nail and an artificial nail were prepared, respectively. By a method of coating the metal colloid using a writing brush for manicure shown in FIG. 12, the metal colloid was coated on the surface of the natural nail and the artificial nail. After coating, the dispersion medium in the dilute metal colloidal solution was sufficiently removed by drying with an air of a dryer to form a metal colloid-containing coat. Each metal colloid-containing coat formed on the surface of the natural nail and the artificial nail showed various gold-based color tones and metal gloss and was excellent in brightness and design properties, similar to the characters written in Example 45.

Example 50

Using a method of spraying a metal colloid using an airbrush for manicure shown in FIG. 14, the dilute metal colloidal solution prepared in Example 45 was sprayed over the surface of a natural nail and the surface of an artificial nail. After spraying, the dispersion medium in the dilute metal colloidal solution was sufficiently removed by drying with an air of a dryer to form a metal colloid-containing coat. Similar to the characters written in Example 45, each metal colloid-containing coat formed on the surface of the natural nail and the artificial nail showed various gold-based color tones and metal gloss and was excellent in brightness and design properties. The resulting coat has matted gloss and is excellent in smoothness, unlike the coat of Example 49 formed by coating using a writing brush for manicure.

Example 51

First, in the same manner as in Example 49, the dilute metal colloidal solution prepared in Example 45 was coated on the surface of a natural nail and the surface of an artificial nail using a writing brush for manicure. After coating, the dispersion medium in the dilute metal colloidal solution was sufficiently removed by drying with an air of a dryer to form a metal colloid-containing coat. Then, a top coating agent was coated on the metal colloid-containing coat thus formed by a wet-on-wet coating method and this top coating prevented the metal colloid-containing coat from being peeled off with ease. The metal colloid-containing coat formed on the surface of the artificial nail showed metal color with various gold-based color tones and metal gloss and was excellent in brightness and design properties, similar to the case of the coat obtained in Example 49.

Example 52

First, an under coat layer was formed on the surface of an artificial nail. In the same manner as in Example 49, the dilute metal colloidal solution prepared in Example 45 was coated on the surface of the under coat layer using a writing brush for manicure. After coating, the dispersion medium in the dilute metal colloidal solution was sufficiently removed by drying with an air of a dryer to form a metal colloid-containing coat. The metal colloid-containing coat formed on the surface of the artificial nail showed metal color with various gold-based color tones and metal gloss and was excellent in brightness and design properties, similar to the case of the coats obtained in Example 49 and Example 51.

Example 53

First, an under coat layer was formed on the surface of an artificial nail. In the same manner as in Example 49, the dilute metal colloidal solution prepared in Example 45 was coated on the surface of the under coat layer using a writing brush for manicure. After coating, the dispersion medium in the dilute metal colloidal solution was sufficiently removed by drying with an air of a dryer to form a metal colloid-containing coat. Then, a top coating agent was coated on the metal colloid-containing coat thus formed by a wet-on-wet coating method and this top coating prevented the metal colloid-containing coat from being peeled off with ease. The metal colloid-containing coat formed on the surface of the artificial nail showed metal color with various gold-based color tones and metal gloss and was excellent in brightness and design properties, similar to the case of the coats obtained in Example 49, Example 51 and Example 52.

Example 54

In the same manner as in Example 53, except that the dilute metal colloidal solution was coated only at the tip portion of the nail using an airbrush, a metal colloid-containing coat was formed on the surface of an artificial nail. In the same manner as in Example 53, except that desired patterns were drawn on the surface of the nail using a writing brush for manicure in case of coating the dilute metal colloidal solution, a metal colloid-containing coat was formed on the surface of an artificial nail. The artificial nail coated with the metal colloid only at the tip portion using an airbrush and the artificial nail wherein desired patterns are drawn on the surface of the nail using a writing brush for manicure showed metal color with various gold-based color tones and metal gloss and was excellent in brightness and design properties, similar to Examples 49 to 53.

Example 55

First, an under coating agent was coated on the surface of an artificial nail and then dried to form an under coat layer. In the same manner as in Example 49, the dilute metal colloidal solution prepared in Example 45 was coated on the surface of the under coat layer using a writing brush for manicure. The dispersion medium in the dilute metal colloidal solution was removed by drying with an air of a dryer to form a metal colloid-containing coat. Then, a top coating agent was coated on the metal colloid-containing coat thus formed and, before completely drying the top coating agent, a lame agent as a material was scattered at desired points and diamond natural stones and pink sapphire natural stones were set thereon, and then these materials were fixed by pressing and immobilized by drying the top coating agent with an air of a dryer. Immobilization of these materials was enhanced by further coating the top coating agent. Brightness and design properties were improved by using the metal colloid-containing coat formed on the artificial nail in combination of the lame agent and natural gems of diamond and pink sapphire.

Example 56

The dilute metal colloidal solution prepared in Example 45 was coated only at the tip portion of an artificial nail using a writing brush for manicure. After coating, the dispersion medium in the dilute metal colloidal solution was removed by drying with an air of a dryer to form a metal colloid-containing coat. Then, a top coating agent was coated on the metal colloid-containing coat thus formed and, before completely drying the top coating agent, natural stones of ruby, diamond and sapphire as materials were arranged at desired points, and then these materials were fixed by pressing and immobilized by drying the top coating agent with an air of a dryer. Immobilization of these materials was enhanced by further coating the top coating agent. Brightness and design properties were improved by using the metal colloid-containing coat formed only at the tip portion of the artificial nail in combination of natural stones of ruby, diamond and sapphire.

Example 57

Desired patterns were drawn on the surface of a nail with the dilute metal colloidal solution prepared in Example 45 using a writing brush for manicure. After drawing, the dispersion medium in the dilute metal colloidal solution was removed by drying with an air of a dryer to form a metal colloid-containing coat on the surface of the nail. Then, a top coating agent was coated on the entire surface of a nail and, before completely drying the top coating agent, a gold foil powder and diamond and pink sapphire natural stones as materials were set at the desired points, and then these materials were fixed by pressing and immobilized by drying the top coating agent with an air of a dryer. Immobilization of these materials was enhanced by further coating the top coating agent. Brightness and design properties were improved by using the metal colloid-containing coat formed on the artificial nail in combination with the gold foil powder and natural gems of diamond and pink sapphire.

Example 58

First, as shown in FIG. 19, a coating solution of an acrylic resin was coated on one surface of a base material 2 made of a releasable synthetic paper to form a surface protective layer 4. Then, the dilute gold colloidal solution prepared in Example 45 was coated on the surface protective layer 4 to form a metal colloid-containing coat layer 5. Furthermore, a coating solution of a hot melt type resin was coated on the metal colloid-containing coat layer 5 to form an adhesive layer 6, thus obtaining a transfer sheet 1 wherein a transfer layer 3 comprising the surface protective layer 4, the metal colloid-containing coat layer 5 and an adhesive layer 6 is formed on the base material 2.

Example 59

In the same manner as in Example 58, except that, in case of forming a metal colloid-containing coat layer 5 in the production of a transfer sheet, characters or patterns were drawn by an ink jet printer to form the metal colloid-containing coat layer 5, a transfer sheet was produced.

Example 60

Each of the transfer sheets of Example 58 and Example 59 was thermally transferred under pressure to a paper, clothes, a leather and a glass to form a metal colloid-containing coat on the surface. Similar to characters written in Example 45, the metal colloid-containing coat showed metal color with various gold-based color tones and metal gloss and was excellent in brightness and design properties. The metal colloid-containing coat as the transfer film was not peeled off even when rubbed with fingers. The method for thermal transfer under pressure can be conducted by a conventionally known method.

Example 61

As shown in FIG. 20 A, there was prepared a cartridge 10 for pen which is composed of a tubular body 11 having a closed lower portion, a lid portion 13 which is joined with the upper portion of the tubular body 11 and is provided with a spherical continuous hole at center, and a spherical plug 14 having a diameter, which is smaller than the shape of the continuous hole and is enough to prevent from falling off from the continuous hole, inserted into the continuous hole of the lid portion 13, the tubular body 11 being filled with the dilute metal colloidal solution 12 prepared in Example 45.

As shown in FIG. 20 B, a pen 20 comprising the cartridge 10 for pen incorporated thereinto was prepared. This pen 20 is composed of a cylindrical upper shaft barrel 21, a cylindrical lower shaft barrel 22, the upper end of which can be connected to the lower end of the upper shaft barrel 21, and a tip 26 which is connected to the other end of the lower shaft barrel 22. The inner wall of the lower shaft barrel 22 is provided with a connection portion 23 which inserts the cartridge 10 for pen and contacts with the lid portion 13, thereby to push up the spherical plug 14 into the cartridge 10 for pen. In the connection portion 23, there is provided a core portion 24 capable of being impregnated with the dilute metal colloidal solution discharging from the cartridge 10 due to gravity while protruding the other end of the lower shaft barrel 22 when the cartridge 10 for pen is connected to the connection portion 23 and the spherical plug 14 is pushed up by the connection portion 23. The tip 26 connected to the other end of the lower shaft barrel 22 serves to eject the dilute metal colloidal solution, with which the core portion 24 is impregnated, from the tip.

The cartridge 10 for pen was connected to the pen 20 by contacting the lid portion 13 of the cartridge with the connection portion 23 and pushing the connection portion 23 and the plug 14 into the cartridge 10 for pen. In that case, the dilute metal colloidal solution 12 filled into the cartridge 10 is discharged from the gap between the lid portion 13 and the spherical plug 14 and thus the core portion 24 is impregnated with the dilute metal colloidal solution, which is supplied to the tip 26 through the core portion 24. The pen comprising the cartridge 10 for pen connected thereto is easy to draw and was capable of drawing smoothly. This pen is very advantageous to write desired characters and to draw predetermined patterns on the desired base material, and the characters and patterns drawn by the pen showed metal color with various gold-based color tones and metal gloss and were excellent in brightness, similar to the characters written in Examples 45.

Example 62

As shown in FIG. 21, there was prepared a disposable ampul 30 which is composed of a tubular body 31 having a closed lower portion, a cut portion 33 joined with the upper portion of the tubular body 31, and a lid portion 32, the cut portion 33 being provided with a smaller width than that of the tubular body 31 and the lid portion 32 so that it can be cut by a hand operation, the disposable ampul having a structure that the dilute metal colloidal solution 34 prepared in Example 45 is sealed by thermal contact bonding of the cut portion 33 and the lid portion 32 after filling the tubular body 31 with the dilute metal colloidal solution 34.

In the disposable ampul 30 thus obtained, the lid portion 32 can be easily cut from the cut portion 33 through the lever rule by laterally rotating the lid portion 32 and the cut surface is communicated with the inside of the tubular body 31. The metal colloid filled in the tubular body 31 can be used after taking out from the communicated portion.

Example 63

A stamp pad and a seal impression pad were produced by sufficiently impregnating with the dilute metal colloidal solution prepared in Example 45 having a concentration of 30% by weight. Using the stamp pad and the seal impression pad, patterns were formed on a wallet or a key holder by forming patterns of a metal colloid-containing coat on a leather, or a memorial card was produced by forming patterns of a metal colloid-containing coat on a paper. The patterns made by using the stamp pad or seal impression pad containing the dilute metal colloidal solution showed metal color with various gold-based color tones and metal gloss and were excellent in brightness, similar to the characters written in Examples 45.

Example 64

Using the dilute metal colloidal solution prepared in Example 45, a spiral scoring test was conducted by an ink jet printer apparatus. As the base material, a paper, a leather and a lumber were used. Using the paper, a business card, a greeting card, a memorial card and an invitation card were produced. In case of using the leather, a leather wallet was drawn. In case of using the lumber, desired characters were written on a mortuary tablet. The patterns drawn by the ink jet printer apparatus using the dilute metal colloidal solution showed metal color with various gold-based color tones and metal gloss and were excellent in brightness and design properties, similar to the characters written in Examples 45.

Example 65

Using the dilute metal colloidal solution prepared in Example 45 as an ink, characters and patterns were drawn on a colored paper by a writing brush. The characters and patterns showed metal color with various gold-based color tones and metal gloss and were excellent in brightness and design properties, similar to the characters written in Examples 45. In case of drawing characters or patterns, a pen filled with the dilute metal colloidal solution described in Example 61 as an ink may be used.

Example 66

Using the dilute metal colloidal solution prepared in Example 45 as an ink, a hand print and a foot print were formed on a colored paper. The hand print and the foot print showed metal color with various gold-based color tones and metal gloss and were excellent in brightness and design properties, similar to the characters written in Examples 45.

Example 67

First, a paper wherein patterns are written on the surface by a commercially available black ink using a seal impression and a stamp, a colored paper wherein characters and patterns are drawn on the surface using a black pen, and a colored paper wherein a hand print and a foot print are formed using a black ink were prepared. Using an image scanner, the surface of the paper and that of the colored paper were scanned and the resulting image data were inputted into a computer. By an ink jet printer using the dilute metal colloidal solution prepared in Example 45 as an ink, image data were printed on the paper and the colored paper based on the inputted image data. Characters and patterns printed on the paper and the colored paper using the dilute metal colloidal solution of the present invention showed the same shape as that of black colored characters and patterns drawn and also showed metal color with various gold-based color tones and metal gloss and were excellent in brightness and design properties, similar to the characters written in Examples 45.

In Example 67, using the image scanner, the surface of the paper and that of the colored paper were scanned and the resulting image data were inputted into a computer and then printed using the ink jet printer. Using the image scanner, not only base papers such as paper and colored paper, but also a photograph of these base papers, and a print and a publication in which these patterns and characters are described may be scanned and the resulting image data may be inputted into a computer and directly printed using an ink jet printer.

Synthesis Example 45

Chlorauric acid was prepared as a metal salt used as a main component of metal particles, γ-aminopropyltriethoxysilane and acetylacetone were prepared as a protective agent precursor, and dimethylamineborane was prepared as a reducing agent, respectively. First, a methanol solution prepared by dissolving chlorauric acid so as to adjust the gold concentration to 4.0% by weight was gradually added to 8.00 g of γ-aminopropyltriethoxysilane and 12.00 g of acetylacetone to prepare a mixed solution. To the mixed solution, an appropriate amount of dimethylamineborane as the reducing agent was added. This mixed solution was prepared by maintaining at 60° C. while stirring the mixed solution using a magnetic stirrer, and the reductive reaction was conducted until metal colloidal particles are produced and show a red color. After the completion of the reductive reaction, the mixed solution was cooled to room temperature. After cooling, the mixed solution was desalted by an ultrafiltration method to obtain a metal colloid containing water as a dispersion medium. The concentration of this metal colloid was adjusted by adding an appropriate amount of water to obtain a metal colloid having a concentration of 50% by weight wherein Au colloidal particles are dispersed in water.

Protective agent molecules constituting Au colloidal particles in the resulting metal colloid were subjected to TOF-SIMS analysis. By TOF-SIMS analysis, cluster ions comprising Au and CN were predominantly detected. As is apparent from the results of TOF-SIMS analysis and NMR (C, H) analysis, the protective agent particles are coordination-modified on the surface of Au particles by nitrogen.

Synthesis Example 46

Chlorauric acid was prepared as a metal salt used as a main component of metal particles, 3-aminoethanol and acetylacetone were prepared as a protective agent precursor, and dimethylamineborane was prepared as a reducing agent, respectively. First, a methanol solution prepared by dissolving chlorauric acid so as to adjust the gold concentration to 4.0% by weight was gradually added to 9.00 g of 3-aminoethanol and 12.00 g of acetylacetone to prepare a mixed solution. To the mixed solution, an appropriate amount of dimethylamineborane as the reducing agent was added. This mixed solution was prepared by maintaining at 60° C. while stirring the mixed solution using a magnetic stirrer, and the reductive reaction was conducted until metal colloidal particles are produced and show a red color. After the completion of the reductive reaction, the mixed solution was cooled to room temperature. After cooling, the mixed solution was desalted by an ultrafiltration method to obtain a metal colloid containing water as a dispersion medium. The concentration of this metal colloid was adjusted by adding an appropriate amount of water to obtain a metal colloid having a concentration of 50% by weight wherein Au colloidal particles are dispersed in water.

Protective agent molecules constituting Au colloidal particles in the resulting metal colloid were subjected to TOF-SIMS analysis. By TOF-SIMS analysis, cluster ions comprising Au and CN were predominantly detected. As is apparent from the results of TOF-SIMS analysis and NMR (C, H) analysis, the protective agent particles are coordination-modified on the surface of Au particles by nitrogen.

Synthesis Examples 47 to 71

In the same manner as in Synthesis Example 45, except that the metal salt, the protective agent precursor, the reducing agent and the dispersion medium were replaced by the com pounds shown in Table 9 and Table 10, various metal colloids were obtained.

Synthesis Examples 72 to 86

In the same manner as in Synthesis Example 45, except that the metal salt, the protective agent precursor, the reducing agent and the dispersion medium were replaced by the compounds shown in Table 10 and Table 11 and the temperature at which the mixed solution is prepared was changed to 35° C., various metal colloids were obtained. In the column of the kind of the protective agent precursor in Table 9 to Table 11, compound represented by symbols (A3) to (N3) are shown in Table 12.

TABLE 9

| Synthesis Example No. | Metal salt | Protective agent precursor Kind | Protective agent precursor Amount [g] | Reducing agent | Dispersion medium | Coordination-modifying element | Protective agent end structure |
|---|---|---|---|---|---|---|---|
| 45 | Chloraruic acid | (A3)<br>Acetylacetone | 8.00<br>12.00 | Dimethylamineborane | Water | Nitrogen | Alkoxysilyl group |
| 46 | Chloraruic acid | (F3)<br>Acetylacetone | 9.00<br>12.00 | Dimethylamineborane | Water | Nitrogen | Hydroxyalkyl group |
| 47 | Chloraruic acid | (A3)<br>Acetylacetone | 8.00<br>12.00 | Sodium borohydride | Water | Nitrogen | Alkoxysilyl group |
| 48 | Chloraruic acid | (A3)<br>Acetylacetone | 8.00<br>12.00 | Sodium borohydride | Methanol | Nitrogen | Alkoxysilyl group |
| 49 | Chloraruic acid | (B3)<br>Acetylacetone | 8.00<br>12.00 | Dimethylamineborane | Water | Nitrogen | Silanol group |
| 50 | Chloraruic acid | (C3)<br>Acetylacetone | 8.00<br>12.00 | Dimethylamineborane | Methanol | Nitrogen | Silanol group |
| 51 | Chloraruic acid | (C3)<br>Acetylacetone | 8.00<br>12.00 | Dimethylamineborane | Water | Nitrogen | Silanol group |
| 52 | Chloraruic acid | (C3)<br>Acetylacetone | 8.00<br>12.00 | Dimethylamineborane | Ethylene glycol | Nitrogen | Silanol group |
| 53 | Chloraruic acid | (D3)<br>Acetylacetone | 8.00<br>12.00 | Dimethylamineborane | Methanol | Nitrogen | Alkoxysilyl group |
| 54 | Chloraruic acid | (D3)<br>Acetylacetone | 8.00<br>12.00 | Dimethylamineborane | Water | Nitrogen | Alkoxysilyl group |
| 55 | Chloraruic acid | (E3) | 9.00 | Dimethylamineborane | Water | Nitrogen | Hydroxyalkyl group |
| 56 | Chloraruic acid | (E3) | 9.00 | Dimethylamineborane | Water, methanol | Nitrogen | Hydroxyalkyl group |
| 57 | Chloraruic acid | (E3) | 9.00 | Sodium borohydride | Water | Nitrogen | Hydroxyalkyl group |
| 58 | Chloraruic acid | (E3) | 8.00 | Sodium borohydride | Water, methanol | Nitrogen | Hydroxyalkyl group |
| 59 | Chloraruic acid | (F3) | 8.00 | Sodium borohydride | Water | Nitrogen | Hydroxyalkyl group |
| 60 | Chloraruic acid | (G3) | 8.00 | Sodium borohydride | Water | Nitrogen | Hydroxyalkyl group |
| 61 | Chloraruic acid | (G3) | 8.00 | Sodium borohydride | Water, ethanol | Nitrogen | Hydroxyalkyl group |
| 62 | Chloraruic acid | (G3) | 8.00 | Dimethylamineborane | Water | Nitrogen | Hydroxyalkyl group |
| 63 | Chloraruic acid | (G3) | 8.00 | Dimethylamineborane | Water, ethanol | Nitrogen | Hydroxyalkyl group |
| 64 | Silver nitride | (B3)<br>Acetylacetone | 7.00<br>12.00 | Sodium borohydride | Methanol | Nitrogen | Alkoxysilyl group |

TABLE 10

| Synthesis Example No. | Metal salt | Protective agent precursor Kind | Protective agent precursor Amount [g] | Reducing agent | Dispersion medium | Coordination-modifying element | Protective agent end structure |
|---|---|---|---|---|---|---|---|
| 65 | Silver nitride | (C3)<br>Acetylacetone | 7.00<br>12.00 | Dimethylamineborane | Water | Nitrogen | Silanol group |
| 66 | Silver nitride | (H3) | 7.00 | Trimethylamineborane | Cyclohexane | Nitrogen | Hydroxyalkyl group |

TABLE 10-continued

| Synthesis Example No. | Metal salt | Protective agent precursor Kind | Amount [g] | Reducing agent | Dispersion medium | Coordination-modifying element | Protective agent end structure |
|---|---|---|---|---|---|---|---|
| 67 | Chlorauric acid, silver nitride (weight ratio = 2:1) | (C3) Acetylacetone | 8.00 12.00 | Dimethylamineborane | Methanol | Nitrogen | Silanol group |
| 68 | Ruthenium trichloride | (D3) Acetylacetone | 6.00 12.00 | Sodium borohydride | Water | Nitrogen | Alkoxysilyl group |
| 69 | Chloroplatinic acid | (C3) Acetylacetone | 8.00 12.00 | Dimethylamineborane | Water | Nitrogen | Silanol group |
| 70 | Chloroplatinic acid | (G3) | 8.00 | Dimethylamineborane | Water | Nitrogen | Hydroxyalkyl group |
| 71 | Copper acetate | (H3) | 8.00 | Dimethylamineborane | Cyclohexane | Nitrogen | Hydroxyalkyl group |
| 72 | Chlorauric acid | (C3) | 9.00 | 2-aminoethanol | Water, ethanol (weight ratio = 4:1) | Nitrogen | Hydroxyalkyl group |
| 73 | Chlorauric acid | (D3) | 9.00 | 1-amino-2-propanol | Water | Nitrogen | Hydroxyalkyl group |
| 74 | Chlorauric acid | (C3) | 9.00 | Dimethylamineborane | Water, ethanol (weight ratio = 4:1) | Nitrogen | Hydroxyalkyl group |
| 75 | Chlorauric acid | (D3) | 9.00 | Dimethylamineborane | | Nitrogen | Hydroxyalkyl group |
| 76 | Chlorauric acid | (C3) | 9.00 | Hydrogen peroxide | Water, N,N-dimethylformamide, ethanol (weight ratio = 3:1:1) | Nitrogen | Hydroxyalkyl group |
| 77 | Chlorauric acid | (C3) | 9.00 | Hydrazine | Water, N-methyl pyrrolidinone, ethylene glycol (weight ratio = 5:1:1) | Nitrogen | Hydroxyalkyl group |
| 78 | Chlorauric acid | (C3) | 9.00 | Sodium hypophosphite | Water, ethanol, diethylene glycol (weight ratio = 4:1:1) | Nitrogen | Hydroxyalkyl group |
| 79 | Chlorauric acid | (D3) | 9.00 | Hydrazine | Water, glycerin, ethanol (weight ratio = 4:1:1) | Nitrogen | Hydroxyalkyl group |

TABLE 11

| Synthesis Example No. | Metal salt | Protective agent precursor Kind | Amount [g] | Reducing agent | Dispersion medium | Coordination-modifying element | Protective agent end structure |
|---|---|---|---|---|---|---|---|
| 80 | Chlorauric acid | (I3) | 9.00 | Dimethylamineborane | Water, N,N-dimethylformamide, ethanol (weight ratio = 3:1:1) | Nitrogen | Hydroxyalkyl group |
| 81 | Chlorauric acid | (J3) | 9.00 | Dimethylamineborane | Water, N-methylpyrrolidinone, | Nitrogen | Hydroxyalkyl group |
| 82 | Chlorauric acid | (K3) | 9.00 | Dimethylamineborane | N,N-dimethylformamide, | Nitrogen | Hydroxyalkyl group |
| 83 | Chlorauric acid | (L3) | 9.00 | Dimethylamineborane | ethylene glycol (weight ratio = 2:1:1:1) | Nitrogen | Hydroxyalkyl group |
| 84 | Chlorauric acid | (M3) | 9.00 | Dimethylamineborane | | Nitrogen | Hydroxyalkyl group |
| 85 | Chlorauric acid | (N3) | 9.00 | Dimethylamineborane | | Nitrogen | Hydroxyalkyl group |
| 86 | Silver nitride | (D3) | 10.00 | 1-amino-2-propanol | Water | Nitrogen | Hydroxyalkyl group |

TABLE 12

| Symbol | Name |
|---|---|
| (A3) | γ-aminopropyltriethoxysilane |
| (B3) | N-β(aminoethyl)γ-aminopropyltrimethoxysilane |
| (C3) | N-β(aminoethyl)γ-aminopropylmethyldimethoxysilane |
| (D3) | N-β(aminoethyl)γ-aminopropyltriethoxysilane |

TABLE 12-continued

| Symbol | Name |
|---|---|
| (E3) | 2-aminoethanol |
| (F3) | 3-aminoethanol |
| (G3) | 1-amino-2-propanol |
| (H3) | 2,2'-imidionoethanol |

TABLE 12-continued

| Symbol | Name |
|---|---|
| (I3) | 2-amino-2-methyl-1-propanol |
| (J3) | L-(−)-2-amino-3-phenyl-1-propanol |
| (K3) | 3-amino-3-phenyl-1-propanol |
| (L3) | (R)-(−)-2-amino-1-propanol |
| (M3) | (s)-(+)-2-amino-1-propanol |
| (N3) | 3-amino-1-propanol |

Example 68

The metal colloids having a concentration of 50% by weight obtained in Synthesis Examples 45 to 86 were prepared and each of the metal colloids having a concentration of 50% by weight was diluted to prepare a metal colloids each having a concentration of 5% by weight, 10% by weight, 15% by weight, 20% by weight, 25% by weight, 30% by weight and 40% by weight, respectively. As the base material, an artificial hair, an artificial eyelash, a plastic model, an amulet case, a skippet, a memorial card, an invitation card, a greeting card, a doll, a Buddhist image, a mortuary tablet, a picture frame, clothes and a woven fabric were prepared, respectively. Specifically, the metal colloid thus prepared was coated on the artificial hair by a method of spraying using an airbrush, while the metal colloid was coated on the entire surface of the artificial eyelash, the plastic model, the doll and the Buddhist image using a writing brush. Also writing desired characters were written on the mortuary tablet using a wiring brush and the metal colloid was coated only on the frame portion of the picture frame using a writing brush, and desired characters or patterns were drawn on the memorial card, the invitation card, the greeting card, the amulet case, the skippet, clothes and the woven fabric using a writing brush. After coating on the base material, the dispersion medium in the dilute metal colloidal solution was sufficiently removed by drying with an air of a dryer to form a metal colloid-containing coat. A photograph of an invitation card wherein characters are written on the surface using a metal colloid is shown in FIG. 26 A and a photograph of a doll, the surface of which is coated with a metal colloid is shown in FIG. 26 B, respectively.

Figure 26B:
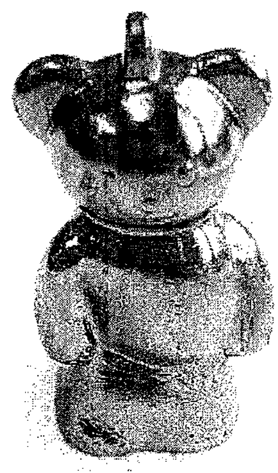
FIG. 26 A is a photograph showing a memorial card wherein characters are written on the surface using a metal colloid.

As is apparent from FIG. 26 A and FIG. 26 B, the resulting metal colloid-containing coat formed article showed metal gloss and color tone peculiar to metal and was excellent in brightness and design properties.

Example 69

As the base material, a ring, a ring made of a silver clay pierced earring, an earring, a bracelet, a necklace, a key holder, an ornamental hairpin, a watch, a hairpin, a broach and a tiepin were prepared, respectively. Then, using the metal colloidal prepared in Example 68, a gold colloid was coated on the ring, the ring made of a silver clay, the pierced earring, the earring, the bracelet, the necklace, the key holder and the ornamental hairpin using a writing brush. Using the metal colloidal prepared in Example 68, a gold colloid was coated on the watch, the hairpin, the broach and the tiepin by a method of spraying using an airbrush. After coating on the base material, the dispersion medium in the dilute metal colloidal solution was sufficiently removed by drying with an air of a dryer to form a metal colloid-containing coat. A photograph of a ring wherein the surface other than the display portion is coated with a metal colloid is shown in FIG. 27 A, a photograph of a pierced earring, the surface of which is coated with a metal colloid is shown in FIG. 27 B and a photograph showing a watch, the surface of which is coated with a metal colloid is shown in FIG. 27 C, respectively.

Figure 27A:
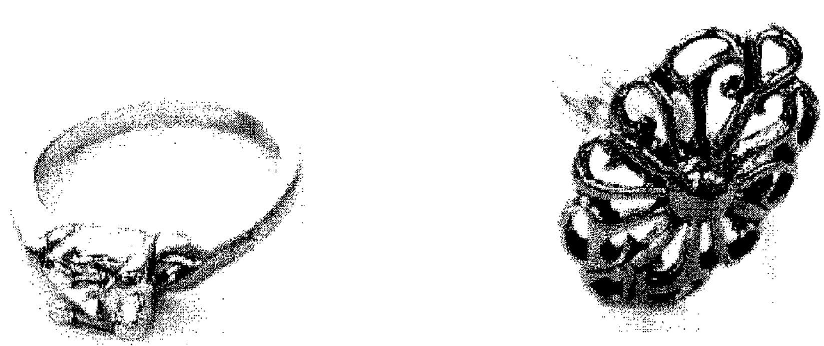
FIG. 27 A is a photograph of a ring, the surface of which is coated with a metal colloid.
Figure 27B:
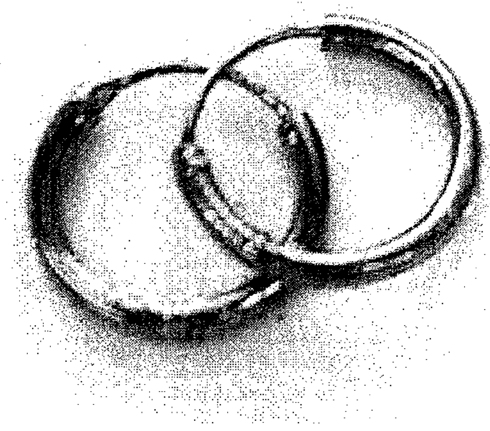
Figure 27C:
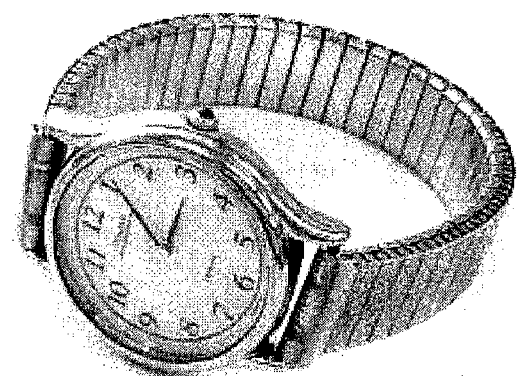

As is apparent from FIG. 27 A to FIG. 27 C, the resulting metal colloid-containing coat formed article is jewelry which shows metal gloss and color tone peculiar to metal and is excellent in brightness and design properties.

Example 70

The metal colloid prepared in Example 68, a natural nail and an artificial nail were prepared, respectively. By a method of coating the metal colloid using a writing brush for manicure shown in FIG. 12, the metal colloid was coated on the surface of the natural nail and the artificial nail. After coating, the dispersion medium in the metal colloid was sufficiently removed by drying with an air of a dryer to form a metal colloid-containing coat. A natural nail wherein a metal colloid-containing coat is formed on the surface by a coating method is shown in FIG. 28.

Figures 28, 29:
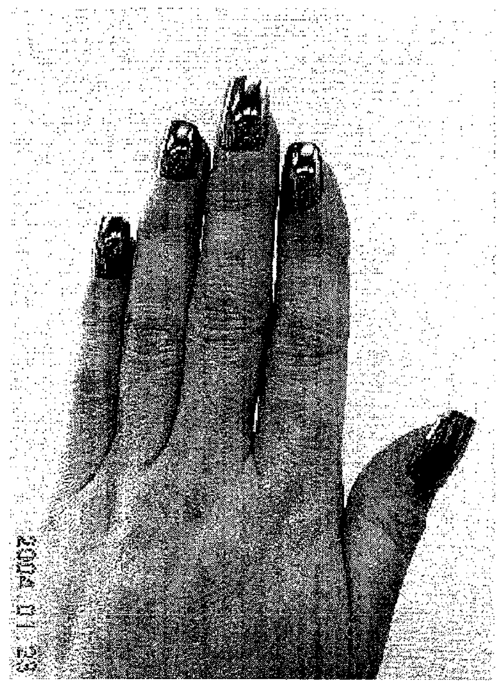
FIG. 28 is a photograph showing finger nails wherein metal colloid-containing coat is formed on the surface by the coating method of FIG. 12.
FIG. 29 is a photograph showing finger nails wherein a metal colloid-containing coat is formed by the spraying method of FIG. 14.

As is apparent from FIG. 28, the metal colloid-containing coat formed on the surface of the natural nail is a film which showed golden gloss and color tone peculiar to gold and had a metal specular surface which is excellent in smoothness.

Example 71

Using a method of spraying a metal colloid using an airbrush for manicure shown in FIG. 14, the metal colloid prepared in Example 68 was sprayed over the surface of a natural nail and the surface of an artificial nail. After spraying, the dispersion medium in the metal colloid was sufficiently removed by drying with an air of a dryer to form a metal colloid-containing coat. A natural nail wherein a metal colloid-containing coat is formed on the surface by a spraying method is shown in FIG. 29.

As is apparent from FIG. 29, the metal colloid-containing coat formed on the surface of the natural nail and the artificial nail showed golden gloss and color tone peculiar to gold and had a metal specular surface which has matted gloss and is excellent in smoothness, unlike the coat of Example 70 formed by coating using the writing brush.

Example 72

First, in the same manner as in Example 70, the metal colloid prepared in Example 68 was coated on the surface of a natural nail and the surface of an artificial nail using a writing brush for manicure. After coating, the dispersion medium in the metal colloid was sufficiently removed by drying with an air of a dryer to form a metal colloid-containing coat. Then, a top coating agent was coated on the metal colloid-containing coat thus formed by a wet-on-wet coating method and this top coating prevented the metal colloid-containing coat from being peeled off with ease. The metal colloid-containing coat formed on the surface of the artificial nail showed golden gloss and color tone peculiar to gold and had a metal specular surface which is excellent in smoothness, similar to the case of the coat obtained in Example 70.

Example 73

First, an artificial nail was prepared and an under coat layer was formed on the surface of an artificial nail. In the same manner as in Example 70, the metal colloid prepared in Example 68 was coated on the surface of the under coat layer using a writing brush for manicure. The metal colloid-containing coat formed on the surface of the artificial nail showed golden gloss and color tone peculiar to gold and had a metal specular surface which is excellent in smoothness, similar to the case of the coats obtained in Example 70 and Example 72.

Example 74

First, an artificial nail was prepared and an under coat layer was formed on the surface of an artificial nail. In the same manner as in Example 70, the metal colloid prepared in Example 68 was coated on the surface of the under coat layer using a writing brush for manicure. After coating, the dispersion medium in the metal colloid was sufficiently removed by drying with an air of a dryer to form a metal colloid-containing coat. Then, a top coating agent was coated on the metal colloid-containing coat thus formed by a wet-on-wet coating method and this top coating prevented the metal colloid-containing coat from being peeled off with ease. The metal colloid-containing coat formed on the surface of the artificial nail showed golden gloss and color tone peculiar to gold and had a metal specular surface which is excellent in smoothness, similar to the case of the coats obtained in Example 70, Example 72 and Example 73.

Example 75

In the same manner as in Example 74, except that the metal colloid was coated only at the tip portion of the nail using an airbrush, a metal colloid-containing coat was formed on the surface of an artificial nail. In the same manner as in Example 74, except that desired patterns were drawn on the surface of the nail using a writing brush for manicure in case of coating the metal colloid, a metal colloid-containing coat was formed on the surface of an artificial nail. The artificial nail coated with the metal colloid only at the tip portion using an airbrush and the artificial nail wherein desired patterns are drawn on the surface of the nail using a writing brush for manicure showed color tone peculiar to metal and were excellent in design properties, similar to Examples 70 to 74.

Example 76

In the same manner as in Example 74, except that the metal colloid prepared in Example 68 contains 0.5 to 3% of fine metal particles having an average particle size of 1 to 10 nm, a metal colloid-containing coat was formed on the surface of an artificial nail. The metal colloid-containing coat formed on the surface of the artificial nail shows a pink gold color tone and is excellent in design properties.

Example 77

First, an under coating agent was coated on the surface of an artificial nail and then dried to form an under coat layer. In the same manner as in Example 70, the metal colloid prepared in Example 68 was coated on the surface of the under coat layer using a writing brush for manicure. The dispersion medium in the metal colloid was removed by drying with an air of a dryer to form a metal colloid-containing coat. Then, a top coating agent was coated on the metal colloid-containing coat thus formed and, before completely drying the top coating agent, a lame agent as a material was scattered at desired points and diamond natural stones and pink sapphire natural stones were set thereon, and then these materials were fixed by pressing and immobilized by drying the top coating agent with an air of a dryer. Immobilization of these materials was enhanced by further coating the top coating agent. An artificial nail on which a metal colloid-containing coat is formed is shown in FIG. 30.

Figure 30:
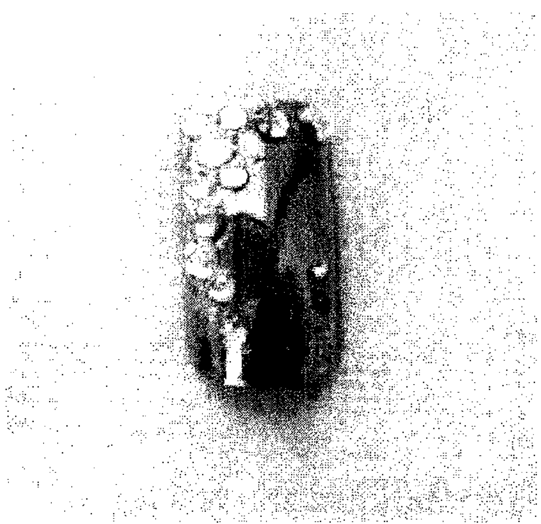
FIG. 30 is a photograph showing artificial nails of Example 77 wherein a metal colloid-containing coat, a lame agent and natural gems of diamond and pink sapphire are formed in combination on the surface.

As is apparent from FIG. 30, brightness and design properties were improved by using the metal colloid-containing coat in combination of the lame agent and natural gems of diamond and pink sapphire.

Example 78

First, the metal colloid prepared in Example 68 was coated only at the tip portion of an artificial nail using a writing brush for manicure. After coating, the dispersion medium in the metal colloid was removed by drying with an air of a dryer to form a metal colloid-containing coat. Then, a top coating agent was coated on the metal colloid-containing coat thus formed and, before completely drying the top coating agent, pearl and diamond natural stones as materials were arranged at the desired points, and then these materials were fixed by pressing and immobilized by drying the top coating agent with an air of a dryer. Immobilization of these materials was enhanced by further coating the top coating agent. The resulting artificial nail on which the metal colloid-containing coat is formed is shown in FIG. 31.

Figure 31:
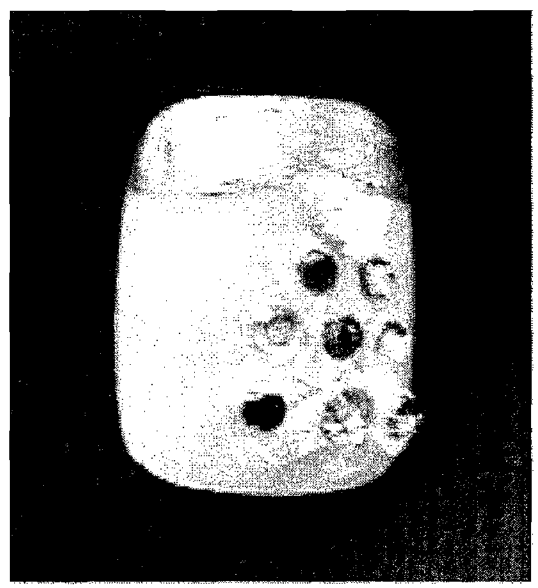
FIG. 31 is a photograph showing artificial nails of Example 78 wherein a metal colloid-containing coat and natural gems of ruby, diamond and sapphire are formed in combination on the surface.

As is apparent from FIG. 31, brightness and design properties were improved by using the metal colloid-containing coat formed only at the tip portion of the nail in combination with natural gems of pearl and diamond.

Example 79

First, desired patterns were drawn on the surface of an artificial nail with the metal colloid prepared in Example 68 using a writing brush for manicure. After drawing, the dispersion medium in the metal colloid was removed by drying with an air of a dryer to form a metal colloid-containing coat. Then, a top coating agent was coated on the entire surface of a nail and, before completely drying the top coating agent, a gold foil powder and diamond and pink sapphire natural stones as materials were set at the desired points, and then these materials were fixed by pressing and immobilized by drying the top coating agent with an air of a dryer. Immobilization of these materials was enhanced by further coating the top coating agent. Brightness and design properties were improved by using the metal colloid-containing coat in combination with the gold foil powder and natural gems of diamond and pink sapphire.

Example 80

First, as shown in FIG. 19, a coating solution of an acrylic resin was coated on one surface of a base material 2 made of a releasable synthetic paper to form a surface protective layer 4. Then, the gold colloid prepared in Example 68 was coated on the surface protective layer 4 to form a metal colloid-containing coat layer 5. Furthermore, a coating solution of a hot melt type resin was coated on the metal colloid-containing coat layer 5 to form an adhesive layer 6, thus obtaining a transfer sheet 1 wherein a transfer layer 3 comprising the surface protective layer 4, the metal colloid-containing coat layer 5 and an adhesive layer 6 is formed on the base material 2.

Example 81

In the same manner as in Example 80, except that characters or patterns were drawn by an ink jet printer to form a metal colloid-containing coat layer 5, a transfer sheet was produced.

Example 82

Each of the transfer sheets of Example 80 and Example 81 was thermally transferred under pressure to a paper, clothes, a leather and a glass to form a metal colloid-containing coat on the surface. The metal colloid-containing coat showed metal gloss and color tone peculiar to metal and was excellent in brightness. The coat was not peeled off even when rubbed with fingers. The method for thermal transfer under pressure can be conducted by a conventionally known method.

Example 83

A plasma-treated glass sheet measuring 150 mm×150 mm×1 mm was prepared and an ink tank of an ink jet printer was filled with the Au colloid having a concentration of 50% by weight obtained in Synthesis Example 55 of Example 68, and then 5 golden gloss colored lines having a line width of about 2 mm and a length of 100 mm were drawn on the glass sheet. The drawn glass sheet was dried at room temperature and the electrical resistance value of the golden gloss colored line was measured. As a result, it was $9.8\times10^{-6}$ Ω·cm.

Example 84

The glass sheet with lines obtained in Example 83 was fired by maintaining in an atmospheric air at a temperature of 300° C. for 10 minutes and the electrical resistance value of the golden gloss colored line formed on the glass sheet was measured. As a result, it was $2.7\times10^{-6}$ Ω·cm.

Example 85

Two alumina sheets each measuring 50 mm×50 mm×1.0 mm were prepared and screen printing was conducted using the Au colloid having a concentration of 50% by weight obtained in Synthesis Examples 72 and 73 of Example 68 to form each coat measuring 10 mm×25 mm on the surface of the alumina sheets. The alumina sheets with the coat formed thereon were air-dried in an atmospheric air at 25° C. for one hour. The electrical resistance value of the resulting coats was measured. As a result, the resistance value of the coat formed using the colloid of Synthesis Example 72 was $7.7\times10^{-6}$ Ω·cm and the resistance value of the coat formed using the colloid of Synthesis Example 73 was $9.2\times10^{-6}$ Ω·cm.

Example 86

Two alumina sheets each measuring 50 mm×50 mm×1.0 mm were prepared and offset printing was conducted using the Au colloid having a concentration of 50% by weight obtained in Synthesis Example 74 of Example 68 to form each coat measuring 10 mm×25 mm on the surface of the alumina sheets. One alumina sheet with the coat formed thereon was air-dried in an atmospheric air at 25° C. for one hour, and the other alumina sheet with the coat formed thereon was fired in an atmospheric air at 450° C. for one minute and then air-dried. After cooling to room temperature, the resistance value of the resulting coats was measured. As a result, the resistance value of the air-dried coat was $8.8\times10^{-6}$ Ω·cm and the resistance value of the fired coat was $2.5\times10^{-6}$ Ω·cm.

Example 87

Two glass sheets each measuring 50 mm×50 mm×1.0 mm were prepared and spray-coated with the Au colloid having a concentration of 50% by weight obtained in Synthesis Example 75 of Example 68 to form each coat measuring 10 mm×25 mm on the surface of the glass sheets. One glass sheet with the coat formed thereon was air-dried in an atmospheric air at 15° C. for 30 minutes. The other glass sheet with the coat formed thereon was fired in an atmospheric air at 350° C. for one minute and then air-dried. After cooling to room temperature, the resistance value of the resulting coats was measured. As a result, the resistance value of the air-dried coat was $3.5\times10^{-5}$ Ω·cm and the resistance value of the fired coat was $3.7\times10^{-6}$ Ω·cm.

Example 88

A glass sheet measuring 50 mm×50 mm×1.0 mm was prepared and spin-coated with the Au colloid having a concentration of 50% by weight obtained in Synthesis Example 76 of Example 68 under the conditions of a rotating speed of 200 rpm and 3 minutes to form a coat on the surface of the glass sheet. The glass sheet with the coat formed thereon was air-dried in an atmospheric air at 25° C. for one hour. The electrical resistance value of the resulting coat was measured. As a result, the resistance value was $7.1\times10^{-6}$ Ω·cm.

Example 89

Four alumina sheets each measuring 50 mm×50 mm×1.0 mm were prepared and slit coat printing was conducted using the Au colloid having a concentration of 50% by weight obtained in Synthesis Examples 77, 78, 79 and 80 of Example 68 to form each coat measuring 10 mm×25 mm on the surface of the alumina sheets. The alumina sheets with the coat formed thereon were air-dried in an atmospheric air at 25° C. for one hour. The electrical resistance value of the resulting coats was measured. As a result, the resistance value of the coat formed using the colloid of Synthesis Example 77 was $1.7\times10^{-5}$ Ω·cm, the resistance value of the coat formed using the colloid of Synthesis Example 78 was $9.1\times10^{-6}$ Ω·cm, the resistance value of the coat formed using the colloid of Synthesis Example 79 was $1.6\times10^{-5}$ Ω·cm and the resistance value of the coat formed using the colloid of Synthesis Example 80 was $8.7\times10^{-6}$ Ω·cm.

Example 90

Five alumina sheets each measuring 50 mm×50 mm×1.0 mm were prepared and screen printing was conducted using the Au colloid having a concentration of 50% by weight obtained in Synthesis Examples 81, 82, 83, 84 and 85 of Example 68 to form each coat measuring 10 mm×25 mm on the surface of the alumina sheets. The alumina sheets with the coat formed thereon were air-dried in an atmospheric air at 40° C. for one hour. The electrical resistance value of the resulting coats was measured. As a result, the resistance value of the coat formed using the colloid of Synthesis Example 81 was $5.7\times10^{-6}$ Ω·cm, the resistance value of the coat formed using the colloid of Synthesis Example 82 was $5.1\times10^{-6}$ Ω·cm, the resistance value of the coat formed using the colloid of Synthesis Example 83 was $6.6\times10^{-5}$ Ω·cm, the resistance value of the coat formed using the colloid of Synthesis Example 84 was $7.0\times10^{-6}$ Ω·cm and the resistance value of the coat formed using the colloid of Synthesis Example 85 was $5.7\times10^{-5}$ Ω·cm.

Example 91

An alumina sheet measuring 50 mm×50 mm×1.0 mm was prepared and screen printing was conducted using the Ag colloid having a concentration of 50% by weight obtained in Synthesis Example 86 of Example 68 to form a coat measuring 10 mm×25 mm on the surface of the alumina sheet. The alumina sheet with the coat formed thereon was dried in an atmospheric air at 60° C. for 30 minute. The electrical resistance value of the resulting coat was measured. As a result, the resistance value was $4.1\times10^{-6}$ Ω·cm.

Example 92

As shown in FIG. 20 A, there was prepared a cartridge 10 for pen which is composed of a tubular body 11 having a closed lower portion, a lid portion 13 which is joined with the upper portion of the tubular body 11 and is provided with a continuous hole at center, and a spherical plug 14 inserted loosely into the continuous hole of the lid portion 13, the tubular body 11 being filled with the dilute metal colloidal solution 12 prepared in Example 68.

As shown in FIG. 20 B, a pen 20 comprising the cartridge 10 for pen incorporated thereinto was prepared. This pen 20 is composed of a cylindrical upper shaft barrel 21, a cylindrical lower shaft barrel 22, the upper end of which can be connected to the lower end of the upper shaft barrel 21, and a tip 26 which is connected to the other end of the lower shaft barrel 22. The inner wall of the lower shaft barrel 22 is provided with a connection portion 23 which inserts the cartridge 10 for pen and contacts with the lid portion 13, thereby to push up the spherical plug 14 into the cartridge 10 for pen. In the connection portion 23, there is provided a core portion 24 capable of being impregnated with the metal colloidal discharging from the cartridge 10 due to gravity while protruding the other end of the lower shaft barrel 22 when the cartridge 10 for pen is connected to the connection portion 23 and the spherical plug 14 is pushed up by the connection portion 23. The tip 26 connected to the other end of the lower shaft barrel 22 serves to eject the metal colloid, with which the core portion 24 is impregnated, from the tip.

The cartridge 10 for pen was connected to the pen 20 by contacting the lid portion 13 of the cartridge with the connection portion 23 and pushing the connection portion 23 and the plug 14 into the cartridge 10 for pen. In that case, the metal colloidal 12 filled into the cartridge 10 is discharged from the gap between the lid portion 13 and the spherical plug 14 and thus the core portion 24 is impregnated with the dilute metal colloidal solution, which is supplied to the tip 26 through the core portion 24. The pen comprising the cartridge 10 for pen connected thereto is easy to draw and was capable of drawing smoothly. This pen is very advantageous to write desired characters and to draw predetermined patterns on the desired base material, and the characters and patterns drawn by the pen showed metal gloss and color tone peculiar to metal and were excellent in brightness.

Example 93

As shown in FIG. 21, there was prepared a disposable ampul 30 which is composed of a tubular body 31 having a closed lower portion, a cut portion 33 joined with the upper portion of the tubular body 31, and a lid portion 32, the cut portion 33 being provided with a smaller width than that of the tubular body 31 and the lid portion 32 so that it can be cut by a hand operation, the disposable ampul having a structure that the dilute metal colloidal solution 34 prepared in Example 68 is sealed by thermal contact bonding of the cut portion 33 and the lid portion 32 after filling the tubular body 31 with the dilute metal colloidal solution 34.

In the disposable ampul 30 thus obtained, the lid portion 32 can be easily cut from the cut portion 33 through the lever rule by laterally rotating the lid portion 32 and the cut surface is communicated with the inside of the tubular body 31. The metal colloid filled in the tubular body 31 can be used after taking out from the communicated portion.

Example 94

Figure 32A:
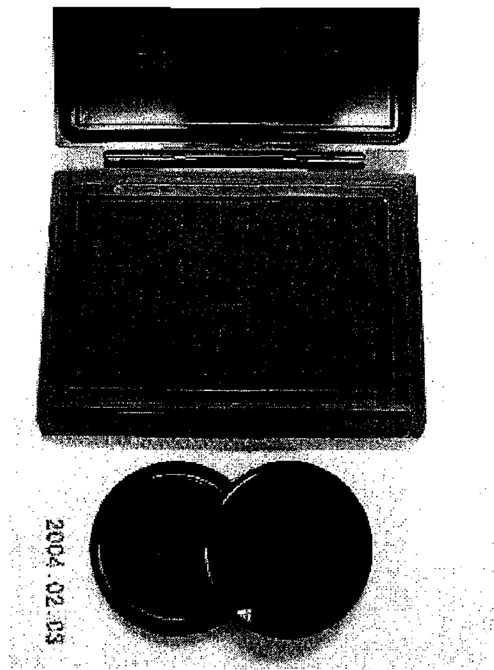
FIG. 32 A is a photograph showing a stamp pad and seal impression pad which are made by impregnating with a metal colloid of Example 94.
Figure 32B:
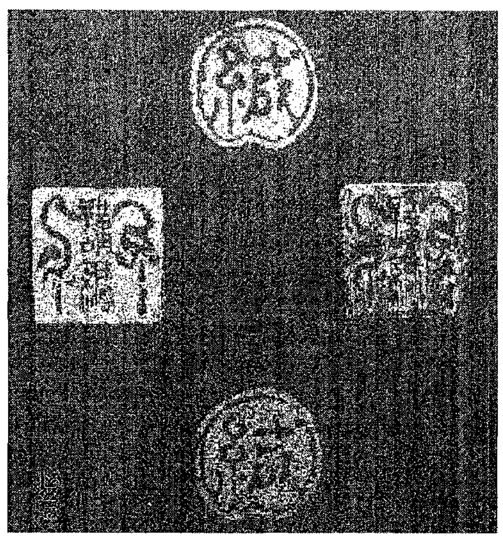

The concentration of the metal colloid prepared in Example 68 was adjusted to 20% by weight. A stamp pad and a seal impression pad were produced by sufficiently impregnating with the resulting metal colloid. Photographs of the resulting stamp pad and seal impression pad are shown in FIG. 32 A. A card wherein patterns are formed using the stamp pad and the seal impression pad is also shown in FIG. 32 B. As is apparent from FIG. 32 B, the patterns made of the metal colloid formed by using the stamp pad or seal impression pad showed color tone and metal gloss peculiar to gold.

Example 95

Figure 33A:
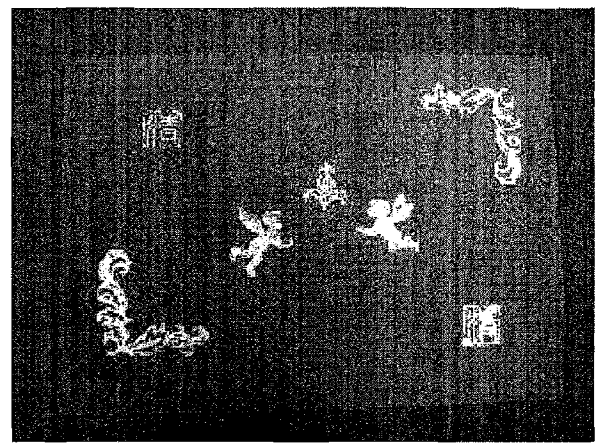
FIG. 33 A is a photograph showing a greeting card wherein a metal colloid-containing coat is formed by drawing a picture using an ink jet printer apparatus of Example 95.
Figure 33B:
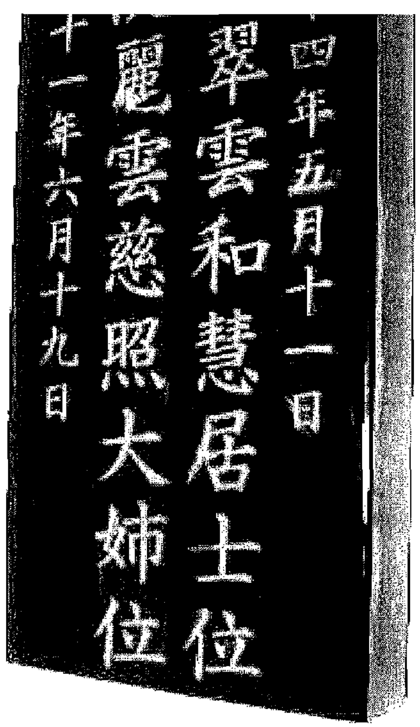

The concentration of the metal colloid prepared in Example 68 was adjusted to 20% by weight. As the base material, a paper, a leather and a lumber were used. Using the resulting metal colloid, a spiral scoring test was conducted by an ink jet printer apparatus. Using the paper, a business card, a greeting card, a memorial card and an invitation card were produced. In case of using the leather, a leather wallet was drawn. In case of using the lumber, desired characters were written on a mortuary tablet. A photograph of a greeting card wherein a metal colloid-containing coat is formed by drawing using an ink jet printer apparatus is shown in FIG. 33 A and a photograph of a mortuary tablet wherein a metal colloid-containing coat is formed by drawing using an ink jet printer apparatus is shown in FIG. 33 B, respectively. As is apparent from FIG. 33 A and FIG. 33 B, the patterns written by an ink jet printer apparatus using the metal colloid showed color tone and metal gloss peculiar to gold.

Example 96

Using the metal colloid prepared in Example 68 as an ink, characters and patterns were drawn on a colored paper by a writing brush. The characters and patterns showed metal gloss and color tone peculiar to metal and were excellent in brightness. In case of drawing characters or patterns, a pen filled with the metal colloid described in Example 92 as an ink may be used.

Example 97

Using the metal colloid prepared in Example 68 as an ink, a hand print and a foot print were formed on a colored paper. The hand print and the foot print showed metal gloss and color tone metal peculiar to metal and were excellent in brightness.

Example 98

First, a paper wherein patterns are written on the surface by a commercially available black ink using a seal impression and a stamp, a colored paper wherein characters and patterns are drawn on the surface using a black pen, and a colored paper wherein a hand print and a foot print are formed using a black ink were prepared. Using an image scanner, the surface of the paper and that of the colored paper were scanned and the resulting image data were inputted into a computer. By an ink jet printer using the metal colloid prepared in Example 68 as an ink, image data were printed on the paper and the colored paper based on the inputted image data. Characters and patterns printed on the paper and the colored paper using the metal colloid of the present invention showed the same shape as that of black colored characters and patterns drawn and also showed metal gloss and color tone peculiar to metal and were excellent in brightness.

In Example 98, using the image scanner, the surface of the paper and that of the colored paper were scanned and the resulting image data were inputted into a computer and then printed using the ink jet printer. Using the image scanner, not only base papers such as paper and colored paper, but also a photograph of these base papers, and a print and a publication in which these patterns and characters are described may be scanned and the resulting image data may be inputted into a computer and directly printed using an ink jet printer.

The metal colloidal particles of the present invention have been obtained by solving the above problems in a conventional metal colloid and the method for producing the same, and are excellent in long-term stability of a colloidal solution and are suited for thin-filming. Also, the metal colloidal particles can easily form a metal specular glossy area on various base materials. Furthermore, the metal colloidal particles can easily form a metal glossy area showing various gold-based basic tone color tones on various base materials.

The metal colloid-containing coat formed article and the transfer sheet of the present invention comprise a metal colloid-containing coat wherein a coat having a metal specular glossy area showing various color tones and having excellent heat resistance is formed.

In the base material with a conductive film of the present invention, a conductive film having a metal specular glossy area with various color tones and excellent heat resistance, and also having low resistance.

Furthermore, the pen, the brush-pencil, the cartridge for pen, the disposable ampul, the stamp pad and the seal impression pad of the present invention are excellent in quality-retaining property of the metal colloid filled or impregnated. The drawn material obtained by using them has color tone and metal gloss peculiar to metal.

The invention claimed is:

1. Metal colloidal particles capable of forming a metal colloid by dispersing in either or both of an aqueous dispersion medium and a nonaqueous dispersion medium in a predetermined proportion while mixing, said metal colloidal particles comprising:

metal particles; and a protective agent composed of a carbon skeleton which contains a coordination-modified site and one or more functional groups, wherein the protective agent is bonded to a surface of the metal particles through the coordination-modified site, the coordination-modified site consists of oxygen and is located at one end of the carbon skeleton, and the functional groups are located at another end of the carbon skeleton and are selected from the group consisting of alkoxysilyl group, silanol group and hydroxyalkyl group.

2. A metal colloid, wherein the metal colloidal particles of claim 1 are dispersed in either or both of an aqueous dispersion medium and a nonaqueous dispersion medium in a predetermined proportion while mixing.

3. A metal colloid, wherein the metal colloidal particles of claim 1 are mixed with a sol-gel solution in a predetermined proportion.

4. The metal colloid according to claim 3, wherein the sol-gel solution is a solution capable of forming at least one compound selected from the group consisting of silica, titania, zirconia, alumina, tantalum oxide and niobium oxide.

* * * * *